US011613605B2

(12) United States Patent
Kol et al.

(10) Patent No.: US 11,613,605 B2
(45) Date of Patent: Mar. 28, 2023

(54) BLOCK COPOLYMERS OF CYCLIC ESTERS AND PROCESSES FOR PREPARING SAME

(71) Applicant: Ramot at Tel-Aviv University Ltd., Tel-Aviv (IL)

(72) Inventors: Moshe Kol, Tel Aviv (IL); Tomer Rosen, Tel Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 280 days.

(21) Appl. No.: 17/023,463

(22) Filed: Sep. 17, 2020

(65) Prior Publication Data

US 2021/0002417 A1 Jan. 7, 2021

Related U.S. Application Data

(62) Division of application No. 15/756,131, filed as application No. PCT/IL2017/050735 on Jun. 29, 2017, now Pat. No. 10,808,073.

(60) Provisional application No. 62/356,038, filed on Jun. 29, 2016.

(51) Int. Cl.
*C08G 63/08* (2006.01)
*C08G 63/82* (2006.01)
*C07F 3/02* (2006.01)
*C07D 213/38* (2006.01)
*B01J 31/18* (2006.01)

(52) U.S. Cl.
CPC ............ *C08G 63/08* (2013.01); *B01J 31/181* (2013.01); *C07D 213/38* (2013.01); *C07F 3/02* (2013.01); *C08G 63/823* (2013.01); *B01J 2231/14* (2013.01); *B01J 2531/22* (2013.01)

(58) Field of Classification Search
CPC ...... C08G 63/823; C08G 63/08; C08G 63/83; C07F 3/02
See application file for complete search history.

(56) References Cited

U.S. PATENT DOCUMENTS

| 5,346,966 | A | 9/1994 | Spinu |
| 2011/0105695 | A1 | 5/2011 | Schroeder et al. |
| 2017/0349710 | A1 | 12/2017 | Jasinska-Walc et al. |
| 2018/0251593 | A1 | 9/2018 | Koi et al. |
| 2019/0039058 | A1 | 2/2019 | Koi et al. |
| 2022/0395820 | A1 | 12/2022 | Kol et al. |

FOREIGN PATENT DOCUMENTS

| CN | 101970527 | 2/2011 |
| WO | WO 96/019519 | 6/1996 |
| WO | WO 2016/026859 | 2/2016 |
| WO | WO 2017/137990 | 8/2017 |
| WO | WO 2009/045881 | 9/2017 |
| WO | WO 2018/002941 | 1/2018 |

OTHER PUBLICATIONS

USPTO structure search, Jan. 2023.*
Communication Pursuant to Article 94(3) EPC dated Sep. 24, 2020 From the European Patent Office Re. Application No. 17749980.3. (5 Pages).
Zhang et al. "Versatile Supramolecular Copper (II) Complexes for Henry and Aza-Henry Reactions", Advanced Synthesis & Catalysis, XP055732198, 351(9): 1255-1262, Published Online Jun. 2, 2009.
Communication Pursuant to Article 94(3) EPC dated Jan. 28, 2020 From the European Patent Office Re. Application No. 17749980.3. (3 Pages).
International Preliminary Report on Patentability dated Jan. 10, 2019 From the International Bureau of WIPO Re. Application No. PCT/IL2017/050735. (17 Pages).
International Search Report and the Written Opinion dated Sep. 3, 2017 From the International Searching Authority Re. Application No. PCT/IL2017/050735. (17 Pages).
International Search Report and the Written Opinion dated May 15, 2017 From the International Searching Authority Re. Application No. PCT/IL2017/050161. (10 Pages).
Notice of Allowance dated Jun. 17, 2020 from the US Patent and Trademark Office Re. U.S. Appl. No. 15/756,131. (11 pages).
Notification of Office Action and Search Report dated Nov. 25, 2019 From the State Intellectual Property Office of the People's Republic of China Re. Application No. 201780003899.4 and Its Translation of Office Action Into English. (23 Pages).
Office Action dated Jul. 30, 2020 From the Israel Patent Office Re. Application No. 261023. (3 Pages).
Official Action dated Jul. 14, 2020 from the US Patent and Trademark Office Re. U.S. Appl. No. 16/076,365. (20 pages).
Official Action dated Jan. 29, 2020 From the US Patent and Trademark Office Re. Application No. 151756, 131. (17 pages).
Supplementary European Search Report and the European Search Opinion dated Jan. 15, 2020 From the European Patent Office Re. Application No. 17819510.3.(9 Pages).
Supplementary European Search Report and the European Search Opinion dated May 22, 2019 From the European Patent Office Re. Application No. 17749980.3. (7 Pages).
Chen et al. "Magnesium and Zinc Complexes Containing Pendant Pyrazolylephenolate Ligands as Catalysts for Ring Opening Polymerization of Cyclic Esters", Journal of Organometallic Chemistry, 738: 1-9, Aug. 15, 2013.
Chiang et al. "Fe[III] Bipyrrolidine Phenoxide Complexes and Their Oxidized Analogues", Inorganic Chemistry, 53(11): 5810-5819, May 9, 2014.

(Continued)

*Primary Examiner* — Gregory Listvoyb

(57) ABSTRACT

Novel processes of preparing block polyester copolymers while precisely controlling the stereoconfiguration (e.g., tacticity), chemical composition and/or length of each unit (block) are provided. Block polyester copolymers featuring desirable combinations of two or more blocks featuring different stereoconfiguration (e.g., tacticity), chemical composition and/or length, including triblock, tetrablock and higher block copolymers are also provided. A novel family of organometallic magnesium complexes and uses thereof in preparing polyesters and block polyester copolymers are also provided.

17 Claims, 9 Drawing Sheets

(56) References Cited

OTHER PUBLICATIONS

Chomitz et al. "Synthesis and Reactivity of Metal Complexes Supported by the Tetradentate Monoanionic Ligand Bis(2-Picolyl)(2-Hydroxy-3,5-Di-Tert-Butylbenzyl)Amide (BPPA)", Inorganic Chemistry, XP055450351, 46(17): 7199-7209, Published on Web Jul. 26, 2007. p. 7201, Compound H(BPPA).

Contreras et al. "Synthesis of Epsilon-Caprolactone-B-L-Lactide Block Copolymers by Mean Sequential Polymerization, Using Diphenylzinc as Initiator", Polymer Bulletin, XP055450336, 71(7): 1661-1674, Published Online May 1, 2014.

Darensbourg et al. "Ring-Opening Polymerization of Lactides Catalyzed by Natural Amino-Acid Based Zinc Catalysts", Inorganic Chemistry, 49(5): 2360-2371, Feb. 1, 2010.

Dong et al. "Synthesis and Characterization of Stereoblock Poly(Lactic Acid)s", Engineering Plastics Applications, 39(11): Dec. 17-19, 2011 & English Translation.

Gross et al. "Zinc Complex Chemistry of N,N,O Ligands Providing a Hydrophobic Cavity", Inorganic Chemistry, XP055450349, 44(9): 3321-3329, Published on Web Apr. 5, 2005. p. 3322, Compounds L1, L2, L3, L4.

In't Veld et al. "Melt Block Copolymerization of Epsilon-Caprolactone and L-Lactide", Journal of Polymer Science, Part A: Polymer Chemistry, XP055450333, 35(2): 219-226, Jan. 30, 1997.

Labourdette et al. "Unusually Stable Chiral Ethyl Zinc Complexes: Reactivity and Polymerization of Lactide", Organometallics, 28(5): 1309-1319, Publication on Web Feb. 11, 2009.

Leavell et al. "Conformational Studies of ZN-Ligand-Hexose Diastereomers Using Ion Mobility Measurements and Density Functional Theory Calculations", Journal of the American Society of Mass Spectrometry, 13(3): 284-293, Published Online Jan. 22, 2002. p. 288, Fig.3.

Luo et al. "Monoprotic Tetradentate N3O-Donor Ligands and Their Cu(II) and Ni(TT) Complexes", Inorganic Chemistry, 38(9): 2071-2078, Apr. 17, 1999. p. 2071, Chart 1, p. 2076, Fig.1.

Michel et al. "Galactose Oxidase Models: Creation and Modification of Proton Transfer Coupled to Copper(II) Coordination Processes in Pro-Phenoxyl Ligands", European Journal of Inorganic Chemistry, XP055450366, 2006(18): 3684-3696, Pubhshed Online Aug. 3, 2006. p. 3685, Scheme 1, Compounds HL-tBu, HLH, HLMe.

Michel et al. "Galactose Oxidase Models: Solution Chemistry, and Phenoxyl Radical Generation Mediated by the Copper Status", Chemistry—A European Journal, XP055450364, 10(17): 4115-4125, Jul. 21, 2004. p. 4117, Fig.1b, Compounds HLOMe,HLtBu,HLF, Fig.1c, Compound HLotBu.

Nagataki et al. "Ligand Effects on NiII-Catalysed Alkane-Hydroxylation With M-CPBA", Dalton Transactions, XP055450360, 2007(11): 1120-1128, Published Online Feb. 6, 2007. p. 1121, Compounds DtbpPym2H, DtbpPye2H.

Rosen et al. "Divergent [{ONNN}Mg—Cl] Complexes in Highly Active and Living Lactide Polymerization", Chemical Science, XP055450370, 8: 5476-5481, May 26, 2017.

Rosen et al. "Tailor-Made Stereoblock Copolymers of Poly(Lactic Acid) by a Truly Living Polymerization Catalyst", Journal of the American Chemical Society, JACS, XP055587944, 138: 12041-12044, Sep. 7, 2016.

Rosen et al. "Zinc Complexes of Sequential Tetradentate Monoanionic Lisands in the Isoselective Polymerization of Rac-Lactide", Chemistry—A European Journal, XP055450367, 22(33): 11533-11536, Jul. 4, 2016. Gable 1, Layout 2, 2nd Scheme.

Rosen et al. Divergent [|ONNN|Mg—Cl] Complexes in Highly Active and Living Lactide Polymerization, Chemical Science, 8: 5476-5481, Published Online May 26, 2017.

Schneiderman et al. "Poly(Lactide)-Block-Poly(Epsilon-Caprolactone-Co-Epsilon-Decalactone)-Block-Poly(Lactide) Copolymer Elastomers", Polymer Chemistry, XP055450337, 6(19): 3641-3651, May 21, 2015.

Shimazaki et al. "Zinc(II)-Phenoxyl Radical Complexes: Dependence on Complexation Properties of Zn-Phenolate Species", Inorganica Chimica Acta, XP026020367, 362(7): 2467-2474, Available Online Nov. 18, 2008. Fig.1, Compounds tBul, tBul(Mepy), tBul(Mepy)2.

Stridsberg "Controlled Ring-Opening Polymerization: Polymers With Designed Macromolecular Architecture", PhD Dissertation, Department of Polymer Technology, Royal Institute of Technology, Stockholm, Sweden, XP055450329, p. 1-94, Mar. 3, 2000. Para 5.5.

Wang et al. "[ONN]-Type Amine Pyridine(s) Phenolate-Based Oxovanadium(v) Catalysts for Ethylene Homo-and Copolymerization", Dalton Transactions, XP055450340, 43(34): 12926-12934, Jul. 31, 2014. p. 12927, Compound 2a.

Wang et al. "Highly Active Magnesium Initiators for Ring-Opening Polymerization of Rac-Lactide", Macromolecules, XP055450372, 43(16): 6535-6537, Published on Web Jul. 27, 2010.

Wei et al. "Synthesis of Poly(Epsilon-Caprolactone)-Poly(L-Lactide) Block Copolymers by Melt or Solution Sequential Copolymerization Using Nontoxic Dibutylmagnesium as Initiator", Polymer Bulletin, XP019655258, 61(4): 407-413, Pubhshed Online Jul. 4, 2008.

Williams et al. "A Highly Active Zinc Catalyst for the Controlled Polymerization of Lactide", Journal of the American Chemical Society, JACS, 125(37): 11350-11359, Sep. 17, 2003.

Wong et al. "Mononuclear Iron(III) Complexes Supported by Tripodal N3O Ligands: Synthesis, Structure and Reactivity Towards DNA Cleavage", Inorganica Chimica Acta, XP026977168, 363(6): 1246-1253, Available Online Dec. 29, 2009. Fig.1, Compound of General Formula III (Each of RI and R2 Is T-But and R3 Is H or Me), Scheme 1, Compounds HL1, HL2, HL3.

Zheng et al. "Zinc and Enolato-Magnesium Complexes Based on Bi-, Tri- and Tetradentate Aminophenolate Ligands", New Journal of Chemistry, XP009123110, 32(12): 2279-2291, Published Online Oct. 14, 2008.

Office Action dated Sep. 30, 2021 From the Israel Patent Office Re. Application No. 261023 and Its Translation Into English. (7 Pages).

Official Action dated Dec. 22, 2021 from US Patent and Trademark Office Re. U.S. Appl. No. 16/076,365. (15 pages).

Advisory Action dated Apr. 13, 2021 From the US Patent and Trademark Office Re. U.S. Appl. No. 16/076,365. (7 Pages).

Final Official Action dated Jan. 7, 2021 from the US Patent and Trademark Office Re. U.S. Appl. No. 16/076,365. (13 pages).

Anjos et al. "Synthesis, Characterization and Structure of a New Zinc(II) Complex Containing the Hexadentate N,N?,N,N?-bis[(2-hydroxy-3,5-di-tert-butylbenzyl)(2-pyridylmethyl)]-ethylenediamine Ligand: Generation of Phenoxyl Radical Species", 358(11):3106-3114, Jul. 1, 2005.

Official Action dated Jun. 3, 2021 From the US Patent and Trademark Office Re. U.S. Appl. No. 16/076,365. (8 Pages).

* cited by examiner

BLOCK COPOLYMERS OF CYCLIC ESTERS AND PROCESSES FOR PREPARING SAME

RELATED APPLICATIONS

This application is a division of U.S. patent application Ser. No. 15/756,131 filed on Feb. 28, 2018, which is a National Phase of PCT Patent Application No. PCT/IL2017/050735 having International Filing Date of Jun. 29, 2017, which claims the benefit of priority under 35 USC § 119(e) of U.S. Provisional Patent Application No. 62/356,038 filed on Jun. 29, 2016. The contents of the above applications are all incorporated by reference as if fully set forth herein in their entirety.

FIELD AND BACKGROUND OF THE INVENTION

The present invention, in some embodiments thereof, relates to chemistry and, more particularly, but not exclusively, to block polyester copolymers, including, but not limited to, stereoblock polyester copolymers, featuring high precision, and to one-pot ring opening polymerization processes for preparing same.

Block copolymers are copolymers consisting of regularly or statistically alternating two or more different homopolymer blocks that differ in composition or structure. Each homopolymer block in a block copolymer represents polymerized monomers of one type. The homopolymer blocks can differ from one another by the chemical composition of the monomers composing each homopolymer block and/or by the stereoconfiguration of the homopolymer block (e.g. isotactic and syndiotactic configurations).

For example, while copolymers composed of A and B monomers may be arranged is a random or alternating fashion as follows:

-A-A-B-A-B-B-A-B-A-A-B-B-B-A-    random copolymer

-A-B-A-B-A-B-A-B-A-B-A-B-    alternating capolymer

Block copolymers comprise clusters of monomers A and B as exemplified in the following non-limiting example of a diblock copolymer:

-A-A-A-A-A-A-B-B-B-B-B-B-    block copolymer

Block copolymers typically combine the properties of their constituent blocks, thus differentiating such copolymers from random copolymers that do not exhibit the characteristics of each of their components.

The number of homopolymer blocks may be specific (e.g., diblock, triblock, tetrablock, etc.) or non-specific, if the blocks are formed randomly (multiblock).

The properties of block copolymers may be similar to the sum of the properties of a mixture of the homopolymers composing them, but the presence of chemical bonds between the blocks ensures their stability and prevents their separation with the release of individual components. In addition, block copolymers may exhibit unique properties such as formation of micelles. Synthesis of block copolymers significantly expands the possibilities for modifying the properties of polymers. The combination of properties of homopolymers in a block copolymer typically manifests itself in the thermomechanical properties and transition temperatures of block copolymers.

Among the sophisticated polymers, block copolymers are the most important group, because they can lead to materials that combine desirable properties of each of the blocks, such as, for example, crystallinity and elasticity, and to specialty morphologies such as lamellae, rods or spheres by microphase separation of the blocks into specific regimes.

Plastic materials play an inseparable role of modern life. Their ready availability from cheap starting materials combined with established technologies for their production, and their immense range of properties make them core ingredients in durable goods such as construction materials, household items, fibers, and auto parts, in disposable materials such as food packaging disposable cups and plates, and in biomedical and biocompatible products including artificial implants, stents, sutures, etc.

The properties of plastic materials are derived from their molecular structure, namely, the building blocks from which the polymer chains are built, the type and degree of regularity of the building blocks in the chains, such as the regioregularity and stereoregularity, the general type of the polymer, e.g., linear, branched, or cross-linked type polymer, and the possibility of combining different building blocks either within the same chain or in mixtures of separate chains. Properties such as melting transition, glass transition, impact resistance, tackiness, film formation, gas permeability, rate of decomposition, etc., are a direct outcome of the specific structure of the polymeric material.

The ability to manufacture polymeric materials having a 'tailor-made' structure is a key-step on the way to improving the properties of existing plastics, replacing old plastics with new ones having lower environmental signature, and finding new applications for plastic materials.

Biodegradable plastic materials derived from bio-renewable resources such as poly(lactic acid) (PLA) are attracting considerable current interest. PLA combines promising mechanical and physical properties and is produced from starting materials originating from biomass such as corn. As the degradation products of PLA are non-toxic, it has found biomedical applications (sutures, implants, pulmonary stents, scaffolds for tissue engineering, etc.) as well as commodity applications.

The most practical method for the production of PLA and related polyesters is the catalytic Ring Opening Polymerization (ROP) of cyclic esters (lactones).

Lactide is chiral having two stereogenic centers leading to three possible stereoisomers: L-lactide (the natural stereoisomer), D-lactide, and meso-lactide.

Ring opening polymerization of lactides may therefore lead to PLAs of various tacticities, as shown in Background Art FIG. 1.

The properties of PLA are determined by its microstructural regularity. Isotactic PLA, composed of identical repeat units of either L-LA or D-LA is a crystalline polymer. PDLA and PLLA, the two enantiomeric homochiral strands, co-crystallize as a stereocomplex (SC) phase whose properties are superior to those of the homochiral (HC) crystal phase. However, this crystallization tendency diminishes for higher molecular weight PLA.

More advanced PLA generations are expected to include different types of lactide isomers assembled in an ordered (regioregular) fashion, and in particular block copolymers. In particular, isotactic stereoblock-PLA composed of covalently bound PDLA and PLLA blocks has been targeted.

Copolymers of PLA and related aliphatic polyesters have also been found highly useful in biomedicine and pharmaceutics. In particular, copolymers of PLA and poly(F-caprolactone) (PCL) have been explored as components of drug delivery systems, dissolvable sutures and scaffolds for tissue engineering. The two polymers are immiscible, thus exhibiting distinct melting and crystallization temperatures when mixed. However, when copolymerized, an improved polymer is obtained having versatile thermal and mechanical properties and adjustable degradation time. While gradient multiblock or random copolymers of PLA and PCL are usually amorphous, block copolymers of PLA and PCL are crystalline materials. Stereocomplexation was observed in blends of enantiomeric PLA-PCL diblock and symmetric triblocks copolymers, exhibiting higher melting temperatures compared to enantiomeric copolymers. Therefore, copolymers of PCL with PLA stereoblocks have also been targeted.

Tailor-made plastics such as described hereinabove require sophisticated catalysts, and, in the past 15 years, there has been an enormous effort to try and develop more advanced catalysts.

The most successful catalysts for lactide and related cyclic-ester polymerizations are metal complexes featuring a chelating ligand that remains bound to the metal, and a labile alkoxo group that initiates the polymerization process. Some of the catalysts described in the literature in the past years, were reported to be living, and were reported to lead to diblock and triblock copolymers of lactide enantiomers, or lactide and related cyclic esters. See, for example, Othman et al. *Polymer* 53, 2443 (2012); Aluthge et al. *Macromolecules* 46, 3965 (2013); and Amgoune et al. *Chem. Eur. J.* 2006, 12, 169.

However, these catalysts suffer from high cost of the metal, and relative sluggishness (for the indium). For example, Othman et al. (2012) report on the synthesis of isotactic stereo-diblock PLA of some precision employing a living catalyst, in which two "overnight" periods were required for full monomer consumption.

Additional Background art includes Wheaton et al. *Dalton Trans.* 2009, 4832-4846; Chisholm et al. *J. Am. Chem. Soc.* 2000, 122, 11845-11854; Chamberlain et al. *J. Am. Chem. Soc.* 2001, 123, 3229-3238; Chen et al. *Macromolecules* 2006, 39, 3745-3752; Darensbourg et al. *Inorg. Chem.* 2010, 49, 2360-2371; and Yu et al. *Organometallics*, 2013, 32, 3262-3268, which teach catalysts for lactide ring opening polymerization in which zinc is embedded in various ligand environments. While a few of these catalysts exhibit high activities, they traditionally tend to be either non-stereoselective or heteroselective.

Isoselective polymerization of rac-LA has been reported, for example, by Wang and Ma, *Chem. Commun.* 2013, 49, 8686-8688; Wang et al. *Macromolecules* 2014, 47, 7750-7764; Abbina and Du, *ACS Macro. Lett.* 2014, 3, 689-692; Mou et al. *Chem. Commun.* 2014, 50, 11411-11414; Honrado et al. *Organometallics*, 2015, 34, 3196-3208.

A zinc catalyst obtainable using a pre-catalyst featuring an ethylzinc bound to a tridentate monoanionic diamine-monophenolate {ONN} ligand, the structure of which is presented below, was shown to exhibit very high activity in lactide ROP, upon addition of ethyl alcohol, consuming 500 equivalents of rac-LA in 5 minute at room temperature [Williams et al. *J. Am. Chem. Soc.* 2003, 125, 11350-11359]. However, the PLA obtained using this catalyst was atactic. This catalyst was found to be dinuclear in the solid state and mononuclear in solution.

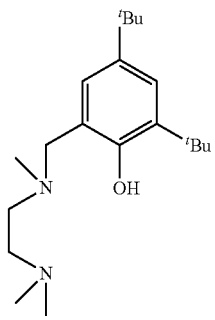 [SMILES: CN(C)CCN(C)Cc1cc(C(C)(C)C)cc(C(C)(C)C)c1O]

tridentate {ONN}-H ligand precursor.

A later attempt to induce stereoselectivity by employing a chiral diaminocyclohexane-based ligand led to a robust zinc complex, whose ethyl group could not be readily replaced with an active alkoxo group [Labourdette et al. *Organometallics*, 2009, 28, 1309-1319].

Recently, a tetradentate monoanionic ligand featuring a chiral bipyrrolidine core and phenolate and pyridine peripheral donors was described in the context of iron electrochemistry [Chiang et al. *Inorg. Chem.* 2014, 53, 5810-5819].

Additional background art includes Rosen et al. *Chem. Eur. J.* 2016, 22, 11533-11536; Fliedel et al. *Dalton Trans.* 44, 12376 (2015); Ajellal et al. *Dalton Trans.* 39, 8363 (2010); Carpentier, J.-F., & Sarazin, Y. *Top. Organomet. Chem.* 45, 141 (2013); Tschan et al., *Dalton Trans.*, 2014, 43, 4550; Rosen et al., *J. Am. Chem. Soc.* 2016, 138, 12041-12044; and Rosen et al., DOI: 10.1039/c7sc01514c.

SUMMARY OF THE INVENTION

Block copolymers are expected to play important roles in future applications such as biomedical applications, particularly block polyester copolymers.

The present inventors have now designed and successfully practiced a methodology for obtaining block copolymers including diblocks, triblocks, and the unprecedented tetrablocks and hexablocks and higher block polyester copolymers. The designed methodology employs a recently disclosed group of Mg/Zn/Ca-based organometallic complexes featuring sequential or divergent {ONNN} ligand, along with a hydroxy-containing initiator, and is effected by the sequential addition of different types of cyclic ester monomers which differ from one another by stereoconfiguration and/or chemical composition, such as, for example, different diastereoisomers of lactide, optionally in combination with a lactone (e.g., F-caprolactone). These catalyst systems exhibit an exceptional combination of high activity and well-behaved character leading to active and living catalysts.

The production of novel tailor-made polymeric materials with possible biomedical and other applications is described. Some embodiments of the present invention relate to processes of preparing block copolymers of cyclic esters, in particular stereoblock copolymers of chiral cyclic esters such as lactides, and block copolymers of lactones and lactides, and to block polyester copolymers featuring precise controllability of their structural features and properties.

Some embodiments of the present invention relate to novel magnesium complexes featuring divergent {ONNN} ligands, to novel ligand precursors usable in preparing such complexes and to processes of preparing polymers of cyclic esters and block copolymers of cyclic esters, including stereoblocks of chiral cyclic esters, utilizing these complexes.

According to an aspect of some embodiments of the present invention there is provided a process of preparing a block copolymer comprising a plurality of units, at least two of the units independently comprise a plurality of polymerized monomers of a cyclic ester, at least one unit of the at least two units comprises a plurality of polymerized monomers of a first cyclic ester, and at least one another unit of the at least two units comprises a plurality of polymerized monomers of a second cyclic ester, the second cyclic ester differing from the first cyclic ester by a stereoconfiguration and/or a chemical composition, the process comprising:

sequentially contacting a plurality of monomers of the first cyclic ester and a plurality of monomers of the second cyclic ester with a catalyst system comprising an initiator and a {ONNN}M-X complex, wherein M is a divalent metal and X is a monoanionic ligand, to thereby sequentially effect a ring opening polymerization of the first cyclic ester and of the second cyclic ester.

According to some of any of the embodiments described herein, the block copolymer further comprises at least one additional unit comprising a plurality of polymerized monomers of a third cyclic ester, the third cyclic ester differing from each of the first cyclic ester and the second cyclic ester by a stereoconfiguration and/or a chemical composition, the process comprising:

sequentially contacting a plurality of monomers of the first cyclic ester, a plurality of monomers of the second cyclic ester, and a plurality of monomers of the third cyclic ester, at any order, with a catalyst system comprising an initiator and a {ONNN}M-X complex, wherein M is a divalent metal and X is a monoanionic ligand, to thereby sequentially effect a ring opening polymerization of the first cyclic ester, of the second cyclic ester and of the third cyclic ester, ay any of the order.

According to some of any of the embodiments described herein, at least one pair of adjacent units comprises one unit comprising a plurality of polymerized monomers of the first cyclic ester, and one unit comprising a plurality of polymerized monomers of the second cyclic ester, such that the block copolymer comprises at least two adjacent units differing from one another by a stereoconfiguration and/or a chemical composition.

According to some of any of the embodiments described herein, the block copolymer comprises from 2 to 10 units.

According to some of any of the embodiments described herein, at least two units in the plurality of units differ from one another by a number of the polymerized monomers.

According to some of any of the embodiments described herein, the at least two units which differ from one another by a number of polymerized monomers form a pair of adjacent units in the block copolymer.

According to some of any of the embodiments described herein, at least 90%, or at least 95% or at least 96% or at least 98% or at least 99% of polymerized monomers in each of the units feature the same stereoconfiguration and/or chemical composition.

According to some of any of the embodiments described herein, the block copolymer is a diblock copolymer, and wherein the diblock copolymer is obtained within less than 2 hours, or less than one hour.

According to some of any of the embodiments described herein, the ring-opening polymerization is a living polymerization or an immortal polymerization.

According to some of any of the embodiments described herein, the sequential contacting comprises contacting a plurality of monomers of the first cyclic ester with the catalyst system for a first time period; and, subsequent to the first time period, contacting a plurality of monomers of second cyclic ester for a second time period, and, optionally, subsequent to the second time period, contacting an additional plurality of monomers, being either of the first cyclic ester or of a third cyclic ester which differs from the first and second cyclic esters by a stereoconfiguration and/or chemical composition, for a third time period; and, further optionally, subsequent to the third time period, contacting a plurality of monomers of a second cyclic ester or of a cyclic ester different from the third cyclic ester or the first cyclic ester, for a fourth time period, and, further optionally, sequentially contacting a plurality of monomers of different cyclic esters, for additional time periods, according to a desirable number of units in the block copolymer and a desirable number of different blocks in the block copolymer.

According to some of any of the embodiments described herein, each of the first, second, and optionally third, fourth and additional, time periods independently ranges from 1 minute to 6 hours, or from 1 minute to 3 hours, or from 1 minute to 2 hours, or from 1 minute to one hour, or from 1 minute to 30 minutes, or from 5 minutes to 30 minutes or from 5 minutes to 20 minutes.

According to some of any of the embodiments described herein, the block copolymer is a stereoblock copolymer comprising at least one unit of polymerized monomers of the first cyclic ester and at least one unit of polymerized monomers of a second cyclic ester, the first cyclic ester featuring a first stereoconfiguration and the second cyclic ester featuring a second stereoconfiguration, the first and the second stereoconfigurations being different from one another.

According to some of any of the embodiments described herein, the process comprises sequentially contacting a plurality of monomers of the first cyclic ester featuring the first stereoconfiguration and a plurality of monomers of the second cyclic ester featuring the second stereoconfiguration with the catalyst system.

According to some of any of the embodiments described herein, at least 90%, or at least 95% or at least 96% or at least 98% or at least 99% of the polymerized monomers in each of the units feature the same stereoconfiguration.

According to some of any of the embodiments described herein, a chemical composition of the first cyclic ester and the second cyclic ester is the same.

According to some of any of the embodiments described herein, at least one of the first and second cyclic esters is a lactide.

According to some of any of the embodiments described herein, the lactide is selected from a homochiral lactide, a racemic lactide and a meso lactide.

According to some of any of the embodiments described herein, at least one of the first and second cyclic esters is a lactone, for example, a caprolactone such as δ-caprolactone.

According to an aspect of some embodiments of the present invention there is provided a process of preparing a block copolymer comprising a plurality of units, at least two adjacent units in the plurality of units independently comprise a plurality of polymerized monomers of a cyclic ester, at least one unit of the at least two adjacent units comprises a plurality of polymerized monomers of a first cyclic ester, and at least one another unit of the at least two adjacent units comprises a plurality of polymerized monomers of a second cyclic ester, the second cyclic ester differing from the first cyclic ester by a stereoconfiguration and/or a chemical composition, the process comprising sequentially subjecting a plurality of monomers of the first cyclic ester and the second cyclic ester to a condition for effecting ring-opening polymerization of the cyclic esters.

According to some of any of the embodiments described herein, the condition for effecting the ring opening polymerization comprises contacting the plurality of monomers of the cyclic ester with a catalyst system that promotes the ring opening polymerization.

According to some of any of the embodiments described herein, the catalyst system comprises an initiator and a {ONNN}M-X complex, wherein M is a divalent metal and X is a monoanionic ligand.

According to some of any of the embodiments described herein, the initiator comprises at least one hydroxy group.

According to some of any of the embodiments described herein, the initiator comprises a plurality of hydroxy groups.

According to some of any of the embodiments described herein, a mol ratio of the organometallic complex and the initiator ranges from 1:1 to 1:1000.

According to some of any of the embodiments described herein, the sequential contacting is at room temperature.

According to some of any of the embodiments described herein, the sequential contacting is in a solution.

According to some of any of the embodiments described herein, the process is a one-pot process.

According to some of any of the embodiments described herein, the organometallic complex is represented by Formula I:

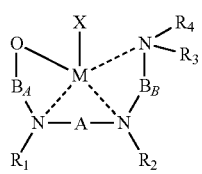

Formula I wherein:
the dashed line represents a coordinative bond;
M is the divalent metal;
X is the monoanionic ligand as described herein in any of the respective embodiments;
A, $B_A$ and $B_B$ are each independently a bridging moiety of 1 to 12 carbon atoms;
$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5 to 7-membered ring; and
$R_3$ and $R_4$ are each independently hydrogen, alkyl, cycloalkyl, aryl or alternatively, one or both of $R_3$ and $R_4$ form together with one or more carbon atoms in $B_2$, a heteroalicyclic or heteroaromatic, 5 to 7-membered ring.

According to some of any of the embodiments described herein, M is magnesium.

According to some of any of the embodiments described herein, at least one, or each, of the cyclic esters is a lactide, and wherein X is halo.

According to some of any of the embodiments described herein, at least one of the first and second cyclic ester is a lactone and wherein X is a substituted amine.

According to some of any of the embodiments described herein, the complex is represented by Formula IA:

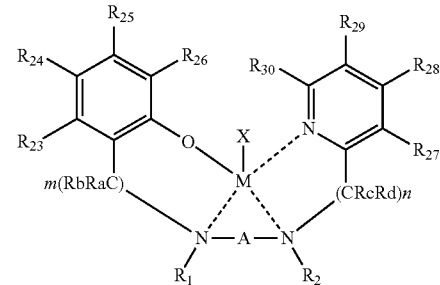

Formula IA wherein:
$R_{23}$-$R_{30}$ are each independently selected from the group consisting of hydrogen, alkyl, cycloalkyl, aryl, halo, alkoxy, aryloxy, trialkylsilyl, heteroalicyclic, heteroaryl, and amine.

According to an aspect of some embodiments of the present invention there is provided a block copolymer of a cyclic ester obtainable by the process as described herein in any of the respective embodiments and any combination thereof.

According to an aspect of some embodiments of the present invention there is provided a block copolymer of a cyclic ester comprising a plurality of units, at least two of the units independently comprise a plurality of polymerized monomers of a cyclic ester, wherein one of the at least two units comprises a plurality of polymerized monomers of a first cyclic ester and a another one of the at least two units comprises a plurality of polymerized monomers of a second cyclic ester, the first cyclic ester and the second cyclic ester differ from one another by a chemical composition and/or a stereoconfiguration, wherein:
at least 90%, or at least 95% or at least 96% or at least 98% or at least 99% of the polymerized monomers in each of the at least two units are identical to one another; and/or
a number of polymerized monomers in at least two of the plurality of units is different; and/or
the block copolymer comprises at least 3, or at least 4 units of polymerized monomers of the cyclic ester.

According to some of any of the embodiments described herein, the at least two units independently comprising a plurality of polymerized monomers of the first cyclic ester and of the second cyclic ester are adjacent units.

According to some of any of the embodiments described herein, the cyclic ester comprises at least one stereocenter and wherein at least two of the units differ from one another by a stereoconfiguration of the cyclic ester.

According to some of any of the embodiments described herein, the cyclic ester is lactide.

According to some of any of the embodiments described herein, each of the units comprises polymerized monomers featuring a polymeric configuration selected from a linear polymeric chain and branched polymeric chains.

According to some of any of the embodiments described herein, the block copolymer characterized by a polydispersity (Mw/Mn) lower than 1.5, or lower than 1.2.

According to some of any of the embodiments described herein, the block copolymer is characterized by a Tm of at least 200° C.

According to some of any of the embodiments described herein, the block copolymer is characterized by a substantial heat of melting of at least 40 J/g, or 50 J/g, or 60 J/g, or 70 J/g, or 80 J/g.

According to an aspect of some embodiments of the present invention there is provided a process of ring opening polymerization of a cyclic ester, the process comprising contacting a plurality of monomers of the cyclic ester with a catalyst system comprising an organometallic magnesium complex, the organometallic magnesium complex comprising a Mg—X unit and a divergent {ONNN} ligand in coordination with the Mg—X.

According to some of any of the embodiments described herein, the magnesium complex is represented by Formula IIA or IIB, as described herein in any of the respective embodiments.

According to some of any of the embodiments described herein, the complex is represented by Formula III, as described herein in any of the respective embodiments.

According to some of any of the embodiments described herein, the polymer is a block copolymer comprising a plurality of units, at least two of the units independently comprise a plurality of polymerized monomers of a cyclic ester, at least one unit of the at least two units comprises a plurality of polymerized monomers of a first cyclic ester, and at least one another unit of the at least two units comprises a plurality of polymerized monomers of a second cyclic ester, the second cyclic ester differing from the first cyclic ester by a stereoconfiguration and/or a chemical composition, the process comprising:

sequentially contacting a plurality of monomers of the first cyclic ester and a plurality of monomers of the second cyclic ester with the catalyst system comprising an initiator and an organometallic magnesium complex comprising a Mg—X unit and a divergent {ONNN} ligand in coordination with the Mg—X, to thereby sequentially effect a ring opening polymerization of the first cyclic ester and of the second cyclic ester.

According to an aspect of some embodiments of the present invention there is provided an organometallic complex represented by Formula III or by Formula IIB, as described herein in any of the respective embodiments.

According to an aspect of some embodiments of the present invention there is provided a ligand precursor represented by Formula IV, as described herein in any of the respective embodiments.

Further according to embodiments of the present invention there are provided processes, block polyester copolymers, and catalyst systems essentially as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
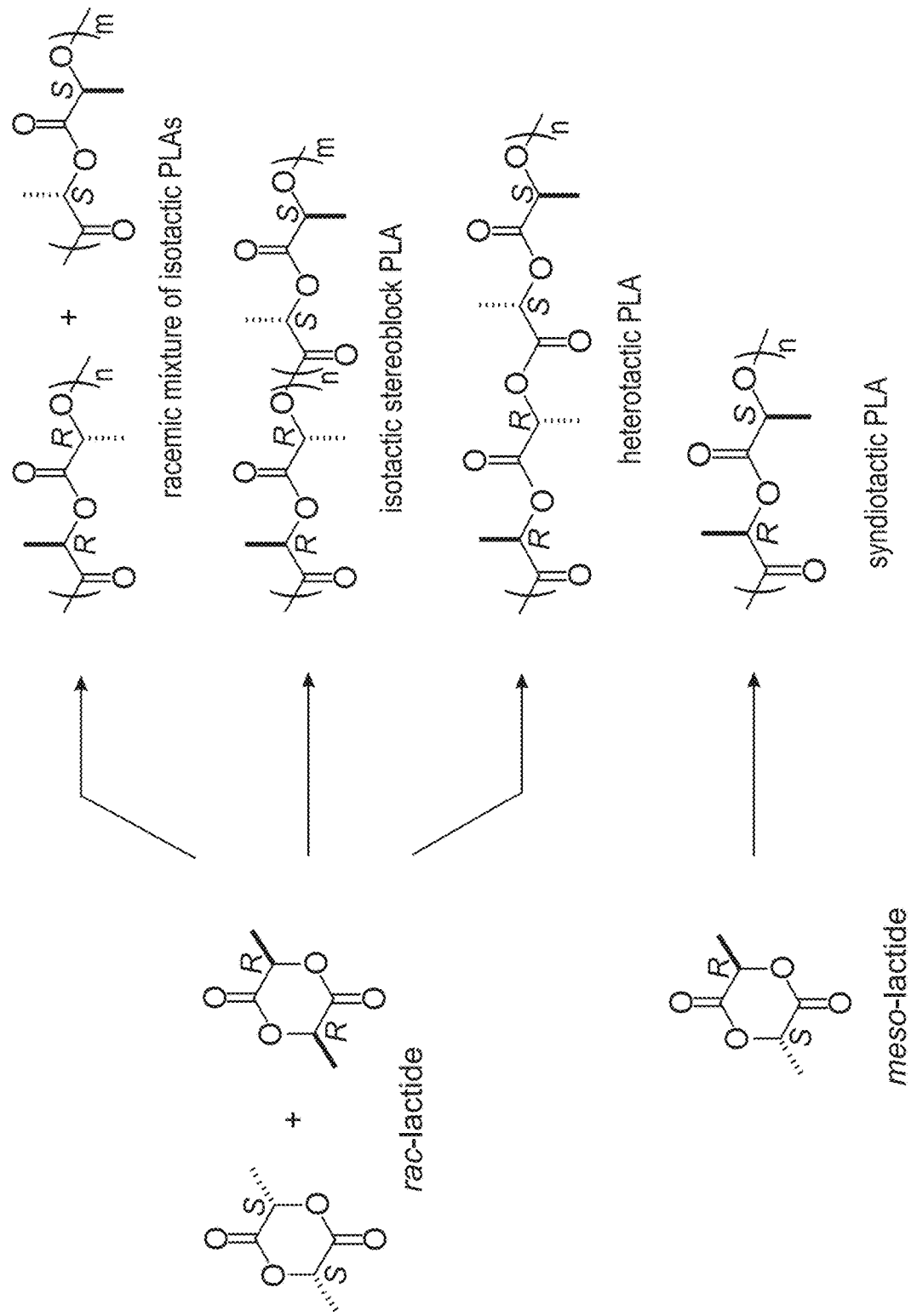
FIG. 1 (Background Art) presents a schematic illustration of ring opening polymerization of lactides and the PLAs featuring various tacticities afforded thereby.

The present invention, in some embodiments thereof, relates to chemistry and, more particularly, but not exclusively, to block polyester copolymers, including, but not limited to, stereoblcok polyester copolymers, featuring high precision, and to one-pot ring opening polymerization processes for preparing same.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As discussed hereinabove, the ability to manufacture polymeric materials having a 'tailor-made' structure is a key-step on the way to improving the properties of existing plastics, particularly biodegradable plastic materials derived from bio-renewable resources such as poly(lactic acid) (PLA), poly(F-caprolactone) (PCL) and other polyesters.

More advanced PLA generations are expected to include different types of lactide isomers assembled in an ordered (regioregular) fashion, and in particular block copolymers. In particular, isotactic stereoblock-PLA composed of covalently bound PDLA and PLLA blocks has been targeted.

Such tailor-made plastics require sophisticated catalysts, and, in the past 15 years, there has been an enormous effort to try and develop more advanced catalysts.

Some of the requirements of such catalysts are: high activities and turnover numbers leading to high molecular weight-polymers; living character or possibly immortal character (giving more than a single polymer chain for every catalytic center); low cost and low toxicity.

The most controlled manner of producing block copolymers is by employing living polymerization catalysis. In contrast to non-living polymerization which includes the steps of initiation, propagation (chain growth), and termination (with possible growing of a new chain), living polymerization is a process in which only the first two steps, i.e., initiation and propagation, take place. The catalyst is not involved in the termination processes. This has several outcomes: (i) all the monomers may be consumed in the process; (ii) if all the catalyst is activated, and if the propagation is not considerably faster than the initiation, then a narrow distribution of molecular weights of the polymeric chains is obtained, and the molecular weight of the polymeric chains can be designed from the ratio of monomer/catalyst or monomer/initiator employed; (iii) the copolymerization reaction can be resumed upon addition of a new batch of monomers without loss of number of active catalyst molecules; and (iv) block copolymers may be produced by employing different monomers in different batches.

The most direct strategy for producing block copolymers, and stereoblock-PLA or other stereoblock polyester copolymers in particular, would be the sequential addition of different monomers, e.g., different lactide enantiomers, to a truly-living polymerization catalyst, namely, a catalyst lacking a termination step.

Currently practiced methodologies for producing stereoblock polyester copolymers typically require many hours for completion, and are often insufficiently accurate.

As a result, to date, block copolymers of cyclic ester monomers such as lactides and/or lactones are very rare. Moreover, block copolymers, such as stereoblock copolymers, higher than diblock or triblock copolymers of cyclic esters, have not been described hitherto.

The present inventors have now devised a novel methodology for preparing block copolymers of cyclic esters (block polyester copolymers) in extremely short time periods, and in exceptional accuracy (precision). This methodology enables to obtain block polyester copolymers higher than triblock copolymers, including tetrablock, pentablock, hexablock, and even octablock copolymers, and higher. This methodology further enables exceptional controllability on the number of blocks, the length (number of repeating backbone units) of each block, and the number of polymeric chains in each block (e.g., number of branches in branched polymers).

In some embodiments, the designed methodology may be executed with catalysts based on biocompatible metals such as magnesium (Mg) and zinc (Zn).

According to an aspect of some embodiments of the present invention there are provided processes of preparing block copolymers of cyclic esters.

The Block Copolymers:

Herein, the phrase "block copolymer of a cyclic ester" is also referred to interchangeably as "block polyester copolymer", describes block copolymers comprised of two or more blocks, wherein at least two of these blocks comprise, each independently, a polyester homopolymer, wherein the polyester homopolymers in these at least two blocks differ from one another by their chemical composition and/or stereoconfiguration.

In some embodiments, each block that comprises a polyester homopolymer is comprised of polymerized monomers of a corresponding cyclic ester, and is also referred to herein as a unit in the block copolymer.

Each block is formed of a plurality of cyclic ester monomers which represent a plurality of repeating backbone units covalently attached to one another and forming the homopolymer block.

The term "block" is also referred to herein as "homopolymer block", "homopolyester block", "polyester block", "polyester unit", "unit" and "unit comprising polymerized monomers of a cyclic ester" (as indicated), and also as combinations of any of the foregoing, and is meant to encompass a unit in the block copolymer that is made of one type of polyester, that is, of polymerized monomers of one type of cyclic ester.

A block polyester copolymer can comprise two, three, four, five or more blocks, and at least two of these blocks are homopolyester blocks which differ from one another by the type (stereoconfiguration and/or chemical composition) of the monomers of the cyclic esters that are polymerized within the block, as described herein.

A block polyester copolymer can comprise two types of blocks (units), each independently comprising (or composed of) a plurality of polymerized monomers of a cyclic ester, at least one of these units comprises a plurality of polymerized monomers of a first cyclic ester, and at least one another unit of these units comprises a plurality of polymerized monomers of a second cyclic ester, the second cyclic ester differing from the first cyclic ester by a stereoconfiguration and/or a chemical composition, as defined herein.

A block polyester copolymer which comprises two types of blocks can comprise 2, 3, 4, 5, and more blocks (units), in an alternating order, such that in any pair of adjacent blocks (units), the units are made of polymerized monomers of a different cyclic ester.

A block polyester copolymer can comprise three or more types of blocks (units), each independently comprising (or composed of) a plurality of polymerized monomers of a cyclic ester, at least one of these units comprises a plurality of polymerized monomers of a first cyclic ester, and at least one another unit of these units comprises a plurality of polymerized monomers of a second cyclic ester, the second cyclic ester differing from the first cyclic ester by a stereoconfiguration and/or a chemical composition, as defined herein. Such a block copolymer can comprise in addition to the above-mentioned units of the first and second cyclic ester, units which are not polymerized monomers of a cyclic ester (e.g., are rather made of repeating backbone units of monomers which are not a cyclic ester). Alternatively, such a block copolymer can comprise, in addition to the above-mentioned units of the first and second cyclic ester, one or more types of blocks (units), each independently comprising (or composed of) a plurality of polymerized monomers of a third cyclic ester, and optionally of a fourth cyclic ester, while the third cyclic ester is different from the first, second and, if present, the fourth cyclic esters, and the fourth cyclic ester is different from the first, second and third cyclic esters.

Whenever there are more than two types of blocks (units) in the block polyester copolymer, these different blocks can be arranged in any other.

Non-limiting examples include:
-A-B-A-B-A-B-A-B-
-A-B-C-A-B-C-A-B-C-
-A-B-A-C-A-B-A-C-
-A-B-C-B-A-C-B-C-
-A-B-C-D-A-B-C-D-
-A-C-D-A-B-C-A-D-C-, Wherein A, B, C and D are each independently a different block, for example, A is a first type of block (a first unit) made of polymerized monomers of a cyclic ester of a first type (a first cyclic ester); B is a second type of block (a second unit) made of polymerized monomers of a cyclic ester of a second type (a second cyclic ester); C is a third type of block (a third unit) made of polymerized monomers of a cyclic ester of a third type (a third cyclic ester), or, alternatively, is a block made of polymerized monomers which are not a cyclic ester; and D is a fourth type of block (a fourth unit) made of polymerized monomers of a cyclic ester of a fourth type (a fourth cyclic ester), or, alternatively, is a block made of polymerized monomers which are not a cyclic ester and which different from C.

In some embodiments, the block copolymer is comprised of two types of blocks, for example, is comprised of a polymer sequence of Block-Block2-Block-Block2, wherein Block1 is a polyester of first chemical composition and/or stereoconfiguration and Block2 is a polyester of a second chemical composition and/or stereoconfiguration which is different from the first chemical composition and/or stereoconfiguration.

The copolymer, according to these embodiments, can be a diblock, triblock, tetrablock, etc.

In some embodiments, the block copolymer is comprised of three or more types of blocks, which can be sequenced in the block copolymer in any order, based on the sequence of subjecting the plurality of cyclic ester monomers forming each block to ring opening polymerization. The copolymer, according to these embodiments, can be a triblock, tetrablock, etc.

By "diblock", "triblock", "tetrablock", etc., the number of blocks is presented. These types of blocks in each of such block copolymers are at least two, regardless of the number of blocks.

When a block copolymer as described herein comprises two units, it is referred to as a diblock copolymer.

When a block copolymer as described herein comprises three units (two of which can the same or all three are different), it is referred to as tri-block copolymer.

When a block copolymer as described herein comprises four units (two or three of which can the same or all four are different), it is referred to as tetra-block copolymer, and so forth.

According to some of any of the embodiments described herein, the block copolymer comprises 2, 3, 4, 5, 6, 7, 8, 9, 10 or even more units.

According to an aspect of some embodiments of the present invention there is provided a block copolymer comprising a plurality of units, at least two of the plurality of units independently comprise a plurality of polymerized monomers of a cyclic ester, at least one unit of these at least two units comprises a plurality of polymerized monomers of a first cyclic ester, and at least one another unit of these at least two units comprises a plurality of polymerized monomers of a second cyclic ester, as described herein, the second cyclic ester differing from the first cyclic ester by a stereoconfiguration and/or a chemical composition, as described herein.

According to an aspect of some embodiments of the present invention there is provided a block copolymer comprising a plurality of units, at least two adjacent units in said plurality of units independently comprise a plurality of polymerized monomers of a cyclic ester, at least one unit of said at least two adjacent units comprises a plurality of polymerized monomers of a first cyclic ester, and at least one another unit of said at least two adjacent units comprises a plurality of polymerized monomers of a second cyclic ester, said second cyclic ester differing from said first cyclic ester by a stereoconfiguration and/or a chemical composition.

In some of any of the embodiments described herein, the block copolymer further comprises at least one additional unit comprising a plurality of polymerized monomers of a third cyclic ester, the third cyclic ester differing from each of the first cyclic ester and the second cyclic ester by a stereoconfiguration and/or a chemical composition. In some embodiments, the additional unit is adjacent to one and/or both of the at least two adjacent units described hereinabove.

In some of any of the embodiments described herein, the block copolymer comprises from 2 to 10 units, and wherein at least one pair of adjacent units comprises one unit comprising a plurality of polymerized monomers of said first cyclic ester, and one unit comprising a plurality of polymerized monomers of said second cyclic ester, such that the block copolymer comprises at least two adjacent units differing from one another by a stereoconfiguration and/or a chemical composition.

According to some of any of the embodiments described herein, the polymerized monomers composing the units in the at least one pair of (e.g., adjacent) units differ from one another by a number of polymerized monomers (backbone units) (e.g., a length of the block). That is, for example, in a diblock copolymer, each block is comprised of a different number of polymerized monomers (backbone units) (a different number of polymerized monomers composing each of the units). In another, non-limiting example, in a triblock copolymer, first block is of N number of backbone units (polymerized monomers), second block is of M number of backbone units (polymerized monomers) and third block is of L number of backbone units (polymerized monomers), wherein either N≠M≠L, or at least N≠M, or M≠L, or N≠L.

In some of any of the embodiments described herein, at least 90%, or at least 95% or at least 96% or at least 98% or at least 99% of backbone units (polymerized monomers), or each of the backbone units (polymerized monomers), in each of the units (blocks) are identical to one another (feature the same chemical composition and/or stereoconfiguration).

The term "cyclic ester" as used herein describes a —C(=O)—O—Rx in which Rx is a hydrocarbon chain (e.g., lower, medium or higher alkyl, optionally substituted), as defined herein, optionally interrupted by one or more heteroatoms or moieties as defined herein, and one carbon atom of the hydrocarbon chain (e.g., of an alkyl) is linked to the carbon atom of the carboxylate to form a ring.

In some embodiments, a cyclic ester can be represented by Formula V:

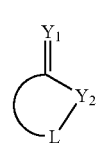

Formula V wherein:

$Y_1$ is selected from oxygen, sulfur and imine (=NR'), preferably from oxygen and sulfur, and is preferably oxygen;

$Y_2$ is selected from oxygen, sulfur and —NR', preferably from oxygen and sulfur, and is preferably oxygen; and L is a hydrocarbon chain, for example, a hydrocarbon chain which comprises one or more alkylene chains, each optionally being independently substituted or unsubstituted, and which can optionally be interrupted therebetween by one or more moieties such as oxygen atom, sulfur atom, amine, silyl, carbonyl, amide, carboxy (—C(=O)—O—), thiocarboxy, thiocarbonyl, and the like.

Each alkylene chain can be of from 1 to 30 carbon atoms, preferably from 1 to 20 carbon atoms, or from 1 to 15 carbon atoms, or from 1 to 10 carbon atoms.

In some of any of the embodiments described herein, the cyclic ester comprises two or more alkylene chains, which are interrupted therebetween, wherein at least two alkylene chains are interrupted therebetween by a carboxy group. Such cyclic esters are also referred to herein and in the art as "cyclic diesters".

In some of any of the embodiments described herein, the one or more alkylene chain(s) is/are unsubstituted.

In some of any of the embodiments described herein, at least one of $Y_1$ and $Y_2$ is oxygen.

In some of any of the embodiments described herein, each of $Y_1$ and $Y_2$ is oxygen.

In some of any of the embodiments described herein, L is an alkylene chain, non-interrupted. Such cyclic esters are also referred to herein and in the art as "lactone".

When $Y_2$ is —NR', the cyclic ester is a lactame.

In some of any of the embodiments described herein, L comprises two alkylene chains, interrupted by a carboxy group, whereby the two alkylene chains are identical to one another. Such a cyclic diester can also be regarded as a di-lactone of two molecules of a 2-hydroxycarboxylic acid, and is also referred to in the art as lactide.

While the term "lactide" generally describes a dilactone of any 2-hydroxycarboxylic acid, herein and in the art, this term typically also refers to a cyclic diester (di-lactone) of lactic acid (2-hydroxypropionic acid), as shown, for example, in Scheme 1 hereinabove.

Cyclic esters usable in the context of the present embodiments include substituted and unsubstituted lactones such as, for example, caprolactones and lactides, although any other cyclic esters are contemplated, for example, 6-valerolactone, y-butyrolactone, F-caprolactone, o-pentadecalactone, cyclopentadecanone, 16-hexadecanolide, oxacyclotridecan-2-one.

In some of any of the embodiments described herein, the cyclic ester is lactide, that is, a di-lactone of lactic acid (2-hydroxypropionic acid).

In some of any of the embodiments described herein, the cyclic ester is a lactone, for example, a caprolactone such as 8-caprolactone.

In some of any of the embodiments described herein, the cyclic ester has a chiral center.

Herein a "chiral cyclic ester" or a "cyclic ester having a chiral center", typically describes a cyclic ester or a cyclic diester as defined herein, in which one or more carbon atoms in one or more of the alkylene chains is substituted and thereby form a chiral center.

Whenever these phrases are used, the cyclic ester can be one enantiomer, one diastereomer, a meso form, or a racemic mixture, unless otherwise indicated.

In some of these embodiments, the cyclic ester is a racemic cyclic ester.

In some of any of the embodiments described herein, the cyclic ester is lactide and the lactide is a homochiral lactide or a racemic lactide or a meso lactide.

In some of any of the embodiments described herein, the lactide is a racemic lactide.

Herein throughout, the term "chemical composition" refers to the chemical structure of the cyclic ester, that is, the type of atoms and their 2D arrangement.

Herein throughout, the term "stereoconfiguration" refers to the spatial arrangement of the atoms in the cyclic ester, and thus refers to cyclic ester monomers featuring one or more chiral centers. According to some embodiments, the polymerized monomers feature a stereoconfiguration according to the stereoconfiguration of the chiral center(s).

For example, the cyclic monomer can be an enantiomer, and the polymerized monomers feature an isotactic configuration of the enantiomer. Thus, if a first and a second cyclic ester differ from one another by being different enantiomers, a unit comprising polymerized monomers of the first cyclic ester exhibits an isotactic stereoconfiguration of this enantiomer, and a unit comprising polymerized monomers of the second cyclic ester exhibits an isotactic stereoconfiguration of this enantiomer.

For example, the cyclic monomer can be a diastereoisomer, and the polymerized monomers feature an isotactic configuration of the diasteroisomer. Thus, if a first and a second cyclic ester differ from one another by being different diastereomers, a unit comprising polymerized monomers of the first cyclic ester exhibits an isotactic stereoconfiguration of this diastereomer, and a unit comprising polymerized monomers of the second cyclic ester exhibits an isotactic stereoconfiguration of this diastereomer.

In another example, a first cyclic ester is an enantiomer or a diastereomer and a second cyclic ester is a racemic mixture, a unit comprising polymerized monomers of the first cyclic ester exhibits an isotactic stereoconfiguration of the enantiomer or diastereomer, and a unit comprising polymerized monomers of the second cyclic ester exhibits a racemic mixture of the two isotactic stereoconfigurations of the enantiomer or diastereomer. A block comprised of such racemic cyclic ester can be heterotactic, isotactically-inclined, gradient isotactic or even atactic.

Block polyester copolymers featuring at least two units in which the first and second cyclic esters differ in their stereoconfiguration are also referred to herein as "stereoblocks".

According to an aspect of some embodiments of the present invention there is provided a block polyester copolymer as described herein which is stereoblock copolymer, comprises a plurality (e.g., from 2 to 10) of units of polymerized monomers of a cyclic ester, wherein at least two units (e.g., at least one pair of two adjacent units) comprises one unit comprising a plurality of polymerized monomers of said first cyclic ester featuring a first stereoconfiguration and one unit comprising a plurality of polymerized monomers of said cyclic ester featuring a second stereoconfiguration, as described herein.

In some of any of the embodiments described herein, the polymerized monomers composing the units in at least two units in the copolymer (e.g., in at least one pair of (e.g., adjacent) units, differ from one another by a stereoconfiguration.

In some of the embodiments of a stereoblock copolymer as described herein, the chemical composition of the cyclic ester is the same, that is, the cyclic ester is the same and the first and second cyclic esters differ from one another only by their stereoconfiguration.

In some of any of the embodiments described herein for stereoblocks, at least 90%, or at least 95% or at least 96% or at least 98% or at least 99% of said polymerized monomers in each units comprising same feature the same stereoconfiguration.

In some of any of the embodiments described herein, the block copolymer is a stereoblock copolymer, as described herein, in which two units in the block copolymer differ from one another by stereoconfiguration.

In exemplary embodiments, one or more of the cyclic ester monomers is a lactide, as described herein.

In exemplary embodiments, one type of cyclic ester monomers (a first cyclic ester) is a lactide having one stereoconfiguration and another type of cyclic ester monomers (a second cyclic ester) is a lactide having another stereoconfiguration, and/or is another cyclic ester (e.g., a glycolide or a lactone).

In exemplary embodiments, the block copolymer is made of two or more types of lactides, which differ from one another in stereoconfiguration, and optionally, one type of monomers comprises glycolide.

In exemplary embodiments, the block copolymer is made of two or more types of lactides, which differ from one another in stereoconfiguration, and optionally, one type of monomers comprises a lactone.

In exemplary embodiments, the block copolymer is made of one or more types of lactides, and one type of monomers of a lactone.

In exemplary embodiments, the lactone is a caprolactone.

Exemplary such block copolymers include, but are not limited to: PLLA-PDLA, PDLA-PLLA-PDLA, PDLA-PLLA-PDLA-PLLA, and so forth, PLLA-PDLA-glycolide; PLLA-glycolide-PLDA-glycolide; PLLA-PDLA-glycolide-PLLA-PDLA-glycolide; PLLA/PDLA-glycolide-PDLA/PLLA; PLLA/PDLA-glycolide-PDLA/PLLA-glycolide, PLLA-PDLA-PCL, PLLA-PDLA-PCL-PDLA-PLLA, PCL-PLLA-PDLA-glycolide and any other combinations of two or all of PLLA, PDLA, glycolide and polycaprolactone.

In some of any of the embodiments described herein, the block copolymers of a cyclic ester are obtainable by a process as described herein in any of the respective embodiments.

In some of any of the embodiments described herein, there is provided a block copolymer of a cyclic ester comprising a plurality of units, at least two of said units independently comprise a plurality of polymerized monomers of a cyclic ester, wherein one of said at least two units comprises a plurality of polymerized monomers of a first cyclic ester and a another one of said at least two units comprises a plurality of polymerized monomers of a second cyclic ester, said first cyclic ester and said second cyclic ester differ from one another by a chemical composition and/or a stereoconfiguration, wherein:

at least 90%, or at least 95% or at least 96% or at least 98% or at least 99% of the polymerized monomers (backbone units) in each of the units are identical to one another, as described herein; and/or a number of the polymerized monomers in at least two of the units is different in each of the at least two units; and/or the block copolymer comprises at least 3, or at least 4 units of polymerized monomers of the cyclic ester.

In some of any of the embodiments described herein, there is provided a block copolymer of a cyclic ester comprising at least two units of polymerized monomers of a cyclic ester, wherein at least one, or each, pair of adjacent units comprises a first unit of polymerized monomers of a first type and a second unit of polymerized monomers of a second type, the monomers of the second type differing from the monomers of the first type by a chemical composition and/or a stereoconfiguration of the cyclic ester, wherein:

at least 90%, or at least 95% or at least 96% or at least 98% or at least 99% of the polymerized monomers (backbone units) in each of the units are identical to one another; and/or a number of the polymerized monomers in at least two of the units is different in each of the at least two units; and/or the block copolymer comprises at least 3, or at least 4 units of polymerized monomers of the cyclic ester.

In some of any of the embodiments described herein, the cyclic ester comprises at least one stereocenter and wherein at least two of the units differ from one another by a stereoconfiguration of the cyclic ester.

In some of any of the embodiments described herein, the cyclic ester is lactide.

In some of any of the embodiments described herein, the cyclic ester is F-caprolactone.

In some of any of the embodiments described herein, each of the units independently comprises polymerized monomers featuring a polymeric configuration selected from a linear polymeric chain and branched polymeric chains, as described herein in further detail regarding polyalcohols as initiators.

In some of any of the embodiments described herein, the block copolymer is characterized by a polydispersity (Mw/Mn) lower than 1.5, or lower than 1.2.

In some of any of the embodiments described herein, the block copolymer is characterized by characterized by a Tm of at least 200° C.

In some of any of the embodiments described herein, the block copolymer is characterized by a substantial heat of melting of at least 40 J/g, or 50 J/g, or 60 J/g, or 70 J/g, or 80 J/g.

Any of the block copolymers described herein are contemplated.

In some of any of the embodiments described herein, the block polyester copolymers described herein are obtainable by a ring opening polymerization as described herein, and is some embodiments, the ring opening polymerization is an isoselective polymerization (e.g., in case the cyclic ester is chiral). By "isoselective polymerization", it is meant a stereo-controlled polymerization that provides at least one enchainment of an identical enantiomer or diastereomer. Isoselective polymerization can provide a polymer comprising backbone units that feature generally (e.g., at least 60%, or at least 70%, or at least 80%, or more) the same stereoconfiguration, that is a single enchainment of an identical enantiomer or diastereomer, or a mixture of two such polymers (for example, one of an R enantiomer and the other of an S enantiomer).

Isoselective polymerization can be determined by the Pm of the obtained polymer.

Herein and in the art, Pm describes the tendency for a meso-enchainment (i.e. identical enantiomer enchainment) in polymerization of a cyclic ester having one or more chiral centers, which gives rise to isotactic polyester. A Pm value of 1.0 corresponds to perfectly isotactic polyester and a Pm value of 0.5 or lower corresponds to atactic PLA. A Pm value higher than 0.6, or higher than 0.7 is indicative of an isoselective polymerization.

In some of any of the embodiments described herein, one type of the cyclic esters is a racemic mixture of a chiral cyclic ester, and the block obtained therefrom is characterized by Pm of at least 0.6, or at least 0.7, or at least 0.8, while higher values are also contemplated.

According to an aspect of some embodiments of the present invention there is provided an article-of-manufacturing comprising a block polyester copolymer as described herein in any of the respective embodiments. Any articles commonly containing polylactides and/or polyglycolides and/or polycaprolactones are contemplated, as representative, non-limiting examples. Examples include, without limitation, commodity articles like food packaging, fibers, tubes, non-woven fabrics, etc. and articles employed in biomedical applications like resorbable coronary stents, matrices for controlled drug release, implants, sutures, etc.

The Process:

According to an aspect of some embodiments of the present invention there is provided a process of preparing any of the block polyester copolymers as described herein in any of the respective embodiments and any combination thereof.

According to some of any of the embodiments of the present invention the process comprises sequentially subjecting a plurality of monomers of a first cyclic ester, a second cyclic ester, and optionally a third, fourth and so forth cyclic esters, to conditions for effecting ring-opening polymerization of the cyclic ester. This results in sequential units in the block copolymer, each being a homopolymer formed of a plurality of cyclic ester monomers, which differ from one another, in each unit, by chemical composition and/or stereoconfiguration, according to the selected cyclic esters and the sequencing of subjecting same to the polymerization conditions.

According to some of any of the embodiments described herein, the sequentially subjecting comprises sequentially contacting a plurality of monomers of the cyclic ester composing each of the units of polymerized monomers with a catalyst system for effecting the ring opening polymerization.

According to some of any of the embodiments described herein, the sequential contacting comprises contacting a plurality of monomers of a first type (featuring a first stereoconfiguration and/or a first chemical composition; a first cyclic ester) with the catalyst system for a first time period; and, subsequent to the first time period, contacting a plurality of monomers of a second type (featuring a second stereoconfiguration and/or a second chemical composition; the second stereoconfiguration being different from the first stereoconfiguration and/or the second chemical composition being different from the first chemical composition; a second cyclic monomer), for a second time period, and, optionally, subsequent to the second time period, contacting an additional plurality of monomers, being either of the first type or of a third type (which differs from the first and second type by a chemical composition and/or stereoconfiguration), for a third time period; and, further optionally, subsequent to the third time period, contacting a plurality of monomers of a type different from the third type (e.g., either the second type or a fourth type), for a fourth time period, and, further optionally, repeating contacting plurality of monomers of the first, second, third, fourth or other type, for additional time periods, according to a desirable number of block types and a desirable number of units in the block copolymer.

According to some of any of the embodiments described herein, each of the time periods independently ranges from 1 minute to 6 hours, or from 1 minute to 3 hours, or from 1 minute to 2 hours, or from 1 minute to one hour, or from 1 minute to 30 minutes, or from 5 minutes to 30 minutes or from 5 minutes to 20 minutes, including any intermediate values and subranges therebetween.

According to some of any of the embodiments described herein, the sequential addition can be effected also within higher time intervals, in view of the living nature of the catalyst.

According to some of any of the embodiments described herein, the process is a one-pot process (such that the sequential subjecting comprises sequentially adding the plurality of monomers to a reaction vessel containing the conditions for effecting ROP (e.g., containing the catalyst system and optionally a solvent).

In exemplary embodiments, one type of cyclic ester monomers is a lactide, as described herein.

In exemplary embodiments, one type of cyclic ester monomers is a lactide having one stereoconfiguration and another type of cyclic ester monomers is a lactide having another stereoconfiguration, and/or is another cyclic ester (e.g., a glycolide).

In exemplary embodiments, the block copolymer is made of two or more types of lactide, which differ from one another in stereoconfiguration, and optionally, one type of monomers comprises glycolide.

In some of any of the embodiments described herein, the block copolymer is a diblock copolymer, and the diblock copolymer is obtained within less than 2 hours, or less than one hour.

In some of any of the embodiments described herein, the ring opening polymerization is effected by sequentially contacting a plurality of monomers of a first, second and so for the cyclic esters with a catalyst system for effecting ROP of the cyclic ester.

In some of any of the embodiments described herein, The catalyst system comprises an organometallic complex as described herein in any of the respective embodiments.

The organometallic complex as described herein in any of the respective embodiments is also referred to herein as a "catalyst" or, in some embodiments, as a "pre-catalyst", which is activated by a co-catalyst as described herein. In some of any of the embodiments described herein, the catalyst system further comprises a co-catalyst.

The "co-catalyst" described herein is also referred to herein and in the art as "initiator".

In some embodiments, the initiator is a hydroxy-containing compound.

The hydroxy-containing compound can feature one hydroxy group, and can be, for example, HO-Rk, wherein Rk is alkyl, alkaryl, cycloalkyl or aryl, each can optionally be substituted or unsubstituted, as described herein.

Exemplary such initiators include, without limitation, benzyl alcohol, and alkyl alcohols such as ethyl alcohol, methyl alcohol, 2-propyl alcohol, tert-butyl alcohol, monohydroxy terminated polyethylene glycol, and monohydroxy terminated pre-synthesized polymers.

The hydroxy-containing compound can feature two or more hydroxy groups, and such compounds are also referred to herein and in the art as polyhydroxy or polyalcohol compounds.

Exemplary such compounds include, but are not limited to, alkylene glycols (featuring 2 hydroxy groups, for example, ethylene glycol, propylene glycol, etc., as glycerols (featuring 3 hydroxy groups), higher linear saccharides, and polyhydroxy compounds such poly(ethylene glycol) or pentaerythritol.

The type of initiator, namely, the number of the hydroxy groups in the initiator determines the number of the polymeric chains in a block (unit) of polymerized cyclic ester monomers.

For example, linear block copolymers are obtained when monohydroxy initiator is employed. Two polymeryl chains are grown in parallel when a dihydroxy initiator is employed. Star-shapes and comb-shaped block copolymers are obtained while employing multihydroxy initiator with a respective distribution of the hydroxy groups.

In some embodiments, the initiator forms a part of the block copolymer, as the core from which the blocks are grown by the sequential formation of the homopolymers in each block.

A mol ratio of the cyclic ester and the initiator determines the number of backbone units in each polymeric chain.

Thus, the architecture of each unit (e.g., number and length of the polymeric chains in each block) can be determined or controlled as desired by using an initiator that provides for the desirable properties.

In some of any of the embodiments described herein, the catalyst system does not comprise a co-catalyst, and in some of these embodiments, the catalyst system consists of the organometallic complex. In some of these embodiments, M in Formula I or IA is magnesium (Mg). In some of these embodiments, X in Formula I or IA is halo (e.g., chloro). In some of these embodiments, X in Formula I or IA is a substituted amine, as described herein, for example, HMDS.

In some of any of the embodiments described herein, the sequential contacting is at room temperature.

In some of any of the embodiments described herein, the sequential contacting is in a solution (e.g., in an organic solvent). In some embodiments, the organic solvent is a polar solvent, for example, having a polarity index higher than 1, or higher than 2, or higher than 3, and in some embodiments, it is a polar aprotic solvent. In some embodiments, the organic solvent is devoid of heteroatoms that can coordinate the metal atom, such as oxygen and nitrogen.

Exemplary solvents include, but not limited to, dichloromethane (DCM), chlorobenzene, tetrahydrofuran (THF), diethylether, ethylene dichloride, toluene, pentane, and the like.

In some of any of the embodiments described herein, the sequential contacting is in a melt, that is, is devoid of a solvent and is performed at a temperature at which the cyclic esters are liquid, for example, at a temperature which is at least the melting temperature of the cyclic ester, or is higher than the melting temperature of the cyclic ester by, for example, 5, 10, 15, 20 or more ° C.

In some of any of the embodiments described herein, the sequential contacting is effected under inert environment.

By "inert environment" it is meant an environment that is substantially free of oxygen, carbon dioxide, water and/or any other substances that may chemically react with the organometallic complex or otherwise interfere in the polymerization reaction.

In some of any of the embodiments described herein, the sequential contacting is for a total time period that ranges from 1 second to 24 hours, or from 1 second to 12 hours, or from 1 second to 5 hours, or from 10 seconds to 5 hours, or from 30 seconds to 5 hours, or from 30 seconds to 3 hours, of from 30 seconds to 2 hours, including any intermediate values and subranges therebetween, and depending on the number of blocks in the block copolymer.

In some of any of the embodiments described herein, a mol ratio of the cyclic ester and the organometallic complex ranges from 10:1 to 100000:1, or from 100:1 to 100000:1, or from 100:1 to 10000:1, including any intermediate values and subranges therebetween.

In some of any of the embodiments described herein, a mol ratio of the organometallic complex and the co-catalyst (if present) ranges from 1000:1 to 1:1000, or from 100:1 to 1:100, or from 10:1 to 1:1000, or from 10:1 to 1:100, or from 10:1 to 1:50, or from 10:1 to 1:40 or from 10:1 to 1:30, or from 10:1 to 1:20 or from 10:1 to 1:10, or from 1:1 to 1:10, or from 1:1 to 1:8, or from 1:1 to 1:6, or from 1:1 to 1:5 or from 1:1 to 1:4, including any intermediate values and subranges therebetween.

In some of any of the embodiments described herein, the polymerization is a living polymerization.

By "living polymerization", as used herein, it is meant a form of chain growth polymerization where chain termination is very low, the molecular weight of the polymer is proportional to the conversion, and the molecular weight distribution, PDI (polydispersity index), is very narrow.

In some of any of the embodiments described herein, the polymerization is an immortal polymerization.

Immortal polymerization, as used herein, is a form of living chain growth polymerization where the number of polymer chains is higher than the number of catalyst molecules and all polymer chains can grow by the catalyst. For example, by employing a ratio of a co-catalyst to living catalyst higher than 1 the number of polymer chains will be higher than the number of catalyst molecules and identical to the number of co-catalyst molecules. As a result, immortal polymerization can afford polymers with a controlled molecular weight, while the number of polymer molecules is higher than the number of the catalyst molecules.

In some of any of the embodiments described herein, the process is effected while employing a catalyst system which comprises an initiator and a {ONNN}M-X organometallic complexes, wherein M is a divalent metal, as described herein, and X is a monoanionic ligand as described herein, in any of the respective embodiments and any combination thereof.

In some of any of the embodiments described herein, a mol ratio of the organometallic complex and the initiator ranges from 1:1 to 1:1000.

In some of any of the embodiments described herein, a mol ratio of the cyclic ester and the initiator determines the number of backbone units in each of the units of polymerized monomers of the cyclic ester.

In some of any of the embodiments described herein, a process as described herein in any of the respective embodiments is of preparing a stereoblock polyester copolymer as described herein in any of the respective embodiments.

In some of these embodiments, the process comprises:

sequentially contacting a plurality of monomers of the cyclic ester featuring the first stereoconfiguration and a plurality of monomers of the cyclic ester featuring the second stereoconfiguration with a catalyst system as described herein in any of the respective embodiments.

In some embodiments, the catalyst system comprises an initiator and a {ONNN}M-X complex, as described herein in any of the respective embodiments.

In some of any of the embodiments described herein, the sequential contacting comprises contacting the plurality of monomers featuring the first stereoconfiguration with the catalyst system for a first time period; and, subsequent to the first time period, contacting the plurality of monomers featuring the second stereoconfiguration for a second time period, and, optionally, subsequent to the second time period, contacting the plurality of monomers featuring the first stereoconfiguration with the catalyst system for a third time period; and, further optionally, subsequent to the third time period, contacting the plurality of monomers featuring the second stereoconfiguration for a fourth time period, and, further optionally, repeating each of the contacting for additional time periods, according to the number of units in the stereoblock copolymer.

In some of any of the embodiments described herein, each of the time periods independently ranges from 1 minute to 6 hours, or from 1 minute to 3 hours, or from 1 minute to 2 hours, or from 1 minute to 1 hour, or from 1 minute to 30 minutes, or from 5 minutes to 30 minutes or from 5 minutes to 20 minutes, including any intermediate values and subranges therebetween.

In some of any of the embodiments described herein, the process is a one-pot process (such that the sequential addition is performed by sequentially adding the plurality of monomers to a reaction vessel containing the catalyst system and optionally a solvent).

The Catalyst System:

In some of any of the embodiments described herein, the catalysts system comprises an organometallic complex comprising a tetradentate monoanionic {ONNN}-type ligand and a divalent metal.

In some of these embodiments, the tetradentate monoanionic {ONNN}-type ligand, also referred to herein simply as a {ONNN} ligand is a sequential {ONNN} as described herein in any of the respective embodiments, and as represented, for example, by Formula I or Formula IA herein.

In some of these embodiments, the {ONNN} ligand a divergent {ONNN} ligand as described herein in any of the respective embodiments, and as represented, for example, by Formulae IIA, IIB, and III herein. According to some of any of the embodiments of the present invention the organometallic complex features a sequential {ONNN} ligand is represented by Formula I:

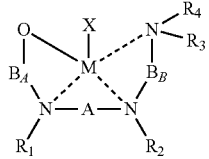

Formula I wherein:
the dashed line represents a coordinative bond;
M is a divalent metal;
X is a monoanionic ligand;
A, $B_A$ and $B_B$ are each independently a bridging moiety of 1 to 20 or of 1 to 12 carbon atoms;
$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5 to 7-membered ring; and
$R_3$ and $R_4$ are each independently hydrogen, alkyl, cycloalkyl, aryl or alternatively, one or both of $R_3$ and $R_4$ form together with one or more carbon atoms in $B_2$, a heteroalicyclic or heteroaromatic, 5 to 7-membered ring.

By "divalent metal" it is meant a metal that has a valency of 2, that is, is capable of forming two covalent bonds with 2 monovalent atoms. A "divalent metal" encompasses also metals which feature also higher valency.

In some of any of the embodiments described herein, M is zinc, magnesium, or calcium. Other divalent metals are also contemplated. In some preferred embodiments, M is zinc.

In some preferred embodiments, M is magnesium.

The monoanionic ligand, X, can be, as non-limiting examples, alkyl (substituted or unsubstituted), cycloalkyl (substituted or unsubstituted), aryl (substituted or unsubstituted), amide, alkoxy, thioalkoxy, aryloxy, thioalryloxy, halo or amine (substituted or unsubstituted), as these terms are defined herein.

In some of any of the embodiments described herein for Formula I, M is zinc, and X is alkyl, alkaryl, cycloalkyl or aryl. In some of these embodiments, X is alkyl, preferably an unsubstituted alkyl, for example, ethyl. Other alkyls, preferably lower alkyls, are contemplated.

In some of any of the embodiments described herein for Formula I, M is magnesium and X is halo, for example chloro.

In some of any of the embodiments described herein for Formula I, M is magnesium and X is amine. In some of these embodiments, the amine is a substituted amine (e.g., a secondary or tertiary amine), (e.g., a mono- or di-substituted amine) and in some embodiments the amine is a tertiary amine, substituted by two substituents, as defined hereinunder for R and R".

In exemplary embodiments of Formula I, M is magnesium and X is an amine substituted by one or two silyl groups, as defined herein. In some of these embodiments, the one or two silyl groups are independently substituted, for example, by one or more alkyl groups.

In exemplary embodiments of Formula I, M is magnesium and X is bis-trimethylsilyl-amino of the formula: $[(CH_3)_3Si]_2N-$, which is also referred to herein and in the art as HMDS.

It is noted that when an amine is bound to a metal atom, the resulting moiety is also referred to herein and in the art as "amide", that is, a M-NR'R" moiety as described herein is also referred to herein and in the art as a metal amide (e.g., Mg-HMDS amide.

In some embodiments, catalyst systems in which X is an amine or amide as defined herein are usable in polymerization of block copolymers in which one of the cyclic monomers is caprolactone.

In some embodiments, catalyst systems in which X is a halo as defined herein (e.g., chloro) are usable in polymerization of block copolymers in which the cyclic monomers are lactides.

Any one of the bridging moieties, A, $B_A$ and $B_B$, independently, can be a hydrocarbon chain of the indicated number of carbon atoms, as defined herein.

Herein, the term "hydrocarbon" describes an organic moiety that includes, as its basic skeleton, a chain of carbon atoms, also referred to herein as a backbone chain, substituted mainly by hydrogen atoms. The hydrocarbon can be saturated or unsaturated, be comprised of aliphatic, alicyclic and/or aromatic moieties, and can optionally be substituted by one or more substituents (other than hydrogen). A substituted hydrocarbon may have one or more substituents, whereby each substituent group can independently be, for example, alkyl, cycloalkyl, alkenyl, alkynyl, alkaryl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, silyl, carbamate, amide, and hydrazine, and any other substituents as described herein.

In some embodiments, the hydrocarbon is substituted by one or more amine-containing groups, such as amide, alkyl, alkaryl, aryl or cycloalkyl substituted by one or more amine groups, an amine-containing heteroalicyclic, and/or an amine-containing heteroaryl.

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein the hydrocarbon is not interrupted by any heteroatom, nor does it comprise heteroatoms in its backbone chain, and can be an alkylene chain, or be comprised of alkyls, cycloalkyls, aryls, alkenes and/or alkynes, covalently attached to one another in any order.

In some of any of the embodiments described herein, the hydrocarbon is an alkylene chain, which can be unsubstituted or substituted, as described herein.

In some of any of the embodiments described herein, the $B_A$ bridging moiety has a general Formula:

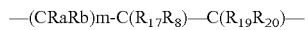
—(CRaRb)m-C($R_{17}R_8$)—C($R_{19}R_{20}$)— wherein:

m is an integer of from 1 to 6, or from 1 to 4, or from 1 to 2;

Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5-, 6- or 7-membered alicyclic, heteroalicyclic, aromatic or heteroaromatic ring with one or both Ra and Rb of an adjacent unit; and $R_{17}$-$R_{20}$ are each independently hydrogen, alkyl, cycloalkyl, aryl, heteroaryl, heteroalicyclic, hydroxyl, alkoxy, thiol, thioalkoxy, aryloxy, and amine, or, alternatively, two or more of $R_{17}$-$R_{20}$ form together a 5-, 6- or 7-membered alicyclic, heteroalicyclic, aromatic or heteroaromatic ring.

In some of these embodiments m is 1.

In some of any of the embodiments of $B_A$ of the above formula, Ra and Rb are each hydrogen.

In some of any of the embodiments of $B_A$ of the above formula, $R_{17}$-$R_{20}$ form together a substituted or unsubstituted, preferably 6-membered, aromatic ring.

In some of any of the embodiments of $B_A$ of the above formula, $R_{17}$-$R_{20}$ form together with the oxygen attached to $B_A$ a substituted or unsubstituted phenolate group.

In some of any of the embodiments described herein, the $B_B$ bridging moiety has a general Formula:

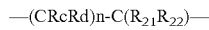
—(CRcRd)n-C($R_{21}R_{22}$)— wherein:

n is an integer of from 1 to 6, or from 1 to 4, or from 1 to 2;

Rc and Rd are each independently hydrogen, alkyl, cycloalkyl, alkaryl, aryl, heteroaryl, heteroalicyclic, hydroxyl, alkoxy, thiol, thioalkoxy, aryloxy, and amine, wherein when n is other than 1, Rc and Rd in each (CRcRd) unit can be the same or different, and one or both Rc and Rd in one unit can form a 5-, 6- or 7-membered alicyclic, heteroalicyclic, aromatic or heteroaromatic ring with one or both Re and Rd of an adjacent unit; and $R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_3$, $R_4$, $R_{21}$ and $R_{22}$ form together a 5, 6- or 7-membered heteroalicyclic or heteroaromatic ring (which includes, as a heteroatom, at least the nitrogen to which $B_B$ is attached, thus forming a nitrogen-containing heteroalicyclic or heteroaryl, as described herein).

In some of any of these embodiments, n is 1.

In some of any of these embodiments, Rc and Rd are each hydrogen.

In some of any of these embodiments, $R_3$, $R_4$, $R_{21}$ and $R_{22}$ form together a substituted or unsubstituted, preferably 6-membered, heteroaromatic ring, for example, a nitrogen-containing hereteroaryl, as described herein. In some of these embodiments, the heteroaryl is pyridine, which is connected to (CRcRd)n at the ortho position. Other heteroaryls, or heteroalicyclics, and other attachment positions are also contemplated.

In some of any of the embodiments described herein, the complex is represented by Formula IA:

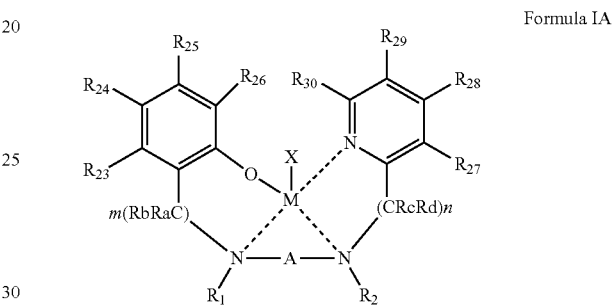

Formula IA wherein M, X, A, $R_1$, $R_2$, n, m, and Ra-Rd, are as defined herein in any of the respective embodiments, and $R_{23}$-$R_{30}$ are each independently selected from the group consisting of hydrogen, alkyl, cycloalkyl, alkaryl, aryl, halo, alkoxy, aryloxy, silyl (e.g., trialkylsilyl), heteroalicyclic, heteroaryl, and amine, and any of the other substituents described herein.

In some of any of the embodiments pertaining to Formula IA, at least one of $R_{23}$-$R_{26}$ is alkyl.

In some of any of the embodiments pertaining to Formula IA, at least one of $R_{24}$ and $R_{26}$ is alkyl.

In some of any of the embodiments pertaining to Formula IA, the alkyl is a bulky alkyl such as, but not limited to, tert-butyl, isobutyl, isopropyl, trityl, cumyl and tert-hexyl.

As used herein, the phrase "bulky", in the context of a group or an alkyl in particular, describes a group that occupies a large volume. A bulkiness of a group or an alkyl is determined by the number and size of the atoms composing the group, by their arrangement, and by the interactions between the atoms (e.g., bond lengths, repulsive interactions). Typically, lower, linear alkyls are less bulky than branched alkyls; bicyclic molecules are more bulky than cycloalkyls, etc.

Exemplary bulky alkyls include, but are not limited to, branched alkyls such as tert-butyl, isobutyl, isopropyl and tert-hexyl, as well as substituted alkyls such as triphenylmethane (trityl) and cumyl.

In some of any of the embodiments pertaining to Formula IA, at least one of $R_{23}$-$R_{26}$ is independently a halo, for example, chloro, bromo or iodo, preferably chloro.

In some of any of the embodiments pertaining to Formula IA, at least one of $R_{24}$ and $R_{26}$ is halo (e.g., chloro).

In some of any of the embodiments pertaining to Formula IA, at least one of $R_{23}$-$R_{26}$ is a bulky rigid group.

The bulky rigid group can be, for example, aryl, heteroaryl, cycloalkyl and heteroalicyclic, having at least 7 carbon atoms.

As used herein, the phrase "bulky rigid group" describes a bulky group, as defined herein, with reduced number of free-rotating bonds. Such a group, unlike bulky alkyls, are rigid in terms of free rotation. Exemplary bulky rigid groups that are suitable for use in the context of embodiments of the invention include, but are not limited to, aryl, heteroaryl, cycloalkyl and/or heteroalicyclic, as defined herein.

In some embodiments, the rigid bulky group is such that has a total of 7 carbon atoms or more, each being substituted or unsubstituted.

In some embodiments, the bulky rigid group is a bicyclic group, comprising two or more of a cycloalkyl, aryl, heteroalicyclic or heteroaryl fused or linked to one another.

An exemplary bulky rigid group is adamantyl, for example, 1-adamantyl.

In some of any of the embodiments pertaining to Formula IA, $R_{26}$ is a bulky rigid group, as defined herein, for example, 1-adamantyl.

In some of any of the embodiments pertaining to Formula IA, each of $R_{27}$-$R_{30}$ is hydrogen, although any other substituents are contemplated.

In some of any of the embodiments pertaining to Formula IA, at least one of $R_{27}$-$R_{30}$ is a heteroalicyclic or a heteroaryl, preferably a nitrogen-containing heteroalicyclic or heteroaryl, as described herein. In some of these embodiments, the additional nitrogen atom also coordinates with the metal atom M, such the complex comprises a pentadentate ligand.

In some of any of the embodiments pertaining to Formula IA, $R_{30}$ is a nitrogen-containing heteroaryl, and in some of these embodiments, the complex comprises a pentadentate ligand.

In some of any of the embodiments described herein for Formula I or IA, $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein for Formula I or IA, one or both of $R_1$ and $R_2$ form together with one or more carbon atoms in A, a heteroalicyclic 5-, 6- or 7-membered ring.

In some of any of the embodiments described herein for Formula I or IA, at least one of $R_1$ and $R_2$ do/does not form together with one or more carbon atoms in A, a heteroalicyclic 5-, 6- or 7-membered ring.

In some of any of the embodiments described herein for Formula I or IA, at least one of $R_1$ and $R_2$ do/does not form together with one or more carbon atoms in A, a pyrrolidone ring.

In some of any of the embodiments described herein for Formula I or IA, A is other than bispyrrolidone.

In some of any of the embodiments described herein, for Formula I and IA, the A bridging moiety has a general Formula A1, A2 or A3:

    Formula A1

    Formula A2

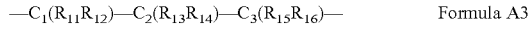    Formula A3 wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or any of the other substituents described herein, or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5-, 6- or 7-membered alicyclic, heteroalicyclic, aromatic or heterocyclic ring.

In some of any of the embodiments described herein, in formula A1, each of $R_5$ and $R_6$ is hydrogen, that is, A is methylene.

In some of any of the embodiments described herein, in formula A2, each of $R_7$-$R_{10}$ is hydrogen, that is, A is ethylene.

In some of any of the embodiments described herein, in formula A3, each of $R_{11}$-$R_{16}$ is hydrogen, that is, A is propylene.

In some of the embodiments where the bridging moiety A is an alkylene chain (methylene, ethylene or propylene), $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein, the bridging moiety has the Formula A2.

In some of any of the embodiments described herein, in formula A2, each of $R_7$-$R_{10}$ is hydrogen. In some of these embodiments, $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein, in formula A2, $R_7$ and $R_1$ form the heteroalicyclic ring, for example, a pyrrolidine.

Alternatively, or in addition, in some embodiments, $R_9$ and $R_2$ form the heteroalicyclic ring, for example, a pyrrolidine.

In some of any of the embodiments described herein for formula A2, the bridging moiety is bipyrrolidine.

In some of any of the embodiments described herein, at least one, or both, of $R_1$ and $R_2$ is independently an alkyl, for example, methyl.

Exemplary, non-limiting examples of complexes according to the present embodiments are presented in the Examples section that follows.

In some of any of the embodiments described herein, the catalyst system further comprises an initiator and in some embodiments the initiator is a hydroxy-containing compound, as described herein.

The hydroxy-containing compound can feature one hydroxy group, and can be, for example, HO-Rk, wherein Rk is alkyl, cycloalkyl or aryl.

Exemplary such initiators include, without limitation, benzyl alcohol, and alkyl alcohols such as ethyl alcohol, methyl alcohol, 2-propyl alcohol, tert-butyl alcohol, and monohydroxy terminated polyethylene glycol.

The hydroxy-containing compound can feature two or more hydroxy groups, and such compounds are also referred to herein and in the art as polyhydroxy compounds.

Exemplary such compounds include, but are not limited to, alkylene glycols (featuring 2 hydroxy groups, for example, ethylene glycol, propylene glycol, etc., as glycerols (featuring 3 hydroxy groups), higher linear saccharides, and polyhydroxy compounds such poly(ethylene glycol) or pentaerythritol.

The type of initiator, namely, the number of the hydroxy groups in the initiator determines the number of the polymeric chains in each of the units of polymerized monomers of the cyclic ester.

A mol ratio of the cyclic ester and the initiator determines the number of backbone units in each of the units of polymerized monomers in the block copolymer Thus, the polymer architecture (e.g., number and length of the polymeric chains) can be determined or controlled as desired by using an initiator that provides for the desirable properties.

Catalysts Systems Featuring a Divergent {ONNN} Ligand:

According to an aspect of some embodiments of the present invention, there is provided a process of ring opening polymerization of a cyclic ester, the process comprising contacting the cyclic ester with a catalyst system that comprises an organometallic complex featuring a divergent {ONNN} ligand as described herein in any of the respective embodiments. In some of these embodiments, the polymerization is an isoselective polymerization as described herein, According to an aspect of some embodiments of the present invention, there is provided a process of preparing a block polyester copolymer as described herein, wherein the polymerization is effected by sequentially contacting the cyclic ester monomers with a catalyst system that comprises an organometallic complex featuring a divergent {ONNN} ligand as described herein in any of the respective embodiments.

The processes parameters, the cyclic ester, the obtained copolymers and the catalyst system are as described herein in any of the respective embodiments.

According to some of any of the embodiments described herein, the organometallic magnesium complex featuring a divergent ligand comprises a Mg—X unit (e.g., one or two such units) and a divergent {ONNN} ligand in coordination with the one or two Mg—X units.

According to some of any of these embodiments, the magnesium complex is a mononuclear complex, featuring one Mg—X unit, and is represented by Formula IIA, and according to some of any of these embodiments, the magnesium complex is a dinuclear complex, featuring two Mg—X units, and is represented by Formula IIB:

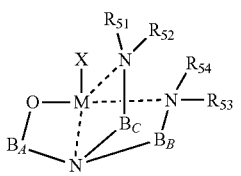

Formula IIA

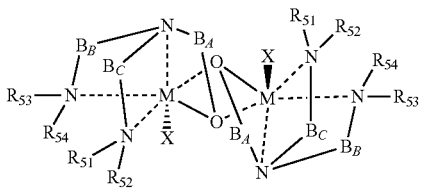

Formula IIB wherein:
the dashed line represents a coordinative bond;
M is magnesium;
X is a monoanionic ligand, the monoanionic ligand, as described herein in any of the respective embodiments and any combination thereof, provided that X is not alkoxy or aryloxy;
$B_A$, $B_B$ and $B_C$ are each independently a bridging moiety of 1 to 12 carbon atoms;
$R_{51}$ and $R_{52}$ are each independently hydrogen, alkyl, cycloalkyl, aryl or alternatively, one or both of $R_{51}$ and $R_{52}$ form together, optionally with one or more carbon atoms in $B_C$, a heteroalicyclic or heteroaromatic, 5 to 7-membered ring; and
$R_{53}$ and $R_{54}$ are each independently hydrogen, alkyl, cycloalkyl, aryl or alternatively, one or both of $R_{53}$ and $R_{54}$ form together with one or more carbon atoms in $B_B$, a heteroalicyclic or heteroaromatic, 5 to 7-membered ring.

In some of any of the embodiments described herein, X in Formula IIA or IIB is halo or amine, as described herein in any of the respective embodiments and any combination thereof.

In some of any of the embodiments described herein for Formula IIA and IIB, $B_A$ bridging moiety has a general Formula:

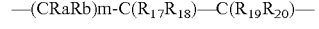
—(CRaRb)m-C($R_{17}R_{18}$)—C($R_{19}R_{20}$)— wherein:
m is an integer of from 1 to 6, or from 1 to 4, or from 1 to 2;
Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5 to 7-membered alicyclic, heteroalicyclic, aromatic or heteroaromatic ring with one or both Ra and Rb of an adjacent unit; and
$R_{17}$-$R_{20}$ are each independently hydrogen, alkyl, cycloalkyl, aryl, heteroaryl, heteroalicyclic, hydroxyl, alkoxy, thiol, thioalkoxy, aryloxy, and amine, or, alternatively, two or more of $R_{17}$-$R_{20}$ form together a 5 to 7-membered alicyclic, heteroalicyclic, aromatic or heteroaromatic ring.

In some of these embodiments, m is 1.

In some of any of these embodiments, Ra and Rb are each hydrogen.

In some of any of these embodiments, $R_{17}$-$R_{20}$ form together a substituted or unsubstituted, 6-membered, aromatic ring.

In some of any of these embodiments, the aromatic ring is unsubstituted, or is substituted by one or two substituents which are not bulky, as defined herein, (e.g., lower linear alkyls), and the complex has Formula IIB.

In some of any of these embodiments, the aromatic ring is substituted by one or more bulky substituents as defined herein (see, e.g., $R_{41}$ and $R_{42}$ in Formula III hereinunder, and the complex has Formula IIB.

In some of any of the embodiments described herein, the $B_B$ bridging moiety has a general Formula:

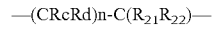
—(CRcRd)n-C($R_{21}R_{22}$)— wherein:
n is an integer of from 1 to 6, or from 1 to 4, or from 1 to 2;
Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit being the same or different, and one or both Rc and Rd in one unit optionally forms a 5 to 7-membered alicyclic, heteroalicyclic, aromatic or heteroaromatic ring with one or both Rc and Rd of an adjacent unit; and $R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_{53}$, $R_{54}$, $R_{21}$ and $R_{22}$ form together a 5 to 7-membered heteroalicyclic or heteroaromatic ring.

In some of these embodiments n is 1.

In some of these embodiments, Rc and Rd are each hydrogen.

In some of any of these embodiments, $R_{53}$, $R_{54}$, $R_{21}$ and $R_{22}$ form together a substituted or unsubstituted, 6-membered, heteroaromatic ring (e.g., a pyrrolidone).

In some of any of the embodiments described herein, the $B_C$ bridging moiety has a general Formula:

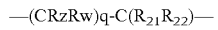
—(CRzRw)q-C($R_{21}R_{22}$)— wherein:

q is an integer of from 1 to 6, or from 1 to 4, or from 1 to 2;

Rz and Rw are each independently hydrogen, alkyl, cycloalkyl, aryl, heteroaryl, heteroalicyclic, hydroxyl, alkoxy, thiol, thioalkoxy, aryloxy, and amine, wherein when q is other than 1, Rz and Rw in each (CRzRw) unit being the same or different, and one or both Rz and Rw in one unit optionally forms a 5 to 7-membered alicyclic, heteroalicyclic, aromatic or heteroaromatic ring with one or both Rz and Rw of an adjacent unit; and $R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_{51}$, $R_{52}$, $R_{21}$ and $R_{22}$ form together a 5 to 7-membered heteroalicyclic or heteroaromatic ring.

In some of these embodiments q is 1.

In some of these embodiments, Rz and Rw are each hydrogen.

In some of these embodiments $R_{51}$, $R_{52}$, $R_{21}$ and $R_{22}$ form together a substituted or unsubstituted, 6-membered, heteroaromatic ring (e.g., a pyrollidine).

Any of the embodiments described herein for the $B_B$ bridging moiety in Formula I are contemplated for the $B_B$ and $B_C$ bridging moieties of Formula IIA or IIB.

Any of the embodiments described herein for the $B_A$ bridging moiety in Formula I are contemplated for the $B_A$ bridging moiety of Formula IIA or IIB.

In some of any of the embodiments described herein, the organometallic complex is represented by Formula III:

wherein:

$R_{41}$-$R_{48}$ and $R_{53}$-$R_{56}$ are each independently selected from the group consisting of hydrogen, alkyl, cycloalkyl, aryl, halo, alkoxy, aryloxy, trialkylsilyl, heteroalicyclic, heteroaryl, and amine, and all other variables are as described herein.

In some of these embodiments, at least one of $R_{41}$-$R_{44}$ is alkyl.

In some of these embodiments, at least one of $R_{41}$ and $R_{42}$ is alkyl.

In some of any of these embodiments, the alkyl is a bulky alkyl as described herein in any of the respective embodiments, and in some embodiments, it is a rigid bulky alkyl, as described herein in any of the respective embodiments.

In some of any of these embodiments, each of $R_{45}$-$R_{48}$ and $R_{53}$-$R_{56}$ is hydrogen.

In some of any of the embodiments described herein, the polymer is a block copolymer comprising a plurality of units, at least two of the units independently comprise a plurality of polymerized monomers of a cyclic ester, at least one unit of the at least two units comprises a plurality of polymerized monomers of a first cyclic ester, and at least one another unit of the at least two units comprises a plurality of polymerized monomers of a second cyclic ester, the second cyclic ester differing from the first cyclic ester by a stereoconfiguration and/or a chemical composition, the process comprising:

sequentially contacting a plurality of monomers of the first cyclic ester and a plurality of monomers of the second cyclic ester with the catalyst system comprising an initiator and an organometallic magnesium complex comprising a Mg—X unit and a divergent {ONNN} ligand in coordination with the Mg—X, to thereby sequentially effect a ring opening polymerization of the first cyclic ester and of the second cyclic ester.

According to an aspect of some embodiments of the present invention there is provided an organometallic complex represented by Formula III, as described herein.

In some of these embodiments, X is other than alkoxy or aryloxy, and is, for example, halo (e.g., chloro) or amine; and/or at least one of $R_{41}$ and $R_{42}$ is a bulky rigid alkyl, as defined herein.

According to an aspect of some embodiments of the present invention there is provided an organometallic complex represented by Formula IIB, as described herein in any of the respective embodiments.

In some embodiments, these is provided ligand precursor compound represented by Formula IV:

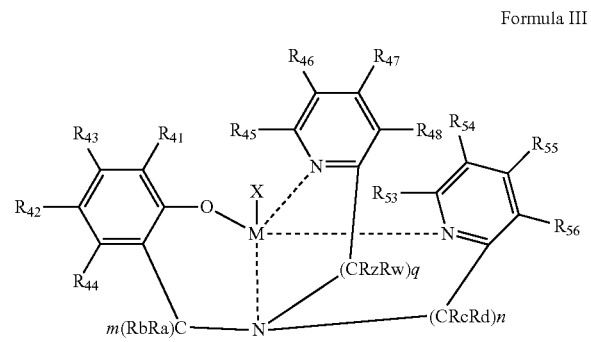

Formula III

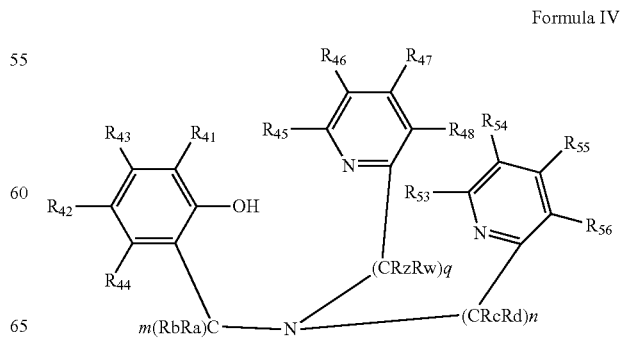

Formula IV wherein:

m, n and q are each independently an integer of from 1 to 6, or from 1 to 4, or from 1 to 2;

Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5 to 7-membered alicyclic, heteroalicyclic, aromatic or heteroaromatic ring with one or both Ra and Rb of an adjacent unit;

Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit being the same or different, and one or both Rc and Rd in one unit optionally forms a 5 to 7-membered alicyclic, heteroalicyclic, aromatic or heteroaromatic ring with one or both Rc and Rd of an adjacent unit;

Rz and Rw are each independently hydrogen, alkyl, cycloalkyl, aryl, heteroaryl, heteroalicyclic, hydroxyl, alkoxy, thiol, thioalkoxy, aryloxy, and amine, wherein when q is other than 1, Rz and Rw in each (CRzRw) unit being the same or different, and one or both Rz and Rw in one unit optionally forms a 5 to 7-membered alicyclic, heteroalicyclic, aromatic or heteroaromatic ring with one or both Rz and Rw of an adjacent unit; and $R_{41}$-$R_{48}$ and $R_{53}$-$R_{56}$ are each independently selected from the group consisting of hydrogen, alkyl, cycloalkyl, aryl, halo, alkoxy, aryloxy, trialkylsilyl, heteroalicyclic, heteroaryl, and amine, provided that at least one of $R_{41}$ and $R_{42}$ is a bulky rigid alkyl.

All variables of Formula IV are as defined herein in any of the respective embodiments.

As used herein the term "about" refers to ±10% or to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

Bisphenol A is An example of a hydrocarbon comprised of 2 aryl groups and one alkyl group.

As used herein, the term "amine" describes both a —NR'R" group and a —NR' group, wherein R' and R" are each independently hydrogen, alkyl, cycloalkyl, aryl, alkaryl, heteroaryl, heteroalicyclic, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, alkenyl, alkynyl, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The term "amine" is used herein to describe a —NR'R" group in cases where the amine is an end group, as defined hereinunder, and is used herein to describe a —NR' group in cases where the amine is a linking group or is or part of a linking moiety.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6, or 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene (or alkenyl) and Alkyne (or alkynyl), as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholine, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, pyrrolidone, oxazole, indole, purine and the like.

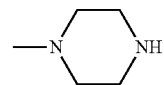

The term "piperazine" refers to a group or a

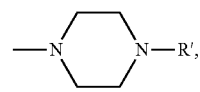

or a

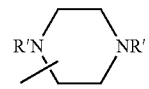

group, where R' and R" are as defined hereinabove.

The term "piperidine" refers to a group

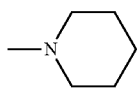

or a

group, with R' as defined herein.

The term "pyrrolidine" refers to a

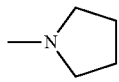

group or a

group, with R' as defined herein.

The term "pyridine" refers to a

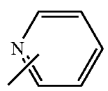

group.

The term pyrrole refers to a

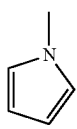

group or a

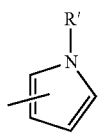

group, with R' as defined herein.

The term "morpholine" refers to a

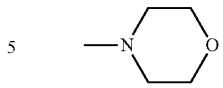

group, and encompasses also thiomorpholine.

The term "thiomorpholine" refers to a

group.

The term "hexahydroazepine" refers to a

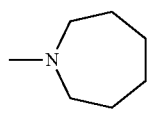

group.

The term "alkaryl" describes an alkyl, as defined herein, which is substituted by one or more aryl or heteroaryl groups, as defined herein. An example of alkaryl is benzyl.

The term "halide", "halogen" and "halo" describe fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "cyanurate" describes a

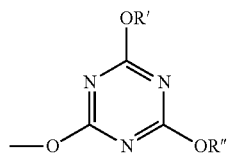

end group or

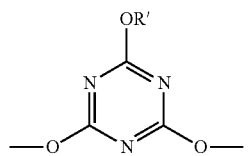

linking group, with R' and R" as defined herein.

The term "isocyanurate" describes a R

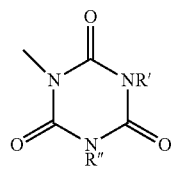

end group or a

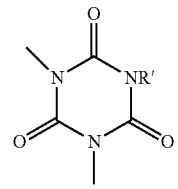

linking group, with R' and R" as defined herein.

The term "thiocyanurate" describes a

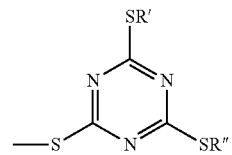

end group or

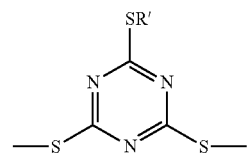

linking group, with R' and R" as defined herein.

The term "isocyanate" describes an —N=C=O group.

The term "isothiocyanate" describes an —N=C=S group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)— NR"— linking group, as these phrases are defined hereinabove, where R', R" and R'" are as defined herein.

The term "hydrazine" describes a —NR'—NR"R'" end group or a —NR'— NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "alkylene glycol" describes a —O—[(CR'R")$_z$—O]$_y$—R'" end group or a —O—[(CR'R")$_z$—O]$_y$— linking group, with R', R" and R'" being as defined herein, and with z being an integer of from 1 to 10, preferably, 2-6, more preferably 2 or 3, and y being an integer of 1 or more. Preferably R' and R" are both hydrogen. When z is 2 and y is 1, this group is ethylene glycol. When z is 3 and y is 1, this group is propylene glycol.

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR')R"— linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" describes a —O—Si(OR')(OR")(OR'") end group or a —O—Si(OR')(OR")— linking group, as these phrases are defined hereinabove, with R', R" and R'" as defined herein.

As used herein, the term "epoxide" describes a

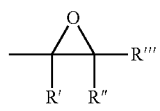

end group or a

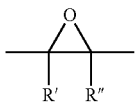

linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein. This term encompasses ketones and aldehydes.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "cyclic ring" encompasses a cycloalkyl, a heteroalicyclic, an aryl (an aromatic ring) and a heteroaryl (a heteroaromatic ring).

Other chemical groups are to be regarded according to the common definition thereof in the art and/or in line of the definitions provided herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

All reactions with air- and/or water sensitive compounds were carried out using standard Schlenk or glovebox techniques under dry N$_2$ atmosphere. Pentane was washed with HNO$_3$/H$_2$SO$_4$ prior to distillation from Na/benzophenone/tetraglyme. Toluene was refluxed over Na and distilled. Dichloromethane was refluxed over CaH$_2$ and distilled. Benzyl magnesium chloride solution, anhydrous benzyl alcohol, 1,4-benzenedimethanol and salicylaldehyde were purchased from Aldrich and used as received. Bis(2-pyridylmethyl)amine was purchased from TCI and used as received. Sodium triacetoxyborohydride was purchased from Strem and used as received. L-lactide and D-lactide were given as gift from Corbion (Purac), and were purified by crystallization from dry toluene and sublimation. F-Caprolactone was purchased from Merck, and was refluxed over CaH$_2$ and distilled prior to use.

The ligand precursor Lig$^1$H was synthesized following a previously published procedure. See, for example, Rosen et al., *Chem. Eur. J.* 2016, 22, 11533-11536.

The ligand precursors Lig$^{2-6}$H were synthesized following a previously published procedure. See, for example, Rosen et al., *Chem. Sci.* DOI: 10.1039/C7SC01514C.

The magnesium precursor Mg(HMDS)$_2$ was synthesized following a previously published procedure. See, for example, Allan et al., *Chem. Commun.* 1999, 1325-1326.

Deuterated solvents were purchased from Cambridge Isotope Laboratories, Inc., degassed, and dried over activated 4 Å molecular sieves prior to use.

The NMR spectra were recorded on a Bruker Avance 500 spectrometer at 25° C., unless otherwise stated. Chemical shifts (δ) are listed as parts per million and coupling constants (J) in Hertz. $^1$H NMR spectra are referenced using the residual solvent peak at δ=5.32 for CD$_2$Cl$_2$. $^{13}$C NMR spectra are referenced using the residual solvent peak at δ=53.84 for CD$_2$Cl$_2$.

The molecular weights (Mn and Mw) and the molecular mass distributions (Mw/Mn) of the PLA samples were measured by gel permeation chromatography (GPC) at 40° C., using THF as solvent, flow rate of eluent of 1 mL/min, and narrow Mw polystyrene standards as reference. The measurements were performed on a Jasco system equipped with an RI 1530 detector. A correction factor of 0.58 was employed for the molecular weight of PLA relative to polystyrene. Insoluble PLA samples were measured using chloroform as solvent at 30° C. with flow rate of eluent of 0.8 mL/min.

High resolution MS was obtained on SYNAPT (Waters Inc.) spectrometer. Ionization methods: APPI (positive or negative). X-ray diffraction measurements were performed on an ApexDuo (Bruker-AXS) diffractometer system, using Mo Kα (λ=0.7107 Å) radiation. The analyzed crystals were embedded within a drop of viscous oil and freeze-cooled to ca. 110 K.

MALDI-TOF analysis was carried out on a Bruker autoflex mass spectrometer. The polymer samples were dissolved in THF at a concentration of 10 mg/ml. The matrix used was either HABA (2-(4-hydroxyphenylazo) benzoic acid) or α-CCA (α-cyano-4-hydroxycinanamic acid) with sodium trifluoroacetate as cationization agent. The final matrix solution was prepared in the volume ratio of 10:1:3 of solutions of matrix, salt and polymer sample, respectively. A portion of this mixture was then placed on the MALDI plate and allowed to dry in air. The spectra were recorded in positive linear mode or positive reflectron mode.

Differential scanning calorimetry analysis was performed on a TA 2920 DSC (TA Instruments) according to the following program: Ramp 10.00° C./min to 200.00° C.; Equilibrate at 195.00° C.; Isothermal for 2 min; Ramp 10.00° C./min to 50.00° C.; Equilibrate at 50.00° C.; Ramp 10.00° C./min to 200.00° C. Melting transitions were determined on the second heating run with a nitrogen purge at a flow rate of 40 mL s−1.

The instrument was calibrated for temperature and enthalpy by high purity indium (156.60° C., 28.45 J g−1) standard.

Example 1

Synthesis of Magnesium Complexes of Sequential {ONNN} Ligands

Synthesis of (R,R)-Lig$^1$Mg—Cl

Scheme 2 below presents the preferred synthetic pathway for preparing an exemplary Mg complex according to some embodiments of the present invention.

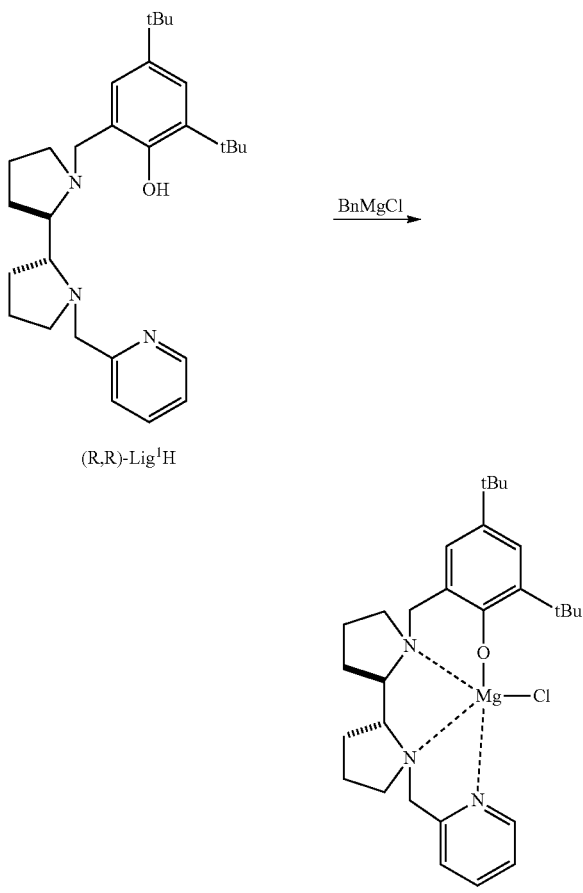

Scheme 2

To a stirred solution of (R,R)-Lig$^1$H (110 mg, 0.24 mmol) in toluene (1 mL), was added a solution of BnMgCl (0.24 mL, 0.24 mmol, 1M diethyl ether solution) drop-wise. The resulting mixture was stirred at room temperature for 1 hour until a precipitation appeared. The solvent was removed under vacuum and the residue was washed with pentane to give a yellow solid in 81% yield.

Figure 2:
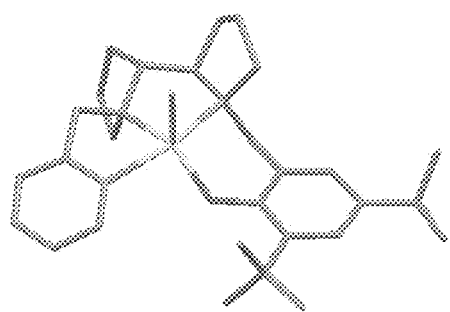
FIG. 2 presents the crystallographic structure of an exemplary {ONNN}Mg—Cl complex according to some embodiments of the present invention.

$^1$H NMR analysis revealed that the obtained {ONNN}Mg—Cl complex had formed as a single rigid stereoisomer, and X-ray diffraction measurements revealed a pentacoordinate mononuclear magnesium complex similar to the corresponding zinc complex, as shown in FIG. 2.

$^1$H NMR (CD$_2$Cl$_2$, 500 MHz): δ 8.94 (d, 1H, J=4.91 Hz, ArH), 7.87 (td, 1H, J=1.57 Hz, J=7.73 Hz, ArH), 7.48 (dd, 1H, J=5.21 Hz, 7.66 Hz, ArH), 7.30 (d, 1H, J=7.68 Hz, ArH), 7.18 (d, 1H, J=2.59 Hz, ArH), 6.79 (d, 1H, J=2.65 Hz, ArH), 4.20 (d, 1H, J=14.45 Hz, CH$_2$), 3.84 (d, 1H, J=11.46 Hz, CH$_2$), 3.70 (d, 1H, J=14.52 Hz, CH$_2$), 3.46 (d, 1H, 11.44 Hz, CH$_2$), 3.22-3.16 (m, 2H, CH$_2$), 2.93-2.87 (m, 1H, CH$_2$), 2.80 (qd, 1H, J=2.49 Hz, CH), 2.67 (dt, 1H, J=6.63 Hz, CH$_2$), 2.54-2.50 (m, 1H, CH$_2$), 2.12-2.04 (m, 3H, CH$_2$), 1.96-1.91 (m, 2H, CH$_2$), 1.86-1.84 (m, 1H, CH$_2$), 1.74-1.68 (m, 1H, CH$_2$), 1.59-1.52 (m, 1H, CH$_2$), 1.47 (s, 9H, C(CH$_3$)$_3$), 1.26 (s, 9H, C(CH$_3$)$_3$).

$^{13}$C NMR (CD$_2$Cl$_2$, 125 MHz): δ 163.46 (C), 156.33 (C), 149.34 (CH), 139.60 (CH), 137.20 (C), 134.37 (C), 126.08 (CH), 124.54 (CH), 123.94 (CH), 123.81 (CH), 69.98 (CH$_2$), 67.36 (CH), 63.28 (CH), 59.01 (CH$_2$), 50.91 (CH$_2$), 35.47 (C), 34.06 (C), 32.06 (CH$_3$), 29.78 (CH$_3$), 28.03 (CH$_2$), 26.54 (CH$_2$), 23.95 (CH$_2$), 20.51 (CH$_2$).

HRMS (APPI$^+$): Calc for C$_{29}$H$_{42}$ClMgN$_3$O: 507.2867, found: 507.2874 (M$^+$).

Crystal Data for Complex [(R,R)-Lig$^1$Mg—Cl.CH$_2$Cl$_2$]. C$_{29}$H$_{42}$CN$_3$OMg, CH$_2$Cl$_2$; M=593.34; orthorhombic; space group P 21 21 21; a=7.9066(5) Å, b=17.5510(13) Å, c=22.4279(18) Å, V=3112.3(4) Å3; T=110(2) K; Z=4; Dc=1.266 g cm−3; μ(Mo Kα)=0.342 mm−1; R1=0.0733 and wR2=0.1718 for 4786 reflections with I>2σ (I); R1=0.0634 and wR2=0.1638 for all 4196 unique reflections.

Synthesis of (R,R)-Lig$^1$Mg-HMDS

Figure 3:
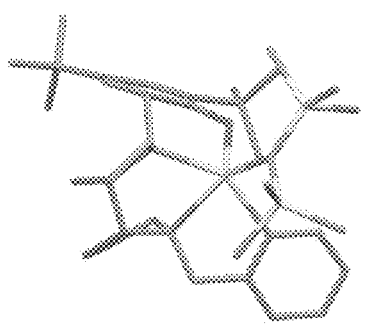
FIG. 3 presents the crystallographic structure of an exemplary {ONNN}Mg-HMDS complex according to some embodiments of the present invention.

To a stirred solution of Mg(HMDS)$_2$ (50 mg, 0.14 mmol) in toluene (1 mL), was added a solution of (R,R)-Lig$^1$H (65 mg, 0.14 mmol) in toluene (1 mL) drop-wise. The resulting mixture was stirred at room temperature for 4 hours. The solvent was hereafter removed under vacuum and the residue was washed with pentane to give an off-white solid in 85% yield $^1$H NMR spectroscopy analysis demonstrated that {ONNN}Mg-HMDS had formed as a single rigid stereoisomer of C$_1$-symmetry, and X-ray diffraction measurements revealed a pentacoordinate mononuclear magnesium complex adopting an almost ideal square pyramidal geometry (L=0.06) with the phenolate oxygen at the apical position, as shown in FIG. 3.

$^1$H NMR (C$_6$D$_6$, 500 MHz): δ 9.17 (d, 1H, J=4.9 Hz, ArH), 7.50 (d, 1H, J=2.6 Hz, ArH), 6.90 (d, 1H, J=2.6 Hz, ArH), 6.86 (dt, 1H, J=7.7 Hz, J=1.7 Hz, ArH), 6.65 (dd, 1H, J=7.7 Hz, J=4.8 Hz, ArH), 6.19 (d, 1H, J=7.7 Hz, ArH), 4.58 (d, 1H, J=12.2 Hz, CH$_2$), 3.51-3.45 (m, 1H, CH), 3.31 (d, 1H, J=15.4 Hz, CH$_2$), 2.99 (d, 1H, J=12.2 Hz, CH$_2$), 2.96-2.95 (m, 1H, CH), 2.78-2.73 (m, 1H, CH$_2$), 2.73 (d, 1H, J=15.4 Hz, CH$_2$), 2.30-2.24 (m, 2H, CH$_2$), 1.82-1.69 (m, 4H, CH$_2$), 1.56 (s, 9H, C(CH$_3$)$_3$), 1.44 (s, 9H, C(CH$_3$)$_3$), 1.17-1.15 (m, 2H, CH$_2$), 0.97-0.95 (m, 3H, CH$_2$), 0.76 (s, 9H, Si(CH$_3$)$_3$), 0.14 (s, 9H, Si(CH$_3$)$_3$). $^{13}$C NMR (C$_6$D$_6$, 125 MHz): δ 165.09 (C), 155.94 (C), 150.64 (CH), 138.44 (CH), 137.20 (C), 132.99 (C), 126.56 (CH), 124.12 (CH), 123.36 (CH), 123.16 (C), 122.23(CH), 69.40 (CH), 61.85 (CH), 61.76 (CH$_2$), 59.26 (CH$_2$), 55.38 (CH$_2$), 51.34 (CH$_2$), 35.53 (C), 34.08 (C), 32.44 (CH$_3$), 30.23 (CH$_3$), 26.32 (CH$_2$), 25.75 (CH$_2$), 22.82 (CH$_2$), 19.13 (CH$_2$), 7.71 (CH$_3$), 7.05 (CH$_3$). HRMS (APPI$^+$): Calc for C$_{35}$H$_{60}$MgN$_4$OSi$_2$: 632.4156, found: 472.3162 [M-HMDS]$^+$.

Crystal Data for Complex [(R,R)-LigMg-HMDS]. C$_{35}$H$_{60}$MgN$_4$OSi$_2$; M=633.36; orthorhombic; space group P 2ac 2ab; a=11.4994(6) Å, b=16.5576(7) Å, c=19.7586(8), V=3762.1(3) Å3; T=110(2) K; Z=4; Dc=1.118 g cm$^{-3}$; µ (MoKα)=0.142 mm$^{-1}$; R1=0.0455 and wR2=0.0833 for 6263 reflections with I>2σ (I); R1=0.0380 and wR2=0.0802 for all 5605 unique reflections.

Example 2

Homo-Polymerization and Block-Polymerization of Lactides Employing an Exemplary Sequential {ONNN}Mg—Cl Complex General Homo-Polymerization Procedure:

To a solution of the catalyst (0.01 mmol) in dichloromethane (5 mL), benzyl alcohol (0.01 mmol) was added, and the reaction mixture was stirred at room temperature for 2 minutes. Then, L-lactide (432 mg, 3 mmol) was added, and the reaction was stirred at room temperature. After the desired time, the reaction was terminated by exposing to air and the volatiles were removed under vacuum.

General Block-Polymerization Procedure: To a solution of the catalyst (0.01 mmol) in dichloromethane (5 mL), benzyl alcohol (2 mol equivalents) was added and the reaction mixture was stirred at room temperature for 2 minutes. Then, D-Lactide and L-Lactide were sequentially added, each separately, maintaining the necessary delay (5-20 minutes) between each addition. The reaction was terminated by exposing to air and the volatiles were removed under vacuum. The tacticity of the PLA samples was determined by the homonuclear-decoupled $^1$H NMR spectrometry (500 MHz, CDCl$_3$) as previously described in Stopper et al. *Macromolecules* 45, 698 (2012); Thakur et al. *Macromolecules* 30, 2422 (1997); and Chamberlain et al. *J. Am. Chem. Soc.* 123, 3229 (2001).

Polymerization Results:

Tables 1 and 2 present the data obtained for homo-polymerization of L-LA (Table 1) and block co-polymerization of L-LA and D-LA (Table 2), employing (R,R)-Lig$^1$Mg—Cl, in dichloromethane at room temperature.

TABLE 1

| [I]/[LA]/[BnOH] | Time | Conversion$^a$ | M$_{n\ calc}$ | M$_n$ | PDI |
|---|---|---|---|---|---|
| 1. 1/0/300 | <15 sec | >0.99 | 43200 | 106600 | 1.28 |
| 2. 1/1/300 | 1 min | >0.99 | 43200 | 44440 | 1.04 |
| 3. 0.5/1/300 | 1 min | >0.99 | 43200 | 41360 | 1.05 |
| 4. 0.5/2/300 | 1 min | >0.99 | 21600 | 23420 | 1.05 |
| 5. 0.5/1/1000 | 3 min | >0.99 | 144000 | 137560 | 1.06 |
| 6. 0.5/1/2150 | 5 min | >0.99 | 309600 | 266000 | 1.07 |

$^a$Determined by 1H-NMR spectroscopy (500 MHz).

TABLE 2

| | Type | Composition | Interval (minutes) | M$_n$ | PDI |
|---|---|---|---|---|---|
| 1. | Di Block | 150L-150D | 5 | 47000 | 1.04 |
| 2. | Di Block | 150D-150L | 5 | 53000 | 1.06 |
| 3. | Di Block | 300D-300L | 10 | 90000$^b$ | 1.13 |
| 4. | Di Block | 400L-400D | 15 | 126400$^b$ | 1.07 |
| 5. | Di Block | 400D-400L | 15 | 128700$^b$ | 1.08 |
| 6. | Di Block | 500L-500D | 15 | 177000$^b$ | 1.11 |
| 7. | Tri Block | 100L-100D-100L | 5 | 45500 | 1.06 |
| 8. | Tri Block | 100L-200D-100L | 5 | 50000 | 1.06 |
| 9. | Tri Block | 150L-50D-150L | 5 | 54200 | 1.07 |
| 10. | Tri Block | 200L-200D-200L | 10 | 81500 | 1.12 |
| 11. | Tri Block | 200D-200L-200D | 10 | 69000 | 1.13 |
| 12. | Tri Block | 150L-15D-150L | 5 | 40500 | 1.05 |
| 13. | Tri Block | 300L-15D-300L | 5-10 | 87600 | 1.14 |
| 14. | Tetra Block | 50L-50D-50L-50D | 5 | 25400 | 1.04 |
| 15. | Tetra Block | 100L-100D-100L-100D | 5 | 64300 | 1.12 |
| 16. | Tetra Block | 200L-200D-200L-200D | 5-20 | 122910$^b$ | 1.13 |
| 17. | Tetra Block | 200L-33D-200L-33D | 5-10 | 70650 | 1.14 |
| 18. | Tetra Block | 200L-32D-32L-200D | 5-10 | 72690 | 1.31 |
| 19. | Tetra Block | 100L-250D-50L-150D | 5-15 | 75040 | 1.27 |
| 20. | Penta Block | 100L-100D-100L-100D-100L-100D | 5-15 | 61000 | 1.12 |
| 21. | Hexa Block | 50L-50D-50L-50D-50L-50D-50L | 5-10 | 34000 | 1.10 |
| 22. | Hexa Block | 100L-b-100D-b-100L-b-100D-b-100L-b-100D | | 72820 | 1.16 |
| 23. | Octa Block | 50L-b-50D-b-50L-b-50D-b-50L-b-50D-b-50L-b-50D-b-50L | | 50984 | 1.12 |

$^b$GPC measurements were performed with CHCl$_3$ as eluent at 30° C.

Figure 5A:
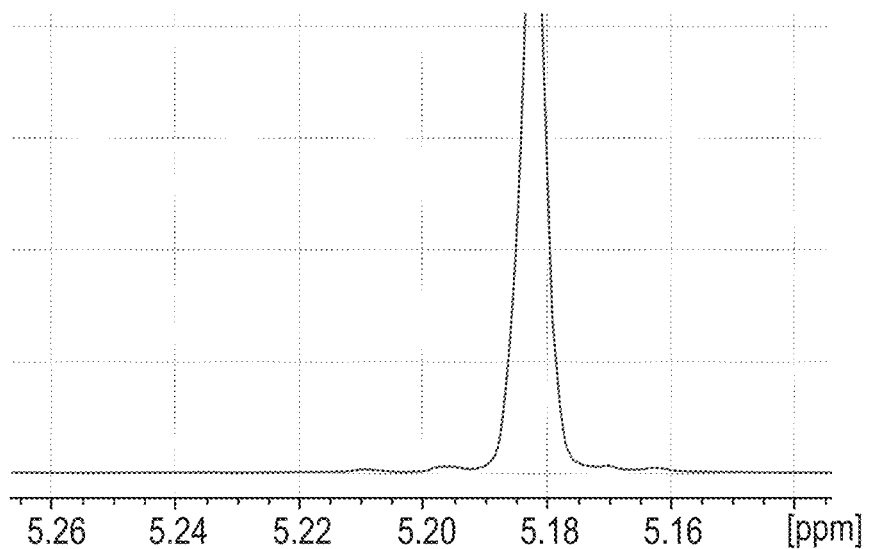
FIGS. 5A-5C present homodecoupled $^1$H NMR spectra of PLA samples, with FIG. 5A showing spectrum of a precise isotactic diblock-copolymer (150D-b-150L) showing no errors, FIG. 5B showing spectrum of a gradient isotactic diblock-copolymer (96L-b-(100D+4L)) clearly showing stereoerrors, and FIG. 5C showing spectra of PLLA and several isotactic block copolymers bearing different block numbers.
Figure 5B:
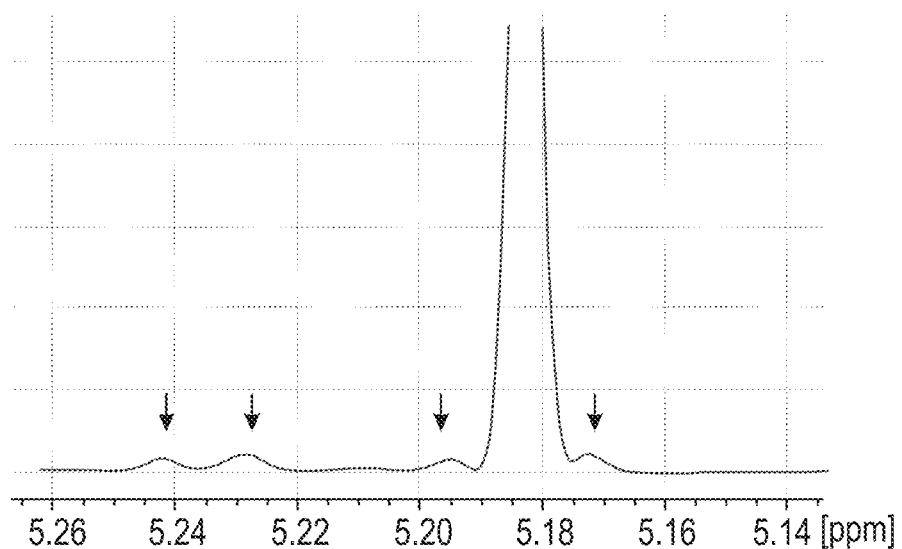
Figure 5C:
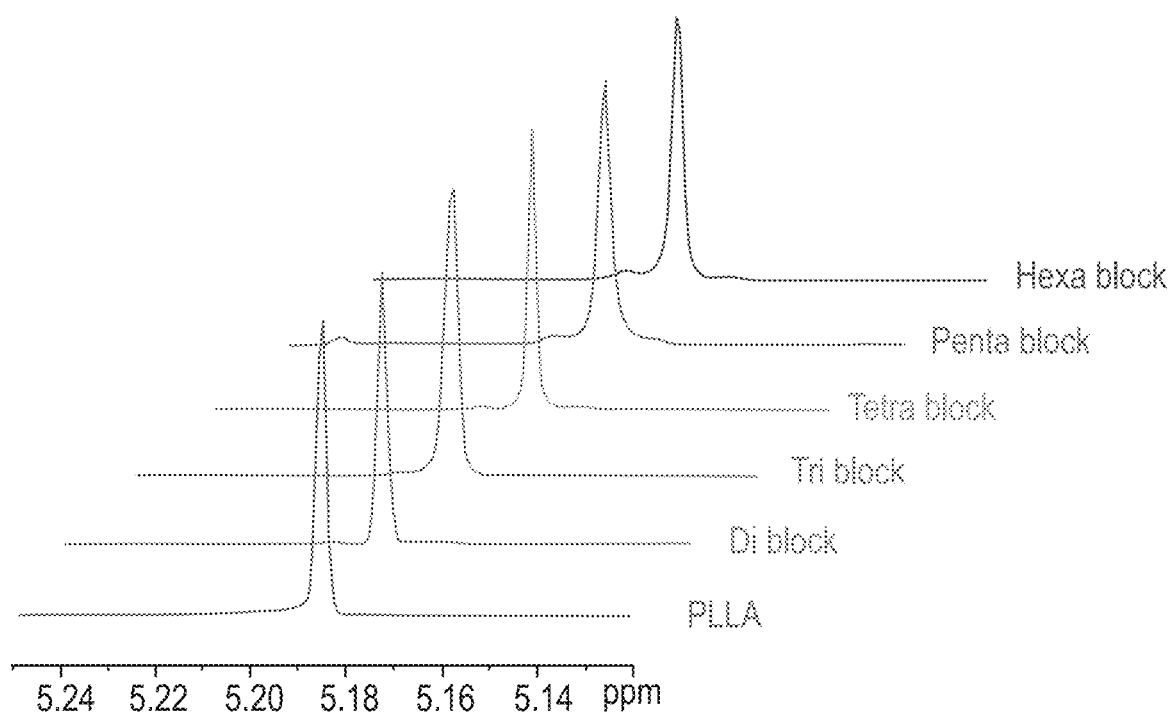
Figure 6:
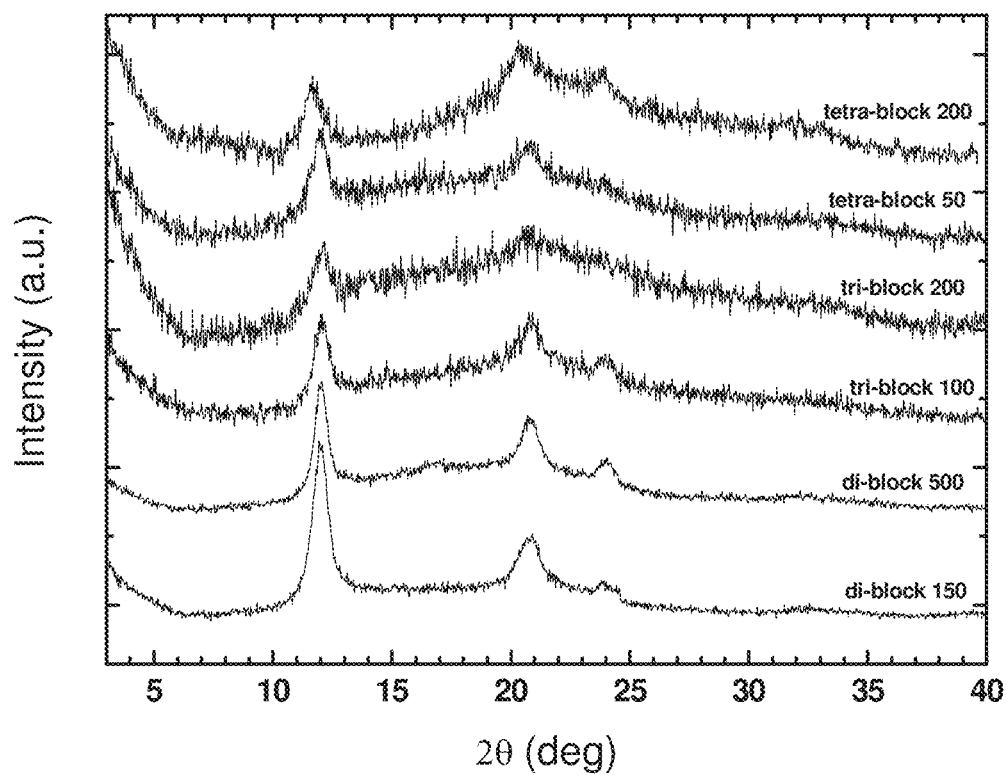
FIG. 6 presents X-ray diffraction patterns of selected stereo-n-blocks, with n and block-length of samples are indicated in the labels.

Homonuclear-decoupled $^1$H NMR spectra of the obtained PLA homo-polymers and block-copolymers are presented in FIGS. 5A-5C.

Tables 3-5 below present the DSC data of various stereo-diblocks (Table 3), stereotriblock (Table 4) and stereotetra-blocks (Table 5) obtained with (R,R)-Lig$^1$Mg—Cl.

TABLE 3

| | First run | | Cooling | | | | Second run | |
|---|---|---|---|---|---|---|---|---|
| Composition | Tm | ΔHm | Tc | ΔHc | Tg | Tc/ΔHc | Tm | ΔHm |
| D150-b-L150 | 219.1 | 80.5 | 188 | 65 | 56 | — | 212.7 | 62.1 |
| D300-b-L300 | 218.0 | 70.6 | 183 | 68 | 55 | — | 214.0 | 67.9 |
| L400-b-D400 | 211.8 | 79.0 | 135 | 51 | 56 | — | 213.2 | 50.4 |
| D400-b-L400 | 215.9 | 71.4 | 159 | 57 | 56 | — | 209.9 | 57.0 |
| L500-b-D500 | 215.1 | 85.4 | 152 | 59 | 58 | — | 215.1 | 58.0 |

T (° C.);
ΔH (J/g)

TABLE 4

| Composition | First run | | Cooling | | | Second run | | |
| --- | --- | --- | --- | --- | --- | --- | --- | --- |
| | Tm | ΔHm | Tc | ΔHc | Tg | Tc/ΔHc | Tm | ΔHm |
| L100-b-D100-b-L100 | 206 | 45 | 131 | 40 | 55 | — | 207 | 42 |
| D100-b-L100-b-D100 | 206 | 51 | 135 | 43 | 55 | — | 208 | 42 |
| L200-b-D200-b-L200 | 207 | 40 | 130 | 37 | 54 | — | 205 | 36 |
| D200-b-L200-b-D200 | 207 | 49 | 137 | 47 | 52 | — | 204 | 44 |
| L100-b-D100-b-L100 + D100-b-L100-b-D100 | 211 | 65 | 141 | 56 | 58 | — | 212 | 53 |
| L200-b-D200-b-L200 + D200-b-L200-b-D200 | 211 | 68 | 136 | 56 | 57 | — | 210 | 49 |

T (° C.);
ΔH (J/g)

TABLE 5

| Composition | First run | | Cooling | | | Second run | | |
| --- | --- | --- | --- | --- | --- | --- | --- | --- |
| | Tm | ΔHm | Tc | ΔHc | Tg | Tc/ΔHc | Tm | ΔHm |
| L50-b-D50-b-L50-b-D50 | 192 | 44 | 118 | 44 | 54 | — | 195.0 | 45.8 |
| L100-b-D100-b-L100-b-D100 | 208 | 55 | 119 | 60 | 53 | — | 200.5 | 48.8 |
| L200-b-D200-b-L200-b-D200 | 201 | 71 | 124 | 48 | 58 | — | 206.8 | 50.3 |

T (° C.);
ΔH (J/g)

Polymerizations of the homochiral lactides were run in dichloromethane at room temperature by adding benzyl alcohol to the {ONNN}Mg—Cl complex followed by addition of the lactide. Preliminary runs showed that the addition of 1 mol equivalent of benzyl alcohol to the {ONNN}Mg—Cl solution followed by addition of 300 mol equivalents of L-LA led to full consumption of the monomer within one minute. This corresponds to one of the highest activities ever reported for lactide polymerization.

Gel permeation chromatographic (GPC) analysis of the polymer samples revealed exceptionally narrow MWD with typical values of Mw/Mn≤1.05, and number-average molecular weights (Mn) which coincided with the monomer/initiator molar ratio.

{ONNN}Mg—Cl was found to act as an "immortal polymerization" catalyst, namely, it enabled the growth of more than a single polymer chain by every magnesium center by simply employing more than a single equivalent of benzyl alcohol.

The PLA samples obtained under the immortal conditions retained very narrow MWD values, and the measured Mn's were consistent with the calculated values of monomer/benzyl alcohol molar ratio. The activity of the {ONNN}Mg—Cl complex was examined up to L-LA loading of 4300 mol equivalents (and 2 mol equivalents of benzyl alcohol). Full monomer consumption was reached in 6 minutes and the PLLA produced was monodisperse and of very high Mn.

While the narrow MWD and expected Mn of the PLA obtained are necessary requirements of living polymerization, a truly-living polymerization also requires that following the full consumption of the first monomer, the addition of a second portion of (the same or different) monomer would lead to a continued growth of all polymeryl chains.

200 mol equivalents of L-LA were polymerized with {ONNN}Mg—Cl under the above conditions, and a second portion of 200 mol equivalents of L-LA was added only after twelve hours. All 400 mol equivalents were consumed and the PLLA obtained was of narrow MWD and expected Mn. Namely, this catalyst hibernates when deprived of monomer and continues growing all polymeryl chains upon monomer addition.

Figure 4:
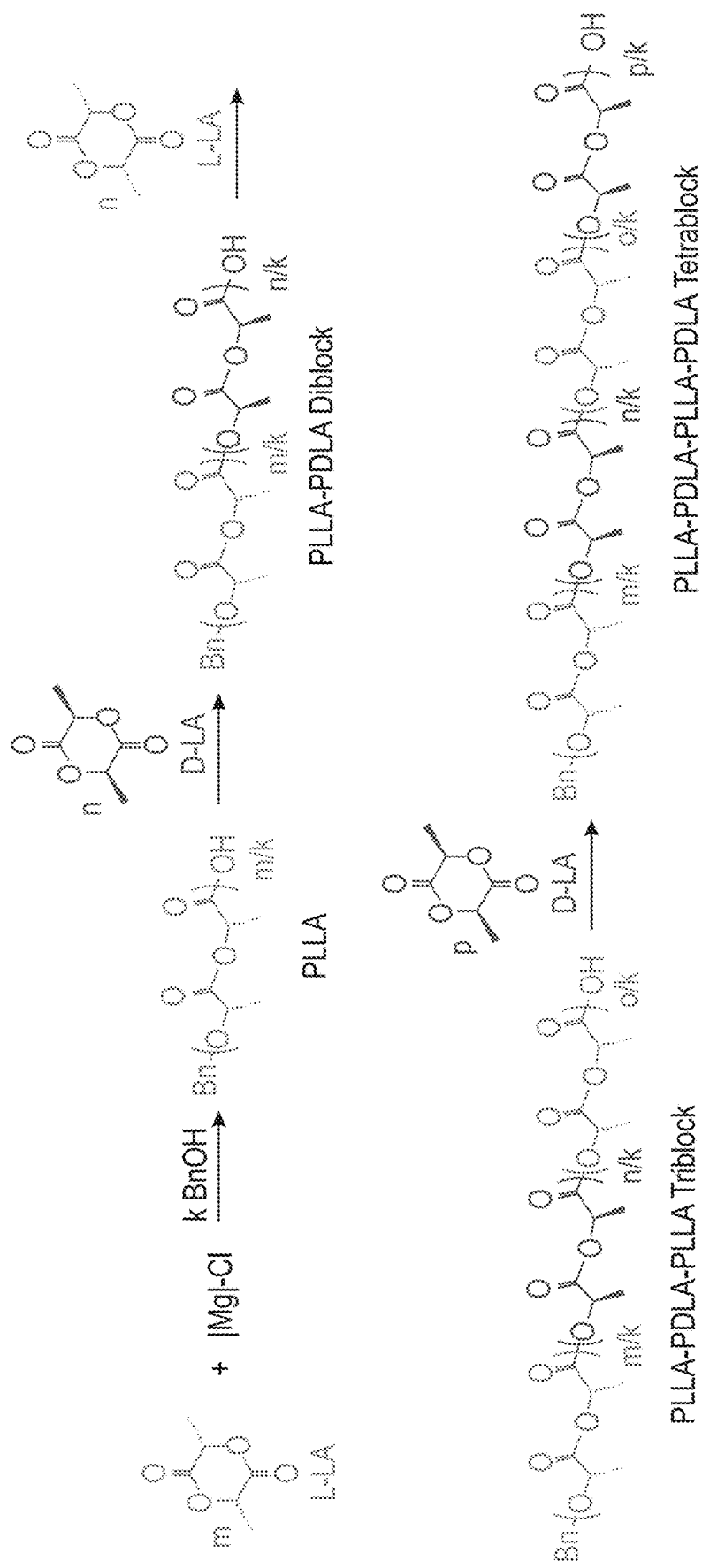
FIG. 4 is a schematic illustration of a one-pot synthesis of poly(lactic acid) homopolymers and isotactic stereoblock copolymers.

The synthesis of stereo-diblock copolymers was performed by adding L-LA to a stirring mixture of {ONNN}Mg—Cl and benzyl alcohol in dichloromethane, followed by addition of D-LA after several minutes and eventual workup after an identical interval, as illustrated in FIG. 4.

It was found that PLLA-PDLA diblock copolymers having identical block lengths each of 150 (2×5 minutes), 300 (2×10 minutes) and even 400 or 500 (2×15 minutes) repeat units were readily obtained by this one-pot synthesis. The two monomer enantiomers were fully consumed, and the polymer samples featured a perfectly isotactic stereo-diblock microstructure (rather than a gradient microstructure that would result from an incomplete consumption of the first lactide enantiomer), as shown by the sharp mmm tetrad in their homo-decoupled (HD) $^1$H NMR spectra (see, FIG. 5A).

A control experiment that mimics an incomplete first monomer conversion was run by polymerizing 96 mol equivalents of L-LA, waiting 10 minutes to ascertain a full conversion, and thereafter adding a mixture consisting of 100 mol equivalents of D-LA and 4 mol equivalents of L-LA and letting the polymerization proceed to full conversion.

HD $^1$H NMR of this sample showed stereoerrors that were absent from the original diblock copolymers, as shown in FIG. 5B, signifying that therein the conversion of the L-LA prior to the addition of the D-LA substantially exceeded 96%.

GPC analysis of the short diblock copolymers in THF and the less soluble longer diblock copolymers in chloroform revealed that they had all exhibited narrow molecular weight distributions (Mw/Mn≤1.11) and as expected Mn's (see, Table 2).

The one-pot methodology described herein is applicable for the synthesis of precise stereo-diblock PLA of any block lengths' ratio, which are currently prepared by a laborious and less controlled two-step synthesis (see, for example, Tsuji et al. *Macromol. Mater. Eng.* 299, 430 (2014)). The possibility that epimerization or trans-esterification side reactions might be taking place was revoked by a diblock copolymerization run in which the workup was delayed by 6 hours and yet, neither MWD broadening nor stereoerrors were observed.

Differential scanning calorimetry (DSC) measurements of the stereo-diblock copolymers carried out on cast films revealed very similar melting transitions at 215-220° C. for all samples, consistent with a stereocomplex crystal phase, which was confirmed by X-ray analysis, as shown in FIG. 4. The crystallinity degree of the samples ranged from 40 to 60% (melting enthalpies=61-85 J/g).

The melting temperature (Tm) and enthalpy (ΔHm) are among the highest ever reported for stereo-diblock PLA copolymers. All samples were found to completely crystallize from the melt during the cooling DSC run, and the Tm's of the second heating were practically identical to those of the first heating with sample crystallinities remaining high (38-47%). No evidence for homocrystallization was found, even for the longer diblock samples.

Extending this methodology to a three-step sequential addition afforded isotactic stereo-triblock PLA copolymers. Full monomer consumption was observed within 15-30 minutes, giving rise to triblock copolymers of narrow MWD's and as-predicted Mn's, as well as precise isotactic blocks constitution (See FIG. 5C). Different combinations of blocks could be "dialed in" including identical blocks of various lengths, like 100L-b-100D-b-100L and 200L-b-200D-b-200L or short-long-short blocks like 150L-b-15D-b-150L (see, Table 2).

DSC analysis of the triblock enantiomers (LDL and DLD) having block lengths of 100 repeat units revealed that Tm's and ΔHm's (Tm of 206° C. for both, and ΔHm of 41 and 51 J/g for LDL and DLD, respectively) are lower than those of the typical diblock copolymers. This behavior is expected for copolymers having unpaired enantiomeric blocks which lead to defects for the stereocomplex crystallization. A 1:1 blend of these two enantiomeric triblock copolymers led to enhancement of both the Tm (211° C.) and ΔHm(55 J/g).

Consistently, isotactic stereo-tetrablock PLA copolymers could be prepared by a four-step sequential addition process in a total polymerization time of less than 60 minutes, and exhibited all the characteristics of precise copolymer structure. DSC analysis of stereo-tetrablock samples revealed that while their $T_m$'s were similar to those of the analogous triblock copolymers, their Hm were higher by 30% than those of triblocks on average. This behavior is consistent with copolymers of equal number of D-LA and L-LA repeat units.

The synthesis of isotactic PLA copolymers of penta-block, hexa-block and even octa-block sequences was also demonstrated. Analysis of the conversion of the monomers, and the MWD, Mn and stereoregularity of the polymers revealed that the penta-block copolymer (5×100) was still of very high precision according to all parameters with a very high degree of isotacticity of $P_m$>0.96.

The data presented herein indicate that a {ONNN}Mg—Cl complex as described herein is capable of forming block-copolymers of precise microstructures, and is by far the most living catalyst ever described for cyclic ester ring-opening polymerization and is comparable to the highest living catalysts for any polymerization (such as, for example, reported by Soeriyadi, et al. *J. Am. Chem. Soc.* 133, 11128 (2011).

The data presented herein show that novel poly(lactic acid) materials featuring isotactic stereo-block microstructures of unprecedented precision are obtainable by a one-pot sequential monomer addition to a truly-living polymerization catalyst based on the common and non-toxic metal magnesium. The methodology provided herein can be utilized for providing a wide range of tailor-made architectures. The disclosed process of preparing block copolymers exemplified herein can be modified, for example, by employing rac-LA or related cyclic esters, or by synthesizing more elaborate polymeric architectures which consist of more than a single polymeryl branch, by employing polyalcohols instead of benzyl alcohol, as exemplified in Example 4 hereinunder.

Example 3

Block-Polymerization of Lactide and Caprolactone Employing an Exemplary {ONNN}Mg-HMDS Complex General PLA-PCL Block Copolymerization Procedure:

To a solution of the {ONNN}Mg—X complex (pre-catalyst) (2 μmol) in dichloromethane (5 mL), benzyl alcohol or 1,4-benzenedimethanol (5 mol equivalents) were added and the reaction mixture was stirred at room temperature for 2 minutes. Then, ε-caprolactone (ε-CL) was added, followed by either D- or L-lactide, maintaining the necessary delay (e.g., 2-5 minutes) between each addition. The reaction was terminated by exposing to air and the volatiles were removed under vacuum. The tacticity and stereoregularity of the copolymer samples were determined by the homonuclear-decoupled $^1$H NMR spectrometry (CDCl$_3$, 500 MHz) and by $^{13}$C NMR (CDCl$_3$, 125 MHz).

Table 6 below presents the data obtained for block co-polymerization of D/L-LA and ε-CL, employing (R,R)-Lig$^1$Mg-HMDS, in dichloromethane at room temperature.

TABLE 6

| | Type | Composition | Interval (minute) | $M_n$ | PDI |
|---|---|---|---|---|---|
| 1. | Di Block | PCL(100)-b-L(100) | 7 | 40770 | 1.18 |
| 2. | Di Block | PCL(300)-b-L(300) | 9 | 101100 | 1.18 |
| 3. | Di Block | PCL(500)-b-L(500) | 10 | 178300 | 1.18 |
| 4. | Di Block | PCL(100)-b-D(100) | 7 | 39700 | 1.15 |
| 5. | Di Block | PCL(300)-b-D(300) | 7 | 105600 | 1.19 |
| 6. | Di Block | PCL(500)-b-D(500) | 7 | 192000 | 1.19 |
| 7. | Di Block | PCL(800)-b-D(800) | 8 | 317200 | 1.21 |
| 8. | Tri Block | L(100)-b-PCL(100)-b-L(100) | 6 | 81000 | 1.13 |
| 9. | Tri Block | D(100)-b-PCL(100)-b-D(100) | 5 | 64000 | 1.08 |

TABLE 6-continued

| | Type | Composition | Interval (minute) | $M_n$ | PDI |
|---|---|---|---|---|---|
| 10. | Tri Block | D(200)-b-PCL(200)-b-D(200) | 7 | 111000 | 1.12 |
| 11. | Tri Block | D(300)-b-PCL(300)-b-D(300) | 7 | 135380 | 1.16 |
| 12. | Tri Block | PCL(100)-b-D(100)-b-L(100) | 10 | 58700 | 1.08 |
| 13. | Tri Block | PCL(200)-b-D(200)-b-L(200) | 10 | 105500 | 1.09 |
| 14. | Tri Block | PCL(300)-b-D(300)-b-L(300) | 12 | 164000 | 1.10 |
| 15. | Tetra Blocks | PCL(100)-b-D(100)-b-L(100)-b-D(100) | 12 | 65000 | 1.10 |
| 16. | Penta Blocks | D(100)-b-L(100)-b-PCL(100)-b-L(100)-b-D(100) | 11 | 89560 | 1.09 |
| 17. | Penta Blocks | D(200)-b-L(200)-b-PCL(200)-b-L(200)-b-D(200) | 12 | 182400 | 1.10 |
| 18. | Penta Blocks | D(300)-b-L(300)-b-PCL(300)-b-L(300)-b-D(300) | 15 | 285500 | 1.06 |
| 19. | Penta Blocks | L(50)-b-D(50)-b-PCL(50)-b-D(50)-b-L(50) | 9 | 54100 | 1.13 |
| 20. | Penta Blocks | L(100)-b-D(100)-b-PCL(100)-b-D(100)-b-L(100) | 11 | 101300 | 1.17 |
| 21. | Penta Blocks | L(200)-b-D(200)-b-PCL(200)-b-D(200)-b-L(200) | 12 | 142500 | 1.10 |
| 22. | Penta Blocks | L(300)-b-D(300)-b-PCL(300)-b-D(300)-b-L(300) | 15 | 302500 | 1.12 |
| 23. | Penta Blocks | PCL(100)-b-L(100)-b-D(100)-b-L(100)-b-D(100) | 13 | 85800 | 1.10 |
| 24. | Hepta Blocks | L(50)-b-D(50)-b-L(50)-b-PCL(50)-b-L(50)-b-D(50)-b-L(50) | 10 | 82450 | 1.10 |
| 25. | Hepta Blocks | L(100)-b-D(100)-b-L(100)-b-PCL(100)-b-L(100)-b-D(100)-b-L(100) | 14 | 192000 | 1.12 |

The synthesis of stereo-diblock copolymers was performed by adding F-CL to a stirring mixture of {ONNN}Mg-HDMS and benzyl alcohol in dichloromethane, followed by addition of L-LA or D-LA after several minutes and eventual workup after an identical interval.

It was found that PLLA-PCL and PDLA-PCL diblock copolymers having identical block lengths repeat units were readily obtained by this one-pot synthesis. The two monomer enantiomers were fully consumed, and the polymer samples featured a perfectly regular stereo-diblock microstructure.

The three-step sequential addition afforded variable isotactic stereo-triblock copolymers: PCL-PLLA-PCL; PCL-PDLA-PCL; PCL-PLLA-PDLA. Different combinations of blocks could be "dialed in" including identical blocks of various lengths, or short-long-short blocks.

Consistently, stereo-tetrablock, penta-block and hepta-block copolymers have been prepared by a sequential addition process, and exhibited all the characteristics of precise copolymer structure.

The data presented herein indicate that a {ONNN}Mg-HDMS complex as described herein is capable of forming block-copolymers of precise microstructures, and is by far the most living catalyst ever described for cyclic ester ring-opening polymerization and is comparable to the highest living catalysts for any polymerization (such as, for example, reported by Soeriyadi, et al. *J. Am. Chem. Soc.* 133, 11128 (2011).

Notably, block-copolymers exhibiting exceptionally high molecular weight were obtained.

The data presented herein show that novel plastic materials featuring isotactic stereo-block microstructures of unprecedented precision and length are obtainable by a one-pot sequential monomer addition to a truly-living polymerization catalyst based on the common and non-toxic metal magnesium, opening the way for providing an even wide range of tailor-made architectures.

Example 4

Homo-Polymerization and Block-Polymerization Employing Sequential {ONNN}-Mg—X Complexes and a Polyalcohol Preliminary experiments were made for providing more elaborate polymeric architectures which consist of more than a single polymeryl branch, by employing polyalcohols such as poly(ethylene glycol) or pentaerythritol, instead of benzyl alcohol.

The PLA-PCL copolymers having PCL as middle block, see, entries 8-10 in table 7, were prepared using 1,4-benzenedimethanol.

Table 7 below presents the obtained data, and show full lactide (or lactide and caprolactone, entries 3,6) consumption, demonstrating the applicability of this methodology for attaining complex architectures of stereoblock copolymers.

TABLE 7

| | Catalyst | Alcohol | Composition | $M_n$ | PDI |
|---|---|---|---|---|---|
| 1 | Lig$^1$Mg—Cl | Pentaerythritol | C[CH$_2$—O-PLLA(100)]$_4$ | 36700 | 1.12 |
| 2 | Lig$^1$Mg—Cl | Pentaerythritol | C[CH$_2$—O-PLLA(100)-b-PDLA(100)]$_4$ | 72340 | 1.16 |
| 3 | Lig$^1$Mg-HDMS | Pentaerythritol | C[CH$_2$—O-PCL(100)]$_4$ | 43250 | 1.59 |
| 4 | Lig$^1$Mg—Cl | PEG2000 | PLLA(100)-b-PEG2000-b-PLLA(100) | 27000 | 1.09 |
| 5 | Lig$^1$Mg—Cl | PEG2000 | PDLA(100)-b-PLLA(100)-b-PEG2000-b-PLLA(100)-b-PDLA(100) | 41500 | 1.10 |
| 6 | Lig$^1$Mg-HDMS | PEG2000 | PLLA(100)-b-PCL(100)-b-PEG2000-b-PCL(100)-b-PLLA(100) | 58760 | 1.18 |

Example 5

Syntheses of Magnesium Complexes of Divergent {ONNN} Ligands

Syntheses of Divergent {ONNN} Ligands

Figure 7:
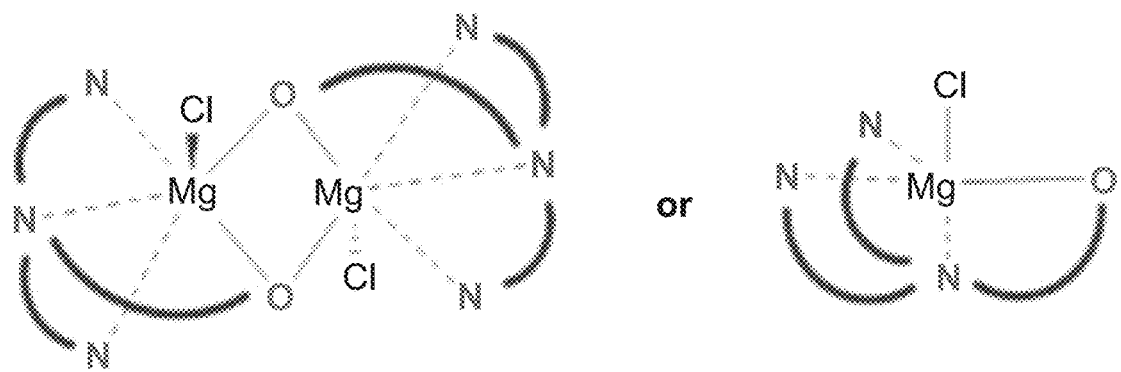
FIG. 7 presents a schematic illustration of a preparation of mononuclear and dinuclear magnesium complexes featuring one or two divergent {ONNN} ligand(s), respectively, according to exemplary embodiments of the present invention.

Divergent monoanionic ligands were prepared (Lig$^{2-6}$H, see, FIG. 7) having alkyl substituents of different steric bulk (H, Me, tBu, adamantly and cumyl) in the ortho- and para-positions of the phenolate arm. The ligands were readily synthesized by single-step procedures in high yields, by a modified reductive-amination reaction (Lig$^{2,4-6}$H) or by the Mannich reaction (Lig$^3$H), employing the commercially-available bis(2-pyridylmethyl) amine and a commercially- or readily-available substituted phenol/salicylaldehyde. The ligand precursors were obtained as colourless or yellow powders, and their identities were confirmed by NMR spectroscopy and high-resolution mass spectrometry.

Bis(2-pyridylmethyl)amine was purchased from TCI and used as received. Sodium triacetoxyborohydride was purchased from Strem and used as received. 3-Adamantyl-5-methylsalicylaldehyde, 3,5-bis(dimethylbenzyl)salicylaldehyde and the ligand precursors Lig$^{3'}$4H were synthesized following previously published procedures [K. Gademann et al., *Angew. Chem. Int. Ed.*, 2002, 41, 3059-3061; A. I. Kochnev et al., *Russ. Chem. Bull. Int. Ed.*, 2007, 56, 1125-1129; D. D. Cox and L. Que, *J. Am. Chem. Soc.*, 1988, 110, 8085-8092; M. J. L. Tschan et al., *Dalton Trans.*, 2014, 43, 4550-4564].

Synthesis of Lig$^1$H

This compound was synthesized by modification of a literature procedure [G. P. Connor et al., *Inorg. Chem.*, 2014, 53, 5408-5410].

To a solution of bis(2-pyridylmethyl)amine (720 mg, 3.61 mmol) in dichloromethane (40 mL), sodium triacetoxyborohydride (990 mg, 4.67 mmol) was added at 0° C. The mixture was stirred at 0° C. for 1 hour, after which salicylaldehyde (440 mg, 3.61 mmol) was added. After additional 4 hours stirring at room temperature, the reaction was quenched by adding NaHCO$_3$10% solution (20 mL). The organic phase was separated and dried over Na$_2$SO$_4$. The solvent was removed under vacuum and the crude product was purified by passing through a plug of silica with ethyl acetate as eluent. A yellow oil was obtained. The overall yield was 82%.

$^1$H NMR (CDC$_3$, 500 MHz): δ 11.09 (brs, 1H, OH), 8.57 (d, 2H, J=4.6 Hz, ArH), 7.62 (td, 2H, J=1.7 Hz, J=7.7 Hz, ArH), 7.34 (d, 2H, J=7.8 Hz, ArH), 7.19-7.14 (m, 3H, ArH), 7.06 (dd, 1H, J=1.3 Hz, J=7.6 Hz, ArH), 6.91 (dd, 1H, J=0.7 Hz, J=8.0 Hz, ArH), 6.77 (td, 1H, J=1.0 Hz, J=7.4 Hz, ArH), 3.88 (s, 4H, CH$_2$), 3.80 (s, 2H, CH$_2$).

$^{13}$C NMR (CDCl$_3$, 125 MHz): δ 158.43 (C), 157.73 (C), 149.07 (CH), 136.91 (CH), 130.30 (CH), 129.20 (CH), 123.37 (CH), 122.95 (C), 122.36 (CH), 119.00 (CH), 116.68 (CH), 59.25 (CH$_2$), 57.10 (CH$_2$).

HRMS (ESI): Calc for C$_{19}$H$_{19}$N$_3$O: 305.1528, found: 328.1428 (M−Na+).

Synthesis of Lig$^5$H

This compound was synthesized according to the procedure described above employing 3-adamantyl-5-methylsalicylaldehyde. A yellow solid was obtained in an overall yield of 90%.

$^1$H NMR (CDC$_3$, 500 MHz): δ 10.45 (brs, 1H, OH), 8.56 (d, 2H, J=4.6 Hz), 7.63 (td, 2H, J=1.7 Hz, J=7.7 Hz, ArH), 7.33 (d, 2H, J=7.8 Hz, ArH), 7.15 (dd, 2H, J=4.8 Hz, J=7.6 Hz, ArH), 6.94 (d, 1H, J=1.6 Hz, ArH), 6.71 (d, 1H, J=1.4 Hz, ArH), 3.85 (s, 4H, CH$_2$), 3.76 (s, 2H, CH$_2$), 2.23 (s, 3H, CH$_3$), 2.20 (brs, 6H, Ad), 2.08 (brs, 6H, Ad), 1.83 (d, 3H, J=12.0 Hz, Ad), 1.78 (d, 3H, J=12.0 Hz, Ad).

$^{13}$C NMR (CDCl$_3$, 125 MHz): δ 158.23 (C), 154.40 (C), 149.14 (CH), 136.84 (C), 136.76 (CH), 128.45 (CH), 127.21 (C), 126.93 (CH), 123.76 (CH), 122.83 (C), 122.33 (CH), 59.45 (CH$_2$), 58.03 (CH$_2$), 40.68 (C), 40.54 (CH$_2$), 37.41 (CH$_2$), 36.98 (CH), 29.40 (CH$_2$), 20.92 (CH$_3$).

HRMS (ESI): Calc for C$_3$H$_{35}$N$_3$O: 453.2780, found: 454.2854 (MH+).

Synthesis of Lig$^6$H

This compound was synthesized according to the procedure described above employing 3,5-bis(dimethylbenzyl) salicylaldehyde. A yellow solid was obtained in an overall yield of 94%.

$^1$H NMR (CDC$_3$, 500 MHz): δ 10.34 (brs, 1H, OH), 8.45 (d, 2H, J=4.5 Hz, ArH), 7.47 (td, 2H, J=1.8 Hz, J=7.7 Hz, ArH), 7.26-7.21 (m, 6H, ArH), 7.18-7.14 (m, 3H, ArH), 7.14-7.08 (m, 3H, ArH), 6.92 (d, 2H, J=7.8 Hz, ArH), 6.76 (d, 1H, J=2.3 Hz, ArH), 3.68 (s, 2H, CH$_2$), 3.67 (s, 2H, CH$_2$), 1.68 (s, 6H, CH$_3$), 1.67 (s, 6H, CH$_3$).

$^{13}$C NMR (CDC$_3$, 125 MHz): δ 157.88 (C), 153.54 (C), 151.94 (C), 151.54 (C), 148.95 (CH), 140.02 (C), 136.81 (CH), 135.39 (C), 128.01 (CH), 127.74 (CH), 126.90 (CH), 126.67 (CH), 125.93 (CH), 125.53 (CH), 125.17 (CH), 124.71 (CH), 124.02 (CH), 122.25 (CH), 121.83 (C), 59.15 (CH$_2$), 58.24 (CH$_2$), 42.60 (C), 42.25 (C), 31.25 (CH$_3$), 29.63 (CH$_3$).

HRMS (ESI): Calc for C$_{37}$H$_{39}$N$_3$O: 541.3093, found: 542.3177 (MH+).

Syntheses of Divergent {ONNN}-Mg—Cl Complexes

Figure 8:
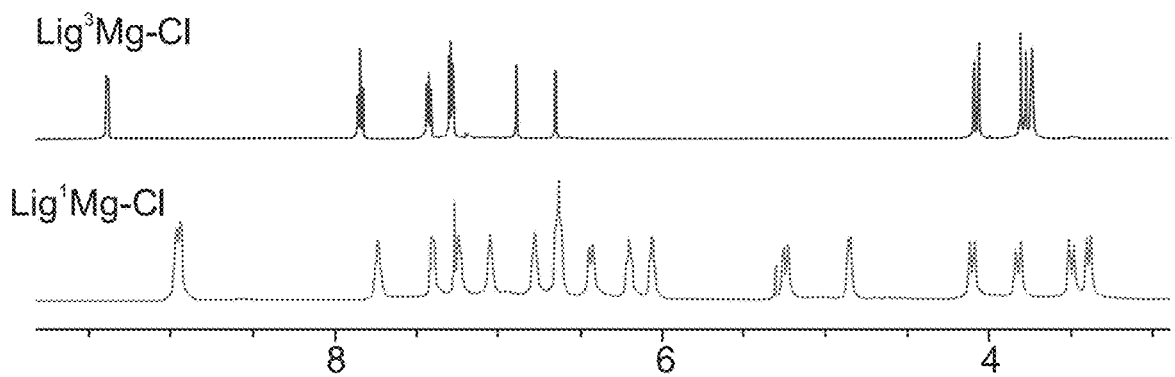
FIG. 8 presents $^1$H-NMR spectra (CDC$_3$, 3-9.5 ppm) of an exemplary mononuclear magnesium complex (top panel, Lig$^4$Mg—Cl) and an exemplary dinuclear (bottom panel, [(µ-Lig$^2$)Mg—Cl]$_2$) magnesium complex, according to some embodiments of the present invention.
Figure 9A:
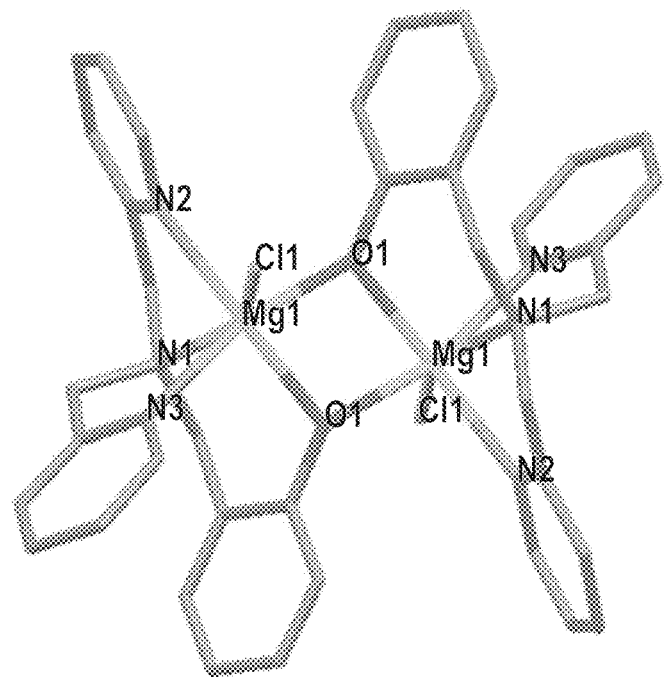
FIGS. 9A-9B present the crystallographic structures of [(µ-Lig$^2$)Mg—Cl]$_2$ (FIG. 9A) and [(µ-Lig$^3$)Mg—Cl]$_2$.
Figure 9B:
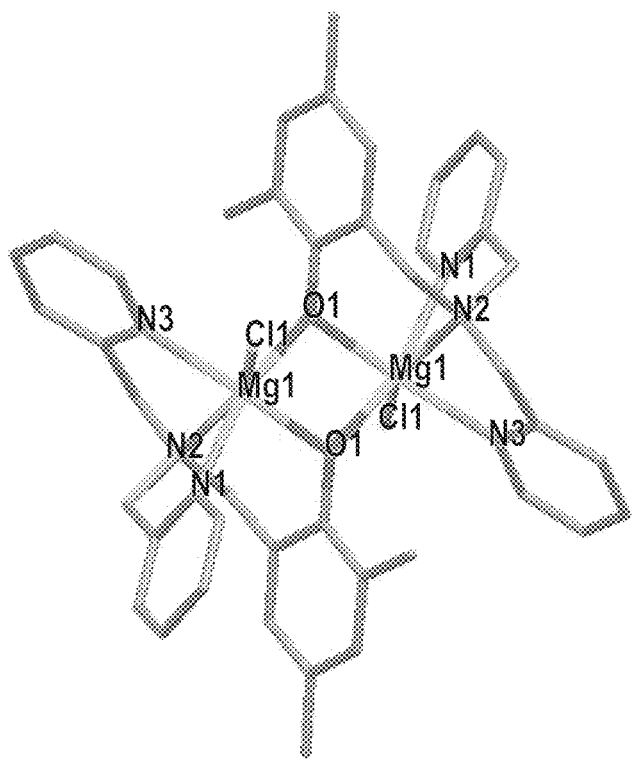

The bulky ligand precursors Lig$^4$-6H were reacted with one mol equivalent of benzyl magnesium chloride in toluene at room temperature, according to a previously described procedure [T. Rosen et al, *J. Am. Chem. Soc.*, 2016, 138, 12041-12044] and yielded the corresponding chloro-magnesium complexes as yellow powders in high to quantitative yields (see, FIG. 7). $^1$H-NMR spectroscopy (in CDCl$_3$) revealed a single set of peaks signifying mononuclear complexes of the type Lig"Mg—Cl obtained as single stereoisomers of Cs-symmetry (FIG. 8, top panel). The magnesium complexes of the non-bulky divergent ligand precursors Lig$^{2,3}$H were prepared likewise, and yielded the corresponding complexes in high yields as yellow powders as well. The $^1$H-NMR spectra of these two complexes displayed different characteristics including two sets of peaks for the two pyridine rings and three AB systems for the three CH$_2$ bridges. This reduced symmetry is attributed to the formation of dinuclear magnesium complexes of the type [(µ-Lig") Mg—Cl]$_2$ for these sterically non-encumbered ligands (see, FIG. 7, FIG. 8, bottom panel, FIGS. 9A and 9B) having either Ci- or Cs-averaged symmetry.

Single crystals of the complexes [(µ-Lig$^2$)Mg—Cl]$_2$ and [(µ-Lig$^3$)Mg—Cl]$_2$ were grown from dichloromethane solutions at 35° C., and their molecular structures were determined by X-ray diffraction studies. The two complexes were isostructural, featuring dinuclear chloro-magnesium complexes of octahedral geometry in which the phenolate oxygens of the two ligand units bridge between the two magnesium atoms, thus supporting the NMR findings (see, FIGS. 9A and 9B). A crystallographic C$_1$-symmetry of the two complexes dictates a planar Mg—O—Mg—O ring, and the Mg—O(Ph) bond lengths are only slightly different, being 2.032° A and 2.061° A for [(µ-Lig$^2$)Mg—Cl]$_2$ and 2.026° A and 2.062° A for [(µ-Lig$^1$)Mg—Cl]$_2$.

The molecular structure of previously reported magnesium enolato complex of Lig$^4$ featured a pentacoordinate mononuclear magnesium centre, supporting a mononuclear structure of Lig$^{4-6}$Mg—Cl. Further evidence for these different coordination modes was provided by high-resolution mass spectrometry (HRMS) analysis, which supported the formation of the proposed mononuclear and dinuclear structures for Lig$^{4-6}$Mg—Cl and Lig$^{2,3}$Mg—Cl, respectively.

Synthesis of [(μ-Lig$^2$)Mg—Cl]$_2$

To a stirred solution of Lig$^2$H (80 mg, 0.26 mmol) in toluene (2 mL), was added a solution of BnMgCl (0.26 mL, 1M diethyl ether solution) drop-wise. The resulting mixture was stirred at room temperature for 30 minutes until a precipitate appeared. The solvent was thereafter removed under vacuum and the residue was washed with pentane to give a yellow solid in 61% yield. Crystals suitable for X-ray diffraction were grown from dichloromethane solution at −30° C.

$^1$H NMR (CDC$_3$, 500 MHz): δ 8.95 (d, 2H, J=14.3 Hz, ArH), 7.73 (t, 1H, J=7.2 Hz, ArH), 7.35 (d, 1H, J=7.3 Hz, ArH), 7.23 (t, 1H, J=7.0 Hz, ArH), 7.04 (t, 1H, J=5.8 Hz, ArH), 6.77 (t, 1H, J=5.8 Hz, ArH), 6.62 (t, 2H, J=8.3 Hz, ArH), 6.42 (d, 1H, J=12.3 Hz, CH$_2$), 6.19 (t, 1H, J=7.0 Hz, ArH), 6.05 (t, 1H, J=7.0 Hz, ArH), 5.23 (d, 1H, J=15.0 Hz, CH$_2$), 4.85 (d, 1H, J=7.6 Hz, ArH), 4.10 (d, 1H, J=15.1 Hz, CH$_2$), 3.82 (d, 1H, J=15.0 Hz, CH$_2$), 3.49 (d, 1H, J=15.1 Hz, CH$_2$), 3.38 (d, 1H, J=12.2 Hz, CH$_2$).

$^{13}$C NMR (CDC$_3$, 125 MHz): δ 163.61(C), 156.45 (C), 156.33 (C), 151.69 (CH), 150.92 (CH), 138.40(CH), 137.14 (CH), 129.97 (CH), 128.25 (CH), 127.65 (C), 122.99 (CH), 122.72 (CH), 122.17 (CH), 120.68 (CH), 119.08 (CH), 115.40 (CH), 64.50 (CH$_2$), 61.57 (CH$_2$), 61.49 (CH$_2$).

HRMS (APPI): Calc for C$_{38}$H$_{36}$Cl$_2$Mg$_2$N$_6$O$_2$: 726.1978, found: 691.2275 ([M−Cl]$^+$).

Crystal Data for Complex [(u-Lig$^2$)Mg—Cl]$_2$·2CH$_2$Cl$_2$. C$_{19}$H$_{18}$ClN$_3$OMg, 2CH$_2$Cl$_2$; M=533.97; monoclinic; space group C$_2$/c; a=24.0022(18) Å, b=8.6136(6) Å, c=25.556(3) Å, =116.047(3)°, V=4746.9(7) Å$^3$; T=110(2) K; Z=8; Dc=1.494 g cm$^{-3}$; (MoKα)=0.658 mm$^{-1}$; R1=0.0516 and wR2=0.0972 for 4733 reflections with I>2σ (I); R1=0.0391 and wR2=0.0912 for all 3904 unique reflections. CCDC No. 1537631. See, FIG. 9A.

Synthesis of [(μ-Lig$^3$)Mg—Cl]$_2$

To a stirred solution of Lig$^3$H (76 mg, 0.23 mmol) in toluene (2 mL), was added a solution of BnMgCl (0.23 mL, 1M diethyl ether solution) drop-wise. The resulting mixture was stirred at room temperature for 1 hour until a precipitate appeared. The solvent was thereafter removed under vacuum and the residue was washed with pentane to give a yellow solid in 74% yield.

$^1$H NMR (CDC$_3$, 500 MHz): δ 9.25 (d, 1H, J=5.7 Hz, ArH), 9.12 (d, 1H, J=5.7 Hz, ArH), 7.69 (td, 1H, J=1.7 Hz, J=7.6 Hz, ArH), 7.28 (d, 1H, J=7.7 Hz, ArH), 7.16 (td, 1H, J=1.7 Hz, J=7.6 Hz, ArH), 7.07 (t, 1H, J=6.4 Hz, ArH), 6.76 (t, 1H, J=6.4 Hz, ArH), 6.56 (d, 1H, J=11.9 Hz, CH$_2$), 6.54 (d, 1H, J=2.0 Hz, ArH), 6.37 (d, 1H, J=7.7 Hz, ArH), 5.96 (d, 1H, J=1.6 Hz, ArH), 4.92 (d, 1H, J=14.9 Hz, CH$_2$), 3.95 (d, 1H, J=14.9 Hz, CH$_2$), 3.61 (d, 1H, J=14.9 Hz, CH$_2$), 3.40 (d, 1H, J=15.1 Hz, CH$_2$), 3.37 (d, 1H, J=13.9 Hz, CH$_2$), 1.94 (s, 3H, CH$_3$), 0.95 (s, 3H, CH$_3$).

$^{13}$C NMR (CDCl$_3$, 125 MHz): δ 158.63 (C), 156.75 (C), 155.91(C), 152.25 (CH), 149.70 (CH), 138.49 (CH), 136.62 (CH), 130.97 (CH), 129.13 (CH), 126.85 (C), 126.79 (C), 124.08 (C), 123.41 (CH), 122.75 (CH), 121.65 (CH), 120.06 (CH), 65.24 (CH$_2$), 62.29 (CH$_2$), 61.47 (CH$_2$), 20.33 (CH$_3$), 14.21 (CH$_3$).

HRMS (APPI): Calc for C$_{42}$H$_{44}$Cl$_2$Mg$_2$N$_6$O$_2$: 782.2604, found: 747.2916 ([M−Cl]$^+$).

Crystal Data for Complex [(μ-Lig$^3$)MgCl]$_2$·5CH$_2$Cl$_2$. C$_{42}$H$_{44}$Cl$_2$N$_6$O$_2$Mg$_2$, 5CH$_2$Cl$_2$; M=1208.98; monoclinic; space group C$_2$/c; a=27.2980(18) Å, b=14.9001(12) Å. c=16.8775(10) Å. β=124.630(2)°, V=5648.6(7) Å$^3$; T=110(2) K; Z=4; Dc=1.422 g cm$^{-3}$; (Mo Kα)=0.653 mm$^{-1}$; R1=0.0702 and wR2=0.0567 for 5026 reflections with I>2σ (I); R1=0.1604 and wR2=0.1488 for all 4116 unique reflections. CCDC No. 1537632. See, FIG. 9B.

Synthesis of Lig$^4$Mg—Cl

To a stirred solution of Lig$^4$H (92 mg, 0.22 mmol) in toluene (2 mL), was added a solution of BnMgCl (0.22 mL, 1M diethyl ether solution) drop-wise. The resulting mixture was stirred at room temperature for 1 hour until a precipitate appeared. The solvent was thereafter removed under vacuum and the residue was washed with pentane to give a yellow solid in 90% yield.

$^1$H NMR (CDC$_3$, 500 MHz): δ 9.35 (d, 2H, J=5.1 Hz, ArH), 7.84 (td, 2H, J=1.4 Hz, J=7.5 Hz, ArH), 7.41 (t, 2H, J=6.5 Hz, ArH), 7.29 (d, 2H, J=7.7 Hz, ArH), 7.17 (d, 1H, J=2.5 Hz, ArH), 6.80 (d, 1H, J=2.5 Hz, ArH), 4.09 (d, 2H, J=15.7 Hz, CH$_2$), 3.82 (d, 2H, J=15.7 Hz, CH$_2$), 3.75 (brs, 2H, CH$_2$), 1.43 (s, 9H, C(CH$_3$)$_3$), 1.24 (s, 9H, C(CH$_3$)$_3$).

$^{13}$C NMR (CDCl$_3$, 125 MHz): δ 163.35 (C), 157.00 (C), 151.75 (CH), 139.99 (CH), 138.58 (C), 134.07 (C), 129.19 (CH), 128.38 (CH), 125.45 (CH), 125.33 (CH), 124.30 (CH), 124.16 (CH), 123.18 (CH), 120.99 (C), 60.92 (CH$_2$), 58.45 (CH$_2$), 35.36 (C), 33.95 (C), 32.06 (CH$_3$), 29.78 (CH$_3$).

HRMS (APPI): Calc for C$_{27}$H$_{34}$N$_3$OClMg: 475.2241, found: 476.2302 (MH+).

Synthesis of Lig$^5$Mg—Cl

To a stirred solution of Lig$^5$H (104 mg, 0.23 mmol) in toluene (2 mL), was added a solution of BnMgCl (0.23 mL, 1M diethyl ether solution) drop-wise. The resulting mixture was stirred at room temperature for 1 hour until a precipitate appeared. The solvent was thereafter removed under vacuum and the residue was washed with pentane to give a yellow solid in 91% yield.

$^1$H NMR (CDC$_3$, 500 MHz): δ 9.38 (d, 2H, J=4.9 Hz, ArH), 7.84 (td, 2H, J=1.7 Hz, J=7.7 Hz, ArH), 7.42 (t, 2H, J=6.5 Hz, ArH), 7.28 (d, 2H, J=7.8 Hz, ArH), 6.88 (d, 1H, J=2.1 Hz, ArH), 6.64 (d, 1H, J=2.0 Hz, ArH), 4.07 (d, 2H, J=15.8 Hz, CH$_2$), 3.79 (d, 2H, J=15.7 Hz, CH$_2$), 3.73 (brs, 1H, CH$_2$), 2.21 (d, 6H, J=2.0 Hz, Ad), 2.18 (s, 3H, CH$_3$), 2.04 (brs, 3H, Ad), 1.87 (d, 3H, J=11.3 Hz, Ad), 1.72 (d, 3H, J=11.7 Hz, Ad).

$^{13}$C NMR (CDC$_3$, 125 MHz): δ 163.43 (C), 156.99 (C), 151.85, (CH), 140.03 (CH), 139.74 (C), 129.19 (CH), 129.11 (CH), 128.38 (CH), 127.80 (CH), 125.45 (CH), 124.20 (CH), 123.16 (CH), 122.13 (C), 120.63 (C), 60.35 (CH$_2$), 58.29 (CH$_2$), 40.21 (CH$_2$), 37.61 (CH$_2$), 37.21 (C), 29.59 (CH$_3$), 20.89 (CH).

HRMS (APPI): Calc for C$_{30}$H$_{34}$N$_3$OClMg: 511.2241, found: 512.2300 (MH$^+$).

Synthesis of Lig$^6$Mg—Cl

To a stirred solution of Lig$^6$H (110 mg, 0.20 mmol) in toluene (2 mL), was added a solution of BnMgCl (0.20 mL, 1M diethyl ether solution) drop-wise. The resulting mixture was stirred at room temperature for 1 hour until a precipitate appeared. The solvent was thereafter removed under vacuum and the residue was washed with pentane to give a yellow solid in 88% yield.

$^1$H NMR (CDC$_3$, 500 MHz): δ 9.11 (d, 2H, J=4.5 Hz, ArH), 7.79 (td, 2H, J=1.7 Hz, J=7.7 Hz, ArH), 7.36 (t, 2H, J=6.2 Hz, ArH), 7.25-7.18 (m, 7H, ArH), 7.13-7.11 (m, 3H, ArH), 6.77 (t, 2H, J=7.3 Hz, ArH), 6.63 (d, 1H, J=2.5 Hz, ArH), 6.58 (t, 1H, J=7.2 Hz, ArH), 3.75 (d, 2H, J=15.5 Hz, CH$_2$), 3.58 (d, 4H, J=15.5 Hz, CH$_2$), 1.69 (brs, 6H, CH$_3$), 1.65 (s, 6H, CH$_3$).

$^{13}$C NMR (CDCl$_3$, 125 MHz): δ 162.23 (C), 156.68 (C), 152.91 (C), 152.76 (C), 151.96 (CH), 139.73 (CH), 138.77 (C), 133.24 (C), 127.74 (CH), 127.22 (CH), 126.99 (CH), 126.74 (CH), 126.08 (CH), 126.04 (CH), 125.13 (CH), 123.87 (CH), 123.83 (CH), 122.88 (CH), 121.07 (C), 60.00 (CH$_2$), 42.37 (C), 42.30 (C), 31.38 (CH$_3$).

HRMS (APPI): Calc for C$_{37}$H$_{38}$N$_3$OClMg: 599.2554, found: 600.2634 (MH+).

Example 6

Homo-Polymerization and Block-Polymerization of PLa Employing Lig$^{2-6}$Mg—Cl General Homo-Polymerization Procedure:

To a solution of the divergent Mg complex (0.01 mmol) in dichloromethane (5 mL), benzyl alcohol (either none or 0.01-0.04 mmol) was added, and the reaction mixture was stirred at room temperature for 2 minutes. Then, L-lactide (432 mg, 3 mmol) was added, and the reaction was stirred at room temperature. After the desired time, the reaction was terminated by exposing to air and the volatiles were removed under vacuum.

General Block-Polymerization Procedure:

To a solution of the divergent Mg complex (0.01 mmol) in dichloromethane (5 mL), benzyl alcohol (2 mol equivalents) was added and the reaction mixture was stirred at room temperature for 2 minutes. Then, D-Lactide and L-Lactide were sequentially added, each separately, maintaining the necessary delay (5-10 minutes) between each addition. The reaction was terminated by exposing to air and the volatiles were removed under vacuum.

Polymerization Results:

Tables 8 and 9 present the data obtained for homo-polymerization of L-LA (Table 8) and block co-polymerization of L-LA and D-LA (Table 9) employing Lig$^{2-6}$Mg—Cl in dichloromethane at room temperature.

TABLE 8

| Entry | Initiator | [I]/[BnOH]/[LA] | Time (min) | Conv.$^a$ | Mn calc$^b$ | Mn$^c$ | PDI$^d$ |
|---|---|---|---|---|---|---|---|
| 7. | [(μ-Lig$^2$)Mg—Cl]$_2$ | 1/1/300 | 15 | 0.90 | 38,880 | 30,397 | 1.08 |
| 8. | [(μ-Lig$^2$)Mg—Cl]$_2$ | 1/2/600 | 20 | 0.91 | 39,312 | 32,478 | 1.08 |
| 9. | [(μ-Lig$^2$)Mg—Cl]$_2$ | 1/10/1000 | 20 | 0.97 | 13,968 | 15,023 | 1.05 |
| 10. | [(μ-Lig$^3$)Mg—Cl]$_2$ | 1/1/300 | 15 | 0.88 | 38,016 | 39,150 | 1.07 |
| 11. | [(μ-Lig$^3$)Mg—Cl]$_2$ | 1/10/1000 | 20 | 0.90 | 12,960 | 10,780 | 1.06 |
| 12. | Lig$^4$Mg—Cl | 1/1/300 | 5 | 0.98 | 42,336 | 33,940 | 1.04 |
| 13. | Lig$^4$Mg—Cl | 1/10/1000 | 5 | 0.99 | 14,256 | 13,860 | 1.04 |
| 14. | Lig$^4$Mg—Cl | 1/1/1000 | 10 | 0.98 | 141,120 | 86,597 | 1.06 |
| 15. | Lig$^5$Mg—Cl | 1/1/300 | 2 | 0.98 | 42,336 | 46,527 | 1.08 |
| 16. | Lig$^5$Mg—Cl | 1/4/600 | 3 | 0.98 | 21,168 | 20,155 | 1.04 |
| 17. | Lig$^5$Mg—Cl | 1/1/1000 | 4 | 0.97 | 139,680 | 111,510 | 1.05 |
| 18. | Lig$^5$Mg—Cl | 1/10/1000 | 2 | 0.98 | 14,112 | 13,540 | 1.04 |
| 19. | Lig$^5$Mg—Cl | 1/1/2000 | 5 | 0.96 | 276,480 | 271,452 | 1.06 |
| 20. | Lig$^6$Mg—Cl | 1/1/300 | 5 | 0.95 | 41,040 | 35,860 | 1.08 |
| 21. | Lig$^6$Mg—Cl | 1/10/1000 | 10 | 0.95 | 13,680 | 12,950 | 1.04 |
| 22. | Lig$^6$Mg—Cl | 1/1/1000 | 10 | 0.91 | 131,140 | 123,450 | 1.07 |
| 23. | [(μ-Lig$^2$)Mg—Cl]$_2$ | 1/0/300 | 15 | 0.42 | 18.144 | 27,369 | 1.20 |
| 24. | [(μ-Lig$^3$)Mg—Cl]$_2$ | 1/0/300 | 15 | 0.87 | 37,584 | 103,378 | 1.27 |
| 25. | Lig$^4$Mg—Cl | 1/0/300 | 5 | 0.93 | 40,176 | 309,139 | 1.26 |
| 26. | Lig$^5$Mg—Cl | 1/0/300 | 10 | 0.93 | 40,176 | 297,372 | 1.20 |
| 27. | Lig$^6$Mg—Cl | 1/0/300 | 5 | 0.88 | 38,016 | 211,172 | 1.35 |

$^a$Determined by $^1$H NMR spectroscopy (500 MHz).
$^b$Calculated from monomer conversion assuming full benzyl alcohol participation or full catalyst activation. Values are given in g mol−1
$^c$Mn was determined by GPC analysis with THF as eluent calibrated with polystyrene standards and multiplied by a correction factor of 0.58.
$^d$PDI: polydispersity index (Mw/Mn). Determined by GPC analysis.

TABLE 9

| Initiator | Type | Composition | Time (min)$^b$ | Conv.$^c$ | Pm$^d$ | Mn calc$^e$ | Mn$^f$ | PDI$^g$ |
|---|---|---|---|---|---|---|---|---|
| Lig$^4$Mg—Cl | Di Block | L(100)-b-D(100) | 10 | >0.98 | >0.99 | 28800 | 26700 | 1.11 |
| Lig$^4$Mg—Cl | Di Block | L(200)-b-D(200) | 10 | >0.98 | >0.99 | 57600 | 62670 | 1.20 |
| Lig$^4$Mg—Cl | Di Block | L(300)-b-D(300) | 20 | >0.98 | >0.99 | 86400 | 66480 | 1.34 |
| Lig$^5$Mg—Cl | Di Block | L(100)-b-D(100) | 10 | >0.98 | >0.99 | 28800 | 22900 | 1.06 |
| Lig$^5$Mg—Cl | Di Block | L(200)-b-D(200) | 10 | >0.98 | >0.99 | 57600 | 62900 | 1.04 |
| Lig$^5$Mg—Cl | Di Block | L(300)-b-D(300) | 11 | >0.98 | >0.99 | 86400 | 85800 | 1.04 |
| Lig$^5$Mg—Cl | Di Block | L(400)-b-D(400) | 12 | >0.98 | >0.99 | 115200 | 113670 | 1.06 |

TABLE 9-continued

| Initiator | Type | Composition | Time (min)[b] | Conv.[c] | Pm[d] | Mn calc[e] | Mn[f] | PDI[g] |
|---|---|---|---|---|---|---|---|---|
| Lig[5]Mg—Cl | Di Block | L(500)-b-D(500) | 13 | >0.98 | >0.99 | 144000 | 149110 | 1.07 |
| Lig[5]Mg—Cl | Di Block | L(800)-b-D(800) | 20 | >0.98 | >0.99 | 228100 | 202300 | 1.09 |
| Lig[5]Mg—Cl | Tri Block | L(100)-b-D(100)-b-L(100) | 15 | >0.98 | 0.98 | 43200 | 45860 | 1.08 |
| Lig[5]Mg—Cl | Tri Block | L(200)-b-D(200)-b-L(200) | 16 | >0.98 | 0.98 | 86400 | 88940 | 1.13 |
| Lig[5]Mg—Cl | Tri Block | L(300)-b-D(300)-b-L(300) | 18 | >0.98 | 0.98 | 129600 | 120590 | 1.12 |
| Lig[5]Mg—Cl | Tetra Block | L(100)-b-D(100)-b-L(100)-b-L(100) | 22 | >0.98 | 0.97 | 57600 | 64690 | 1.10 |
| Lig[5]Mg—Cl | Tetra Block | L(200)-b-D(200)-b-L(200)-L(200) | 24 | >0.98 | 0.96 | 115200 | 104230 | 1.13 |
| Lig[5]Mg—Cl | Tetra Block | L(300)-b-D(300)-b-L(300)-b-L(300) | 24 | >0.98 | 0.96 | 172800 | 166100 | 1.10 |

[b]Total polymerization time given in minutes. 5-15 minutes were maintained between each monomer addition, depending on the monomer amount and length of polymer chain.
[c]Determined by $^1$H NMR spectroscopy (500 MHz).
[d]Pmeso: the probability of a meso linkage between lactide units. Determined by the $^1$H homonuclear-decoupled NMR spectrometry (CDCl$_3$, 500 MHz) and by $^{13}$C NMR (CDCl$_3$, 125 MHz).
[e]Calculated from monomer conversion assuming full benzyl alcohol participation. Values are given in g mol−1
[f]Mn was determined by GPC analysis with CHCl3 as eluent calibrated with polystyrene standards and multiplied by a correction factor of 0.58.
[g]PDI: polydispersity index (Mw/Mn). Determined by GPC analysis.

Tables 10-12 below present the DSC data of various stereodiblocks (Table 10), stereotriblock (Table 11) and stereotetrablocks (Table 12) obtained with Lig$^{4,5}$Mg—Cl.

TABLE 10

DSC analysis of stereo-diblocks.

| | | First run | | Cooling | | | Second run | |
|---|---|---|---|---|---|---|---|---|
| Initiator | Composition | Tm | ΔHm | Tc | ΔHc | Tg | Tc/ΔHc | Tm | ΔHm |
| Lig[4]Mg—Cl | L(100)-b-D(100) | 213 | 75 | 140 | 58 | 56 | — | 212 | 58 |
| Lig[4]Mg—Cl | L(200)-b-D(200) | 213 | 64 | 117 | 47 | 56 | — | 211 | 48 |
| Lig[5]Mg—Cl | L(100)-b-D(100) | 212 | 59 | 132 | 46 | 58 | — | 210 | 42 |
| Lig[5]Mg—Cl | L(200)-b-D(200) | 211 | 66 | 135 | 52 | 62 | — | 213 | 50 |
| Lig[5]Mg—Cl | L(300)-b-D(300) | 214 | 76 | 127 | 49 | 58 | — | 205 | 51 |
| Lig[5]Mg—Cl | L(400)-b-D(400) | 210 | 87 | 139 | 60 | 59 | 106/7 | 213 | 61 |
| Lig[5]Mg—Cl | L(500)-b-D(500) | 214 | 79 | 153 | 54 | 58 | 101/3 | 211 | 51 |
| Lig[5]Mg—Cl | L(800)-b-D(800) | 214 | 67 | 154 | 43 | 57 | — | 216 | 44 |

TABLE 11

DSC analysis of stereo-triblocks.

| | | First run | | Cooling | | | Second run | |
|---|---|---|---|---|---|---|---|---|
| Initiator | Composition | Tm | ΔHm | Tc | ΔHc | Tg | Tc/ΔHc | Tm | ΔHm |
| Lig[5]Mg—Cl | L(100)-b-D(100)-b-L(100) | 202 | 36 | 106 | 4 | 55 | 99/25 | 196 | 29 |
| Lig[5]Mg—Cl | L(200)-b-D(200)-b-L(200) | 205 | 41 | 115 | 23 | 58 | 98/12.5 | 200 | 33 |
| Lig[5]Mg—Cl | L(300)-b-D(300)-b-L(300) | 201 | 40 | 108 | 11 | 58 | 101/21.3 | 197 | 31 |

TABLE 12

DSC data of stereo-tetrablocks.

| Initiator | Composition | First run | | Cooling | | | Second run | | |
|---|---|---|---|---|---|---|---|---|---|
| | | Tm | ΔHm | Tc | ΔHc | Tg | Tc/ΔHc | Tm | ΔHm |
| Lig$^5$Mg—Cl | L(100)-b-D(100)-b-L(100)-b-D(100) | 202 | 49 | 115 | 22 | 59 | 97/21 | 204 | 43 |
| Lig$^5$Mg—Cl | L(200)-b-D(200)-b-L(200)-b-D(200) | 205 | 56 | 119 | 37 | 57 | 97/9 | 201 | 39 |
| Lig$^5$Mg—Cl | L(300)-b-D(300)-b-L(300)-b-D(300) | 179 | 18 | — | — | 57 | 140/5 | 185 | 6 |

Polymerization runs were performed in dichloromethane solution at RT by adding the lactide to the Lig$^n$Mg—Cl complex as catalyst and benzyl alcohol as initiator. Under these conditions, polymerization of 300 mol equivalents of lactide by the mononuclear complexes Lig$^{4-6}$Mg—Cl led to almost full consumption of the monomer within 2-5 minutes (See Table 8). These complexes represent some of the highest activities ever reported for lactide polymerization.

The PLLA samples obtained were characterized by gel permeation chromatography (GPC) analysis and were found to have remarkably low PDI values of ≤1.08, with molecular weights (Mn) in agreement with the monomer/initiator molar ratios. The performance of these catalysts was also explored under 'immortal conditions', (namely, under initiator/catalyst ratio>1, which may lead to the production of more than a single polymer chain per catalyst unit) which led to PLLA samples with very narrow PDIs and $M_n$ values consistent with monomer/benzyl alcohol initiator ratios. Monomer loadings of up to 2000 mol equivalents were attempted giving almost full consumption after 5 minutes, and yielding monodisperded PLLA of high Mn. These divergent {ONNN}Mg—Cl complexes were found to be highly active ROP catalysts of L-LA even in the absence of benzyl alcohol.

Stereo-di-block copolymers having block lengths of up to 500 repeat units each were easily prepared in short periods of time of about 10 minutes (see, Table 9). These stereo-diblock copolymers featured very narrow PDIs and their molecular weights coincided with the monomer/initiator ratios according to GPC analysis. This was particularly valid for LigMg—Cl, featuring the adamantyl-phenolate group which enabled the synthesis of stereo-diblock copolymers of PDI of ≤1.07, and very high block integrities according to their very high degrees of isotacticity ($P_m$≥0.98). Evidently, the short polymerization times kept the side reactions to a minimum.

The synthesis of longer blocks was also performed: an L(800)-b-D(800) stereo-diblock copolymer was prepared in 20 minutes, and featured very high block integrity according to GPC and NMR characterization.

Regardless of block lengths, both melting temperatures and enthalpies (Tm, ΔHm) have high values which range, in the first DSC heating run, from 211 to 215° C., and from 59 to 87 J/g, respectively. These Tm and ΔHm values support the high copolymer stereoregularities and the assumed high block integrity of the copolymers. This assumption is also valid for the exceptionally long stereo-diblock copolymer L(800)-b-D(800), whose Tm and ΔHm are comparable with those of the shorter copolymers.

All the diblock copolymers crystallized either from the polymerization solution, DCM solution or melt during DSC cooling run, and are in stereocomplex crystal form. The L(800)-b-D(800) stereo-diblock copolymer is assumed to be the first example of a PLLA-PDLA system having Mw>200 kDa (either PLLA-PDLA blends or L-LA/D-LA stereo-diblock copolymers) which fully crystallizes in the stereocomplex form only, rather than as a mixture with the homochiral form. Aiming to validate the assumption that the isotactic stereo-block microstructure is a prerequisite for the crystallization in the stereocomplex phase for polymers of such high molecular weights, high molecular-weight PLLA and PDLA homochiral samples were prepared and mixed in a 1:1 ratio in DCM solution, casted films were casted therefrom, and analyzed with WAXD. Samples of PLLA and PDLA of about 800 repeat units corresponding to each block of the L(800)-b-D(800) stereo-diblock copolymer, as well as samples of about 1600 repeat units, were synthesized and tested.

Figure 10:
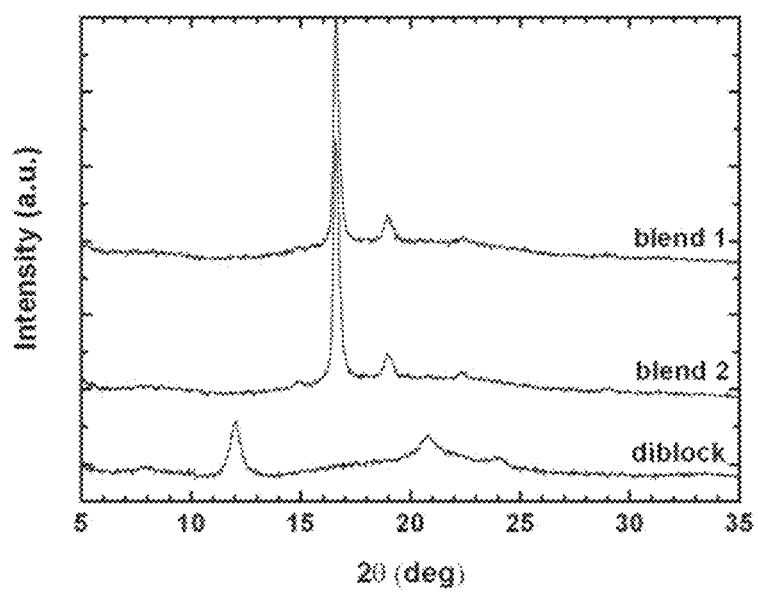
FIG. 10 presents X-ray diffraction patterns of mixtures of homochiral polymers having about 800 and 1600 repeat units, compared with L(800)-b-D(800) stereo-diblock copolymer.

FIG. 10 compares the WAXD patterns of the films, annealed at 100° C. for 10 minutes, of the L(800)-b-D(800) stereo-diblock copolymer and the two homochiral polymer mixtures. The diblock copolymer pattern only shows the reflections of the stereocomplex crystal form (at 2θ of about 12, 21, 24) while the spectra of the two mixtures only show the reflections of the homochiral crystal form (at 2θ of about 16.8, 19, 22.4_), supporting the above assumption. Notably, the L(800)-b-D(800) stereo-diblock copolymer has a high degradation temperature of 354° C. (TDTG, valued by the weight loss derivative maximum), the highest among the copolymers prepared, due to the unzipping depolymerization mechanism operating during degradation. The TDTG of the stereo-diblock copolymers increases linearly with Mn for molecular weights ranging from 20 to 150 kDa, while for higher Mns it reaches the plateau value of 350° C. (data not shown).

The synthesis of higher stereo-n-block copolymers, namely, stereo tri- and tetra-block copolymers was performed by sequential monomer additions according to the above conditions and employing Lig$^4$Mg—Cl. Surprisingly, this catalyst enabled the synthesis of stereo-n-block (n=3, 4) copolymers of different block lengths whose integrity was very high judging by their high degrees of isotacticity, ($P_m$≥0.96).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A process of ring opening polymerization of a cyclic ester, the process comprising contacting a plurality of monomers of said cyclic ester with a catalyst system comprising an organometallic magnesium complex, said organometallic magnesium complex comprising a Mg—X unit and a divergent {ONNN} ligand in coordination with said Mg—X.

2. The process of claim 1, being for preparing a polyester.

3. The process of claim 1, wherein said cyclic ester is a lactide.

4. The process of claim 1, wherein said magnesium complex is represented by Formula IIA or IIB:

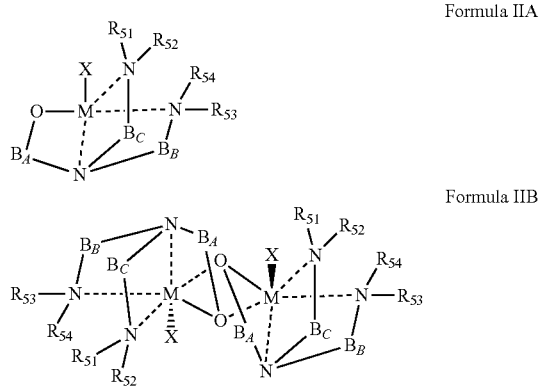

wherein:
the dashed line represents a coordinative bond;
M is magnesium;
X is a monoanionic ligand, said monoanionic ligand being other than alkoxy or aryloxy;
$B_A$, $B_B$ and $B_C$ are each independently a bridging moiety of 1 to 12 carbon atoms;
$R_{51}$ and $R_{52}$ are each independently hydrogen, alkyl, cycloalkyl, aryl or alternatively, one or both of $R_{51}$ and $R_{52}$ form together, optionally with one or more carbon atoms in $B_C$, a heteroalicyclic or heteroaromatic, 5 to 7-membered ring; and
$R_{53}$ and $R_{54}$ are each independently hydrogen, alkyl, cycloalkyl, aryl or alternatively, one or both of $R_{53}$ and $R_{54}$ form together with one or more carbon atoms in $B_B$, a heteroalicyclic or heteroaromatic, 5 to 7-membered ring.

5. The process of claim 4, wherein X is other than alkoxy or aryloxy.

6. The process of claim 4, wherein X is selected from halo and amine.

7. The process of claim 4, wherein at least one of $R_{41}$ and $R_{42}$ is a bulky rigid alkyl.

8. The process of claim 1, wherein said polymer is a block copolymer comprising a plurality of units, at least two of said units independently comprise a plurality of polymerized monomers of a cyclic ester, at least one unit of said at least two units comprises a plurality of polymerized monomers of a first cyclic ester, and at least one another unit of said at least two units comprises a plurality of polymerized monomers of a second cyclic ester, said second cyclic ester differing from said first cyclic ester by a stereoconfiguration and/or a chemical composition, the process comprising:

sequentially contacting a plurality of monomers of said first cyclic ester and a plurality of monomers of said second cyclic ester with said catalyst system comprising an initiator and an organometallic magnesium complex comprising a Mg—X unit and a divergent {ONNN} ligand in coordination with said Mg—X, to thereby sequentially effect a ring opening polymerization of said first cyclic ester and of said second cyclic ester.

9. The process of claim 8, wherein the block copolymer comprises from 2 to units.

10. The process of claim 8, wherein at least two units in said plurality of units differ from one another by a number of said polymerized monomers.

11. The process of claim 8, wherein at least 90%, or at least 95% or at least 96% or at least 98% or at least 99% of polymerized monomers in each of said units feature the same stereoconfiguration and/or chemical composition.

12. The process of claim 8, wherein said block copolymer is a stereoblock copolymer comprising at least one unit of polymerized monomers of said first cyclic ester and at least one unit of polymerized monomers of a second cyclic ester, said first cyclic ester featuring a first stereoconfiguration and said second cyclic ester featuring a second stereoconfiguration, said first and said second stereoconfigurations being different from one another, the process comprising:

sequentially contacting a plurality of monomers of said first cyclic ester featuring said first stereoconfiguration and a plurality of monomers of said second cyclic ester featuring said second stereoconfiguration with said catalyst system.

13. The process of claim 12, wherein at least 90%, or at least 95% or at least 96% or at least 98% or at least 99% of said polymerized monomers in each of said units feature the same stereoconfiguration.

14. The process of claim 8, wherein at least one of said first and second cyclic esters is a lactide or a lactone.

15. An organometallic complex represented by Formula III:

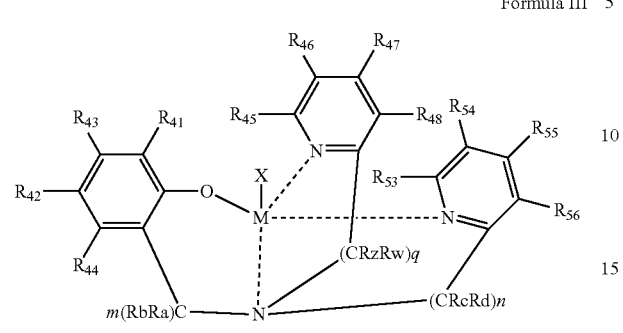

Formula III wherein:
the dashed line represents a coordinative bond;
M is magnesium;
X is a monoanionic ligand;
m, n and q are each independently an integer of from 1 to 6, or from 1 to 4, or from 1 to 2;
Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5 to 7-membered alicyclic, heteroalicyclic, aromatic or heteroaromatic ring with one or both Ra and Rb of an adjacent unit;
Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit being the same or different, and one or both Rc and Rd in one unit optionally forms a 5 to 7-membered alicyclic, heteroalicyclic, aromatic or heteroaromatic ring with one or both Rc and Rd of an adjacent unit;
Rz and Rw are each independently hydrogen, alkyl, cycloalkyl, aryl, heteroaryl, heteroalicyclic, hydroxyl, alkoxy, thiol, thioalkoxy, aryloxy, and amine, wherein when q is other than 1, Rz and Rw in each (CRzRw) unit being the same or different, and one or both Rz and Rw in one unit optionally forms a 5 to 7-membered alicyclic, heteroalicyclic, aromatic or heteroaromatic ring with one or both Rz and Rw of an adjacent unit; and
$R_{41}$-$R_{48}$ and $R_3$-$R_{56}$ are each independently selected from the group consisting of hydrogen, alkyl, cycloalkyl, aryl, halo, alkoxy, aryloxy, trialkylsilyl, heteroalicyclic, heteroaryl, and amine,
provided that:
X is other than alkoxy or aryloxy; and/or
at least one of $R_{41}$ and $R_{42}$ is a bulky rigid alkyl.

16. The organometallic complex of claim 15, wherein X is halo or amide.

17. A ligand precursor represented by Formula IV:

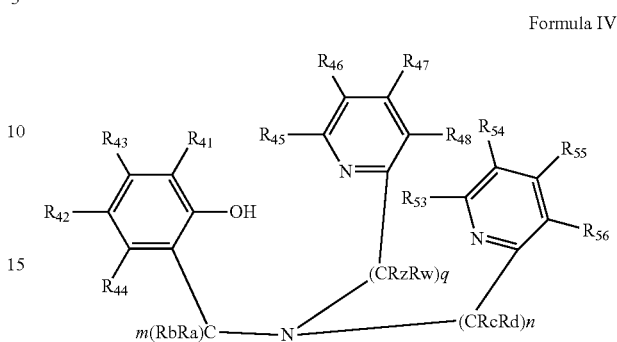

Formula IV wherein:
m, n and q are each independently an integer of from 1 to 6, or from 1 to 4, or from 1 to 2;
Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5 to 7-membered alicyclic, heteroalicyclic, aromatic or heteroaromatic ring with one or both Ra and Rb of an adjacent unit;
Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit being the same or different, and one or both Rc and Rd in one unit optionally forms a 5 to 7-membered alicyclic, heteroalicyclic, aromatic or heteroaromatic ring with one or both Rc and Rd of an adjacent unit;
Rz and Rw are each independently hydrogen, alkyl, cycloalkyl, aryl, heteroaryl, heteroalicyclic, hydroxyl, alkoxy, thiol, thioalkoxy, aryloxy, and amine, wherein when q is other than 1, Rz and Rw in each (CRzRw) unit being the same or different, and one or both Rz and Rw in one unit optionally forms a 5 to 7-membered alicyclic, heteroalicyclic, aromatic or heteroaromatic ring with one or both Rz and Rw of an adjacent unit; and
$R_{41}$-$R_{48}$ and $R_{53}$-$R_{56}$ are each independently selected from the group consisting of hydrogen, alkyl, cycloalkyl, aryl, halo, alkoxy, aryloxy, trialkylsilyl, heteroalicyclic, heteroaryl, and amine,
provided that at least one of $R_{41}$ and $R_{42}$ is a bulky rigid alkyl.

* * * * *